US011330250B2

(12) United States Patent
Kato et al.

(10) Patent No.: US 11,330,250 B2
(45) Date of Patent: *May 10, 2022

(54) THREE-DIMENSIONAL DISPLAY DEVICE AND THREE-DIMENSIONAL DISPLAY METHOD

(71) Applicant: PANASONIC INTELLECTUAL PROPERTY MANAGEMENT CO., LTD., Osaka (JP)

(72) Inventors: Yumiko Kato, Osaka (JP); Tsuyoshi Inoue, Nara (JP); Jun Ozawa, Nara (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 468 days.

This patent is subject to a terminal disclaimer.

(21) Appl. No.: 16/373,992

(22) Filed: Apr. 3, 2019

(65) Prior Publication Data

US 2019/0230344 A1 Jul. 25, 2019

Related U.S. Application Data

(63) Continuation of application No. 14/701,537, filed on May 1, 2015, now Pat. No. 10,298,917, which is a (Continued)

(30) Foreign Application Priority Data

Aug. 26, 2013 (JP) .................................. 2013-175061
Aug. 26, 2013 (JP) .................................. 2013-175071

(51) Int. Cl.
*H04N 13/327* (2018.01)
*A61B 5/055* (2006.01)
(Continued)

(52) U.S. Cl.
CPC ......... *H04N 13/327* (2018.05); *A61B 1/0005* (2013.01); *A61B 1/00009* (2013.01);
(Continued)

(58) Field of Classification Search
CPC .. H04N 13/327; H04N 13/128; H04N 13/144; G06T 7/593; G06T 7/0012;
(Continued)

(56) References Cited

U.S. PATENT DOCUMENTS

2008/0119728 A1 5/2008 Frenkel et al.
2012/0148147 A1 6/2012 Ogata et al.

FOREIGN PATENT DOCUMENTS

JP 6-292240 10/1994
JP 2009-542362 12/2009
WO 2008/002830 1/2008

OTHER PUBLICATIONS

International Search Report of PCT application No. PCT/JP2014/003796 dated Sep. 16, 2014.

*Primary Examiner* — Clifford Hilaire
*Assistant Examiner* — Kristin Dobbs
(74) *Attorney, Agent, or Firm* — Greenblum & Bernstein, P.L.C.

(57) ABSTRACT

A three-dimensional display device configured to display a main image and an additional image on a screen includes a display region candidate decider that decides one candidate region from a plurality of region candidates for the additional image to be superimposed on the main image on the screen, a depth suitability determiner that determines whether a difference between a depth of the main image displayed at a boundary region and a depth of the additional image is within a predetermined tolerance range, and an image composer that, when the difference in depth between the depth of the main image displayed at the boundary (Continued)

region and the depth of the additional image is within the tolerance range, superimposes the additional image upon the main image at the candidate region, thereby composing a composite image of the main image and the additional image, and displays the composite image on the screen.

28 Claims, 49 Drawing Sheets

Related U.S. Application Data continuation of application No. PCT/JP2014/003796, filed on Jul. 17, 2014.

(51) Int. Cl.
| | |
|---|---|
| *A61B 5/00* | (2006.01) |
| *A61B 5/0205* | (2006.01) |
| *A61B 1/00* | (2006.01) |
| *H04N 13/144* | (2018.01) |
| *H04N 13/128* | (2018.01) |
| *G06T 7/593* | (2017.01) |
| *G06V 10/40* | (2022.01) |
| *A61B 1/04* | (2006.01) |
| *G06T 7/00* | (2017.01) |
| *A61B 5/01* | (2006.01) |
| *A61B 5/021* | (2006.01) |
| *A61B 5/024* | (2006.01) |
| *A61B 5/318* | (2021.01) |
| *G06V 10/46* | (2022.01) |

(52) U.S. Cl.
CPC ............ *A61B 1/00193* (2013.01); *A61B 1/04* (2013.01); *A61B 5/0035* (2013.01); *A61B 5/0205* (2013.01); *A61B 5/055* (2013.01); *A61B 5/7425* (2013.01); *G06T 7/0012* (2013.01); *G06T 7/593* (2017.01); *G06V 10/40* (2022.01); *H04N 13/128* (2018.05); *H04N 13/144* (2018.05); *A61B 5/01* (2013.01); *A61B 5/021* (2013.01); *A61B 5/024* (2013.01); *A61B 5/318* (2021.01); *G06V 10/467* (2022.01)

(58) Field of Classification Search
CPC ..... A61B 1/00009; A61B 1/04; A61B 1/0005; A61B 1/00193; A61B 5/0035; A61B 5/0205; A61B 5/055; A61B 5/7425; G06K 9/46
USPC .......................................................... 348/77
See application file for complete search history.

| ADDITIONAL IMAGE POSITION ID | CENTER-OF-GRAVITY POSITION |
|---|---|
| 01 | (−50, 22, 0) |
| 02 | (−35, 22, 0) |
| 03 | (−20, 22, 0) |
| ⋮ | ⋮ |

FIG. 3

| ADDITIONAL IMAGE SIZE ID | HEIGHT | WIDTH |
|---|---|---|
| 01 | 4.59 | 8 |
| 02 | 9 | 16 |
| 03 | 13.5 | 24 |
| ⋮ | ⋮ | ⋮ |

FIG. 4

| ADDITIONAL IMAGE REGION ID | VERTEX 1 UPPER LEFT | VERTEX 2 UPPER RIGHT | VERTEX 3 LOWER LEFT | VERTEX 4 LOWER RIGHT |
|---|---|---|---|---|
| 01 | (−50, 25, 3) | (−43, 25, 3) | (−50, 20, 3) | (−43, 20, 3) |
| 02 | (−40, 25, 3) | (−33, 25, 3) | (−40, 20, 3) | (−33, 20, 3) |
| ⋮ | ⋮ | ⋮ | ⋮ | ⋮ |

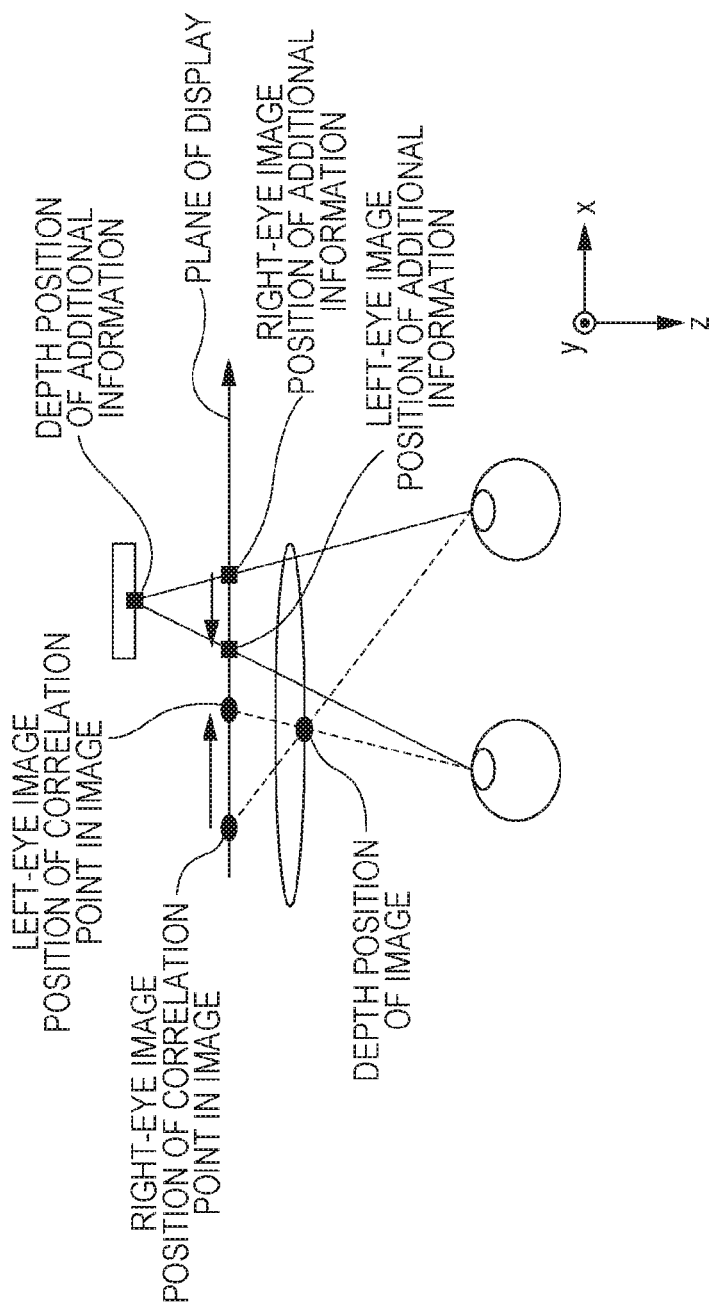

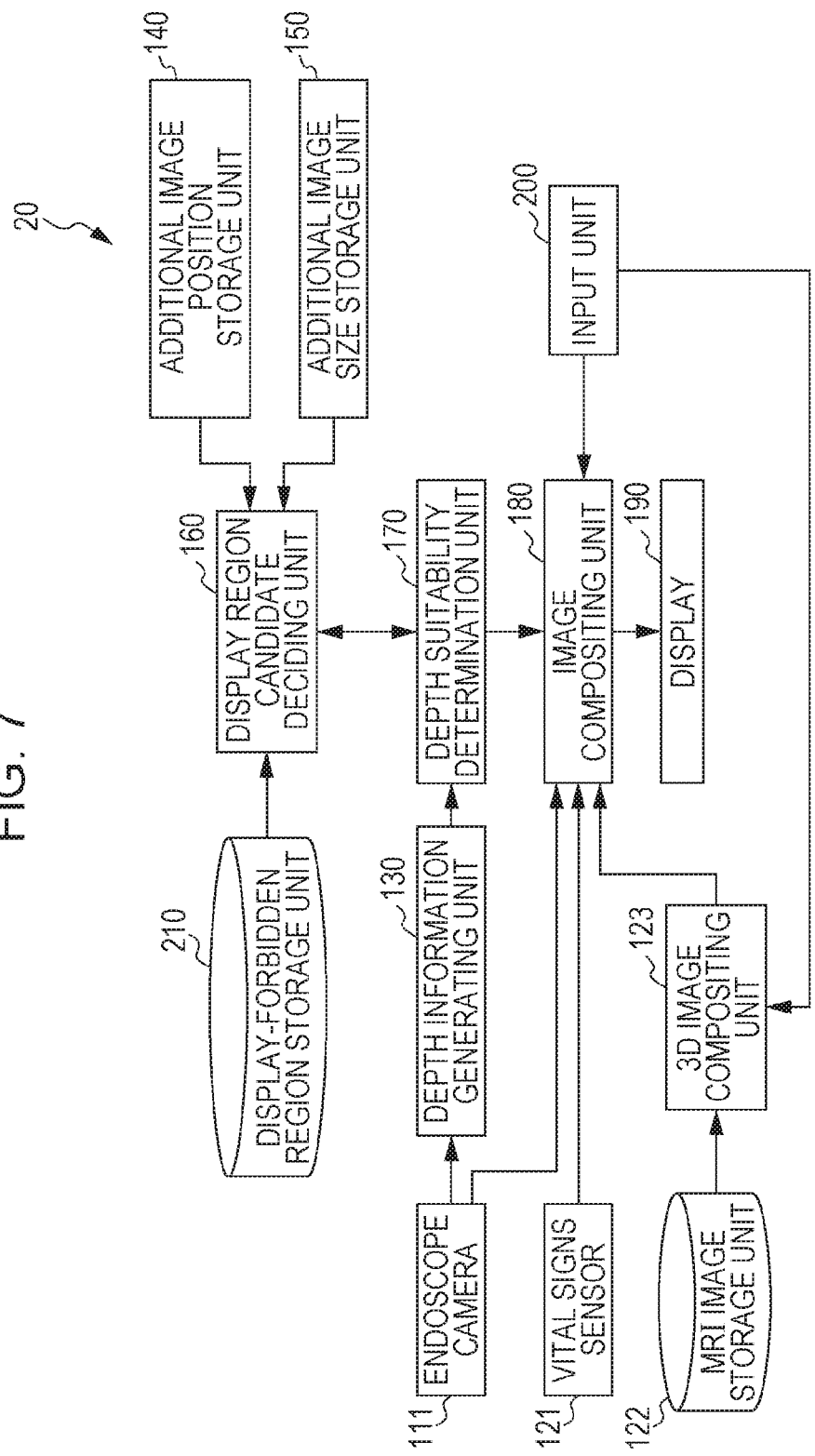

| PARTIAL REGION ID | DISPARITY (PIXELS) |
|---|---|
| D1, 1 | −800 |
| D1, 2 | −862 |
| ⋮ | ⋮ |
| D1, 10 | 3 |
| D2, 10 | 5 |
| ⋮ | ⋮ |

| CANDIDATE REGION | SHORTEST DISTANCE FROM FORBIDDEN REGION (PIXELS) | AVERAGE DIFFERENCE IN DEPTH (cm) |
|---|---|---|
| A | 100 | 7 |
| B | 30 | 6 |
| C | 200 | 3 |

ADDITIONAL IMAGE
FRAME (SMALL)

ADDITIONAL IMAGE
FRAME (LARGE)

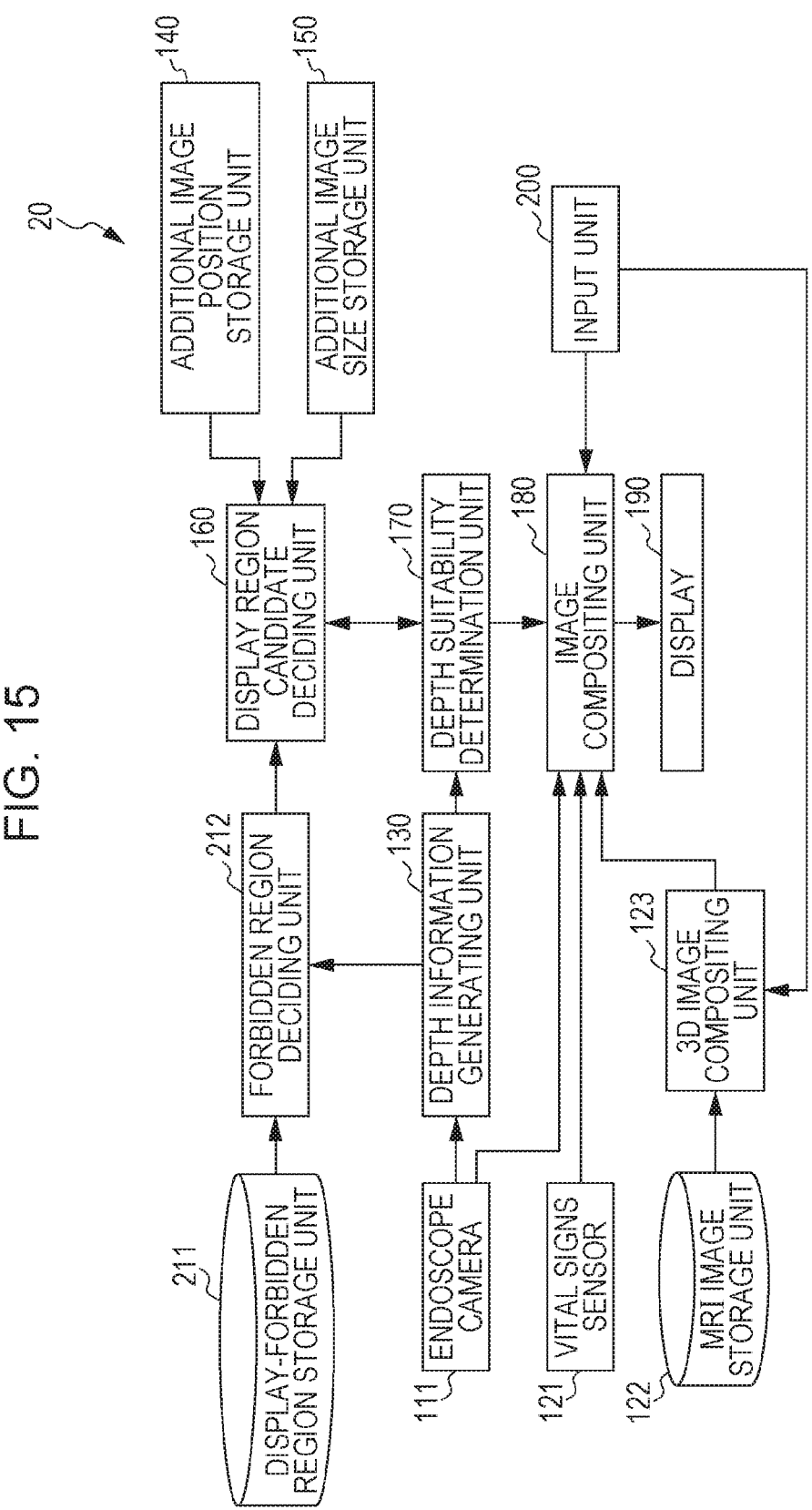

FIG. 16

| DISTANCE RANGE (cm) | VERTEX 1 UPPER LEFT | VERTEX 2 UPPER RIGHT | VERTEX 3 LOWER LEFT | VERTEX 4 LOWER RIGHT |
|---|---|---|---|---|
| 0 TO 2 | (−40, 20) | (40, 20) | (−40, −20) | (40, −20) |
| 2 TO 3 | (−35, 18) | (35, 18) | (−35, −18) | (35, −18) |
| ⋮ | ⋮ | ⋮ | ⋮ | ⋮ |

FIG. 21

| BOUNDARY REGION | | REGION ADJACENT TO BOUNDARY PLANE | |
|---|---|---|---|
| PARTIAL REGION ID | DISPARITY (PIXELS) | PARTIAL REGION ID | DISPARITY (PIXELS) |
| D1, 1 | −800 | C1 | 130 |
| D1, 2 | −862 | | |
| ⋮ | ⋮ | | |
| D1, 5 | −420 | C2 | −160 |
| ⋮ | ⋮ | | |
| D1, 10 | 3 | | |
| D2, 10 | 5 | C3 | −20 |
| ⋮ | ⋮ | | |
| D7, 10 | 58 | | |

FIG. 30

| ADDITIONAL IMAGE REGION ID | ADDITIONAL INFORMATION | VERTEX 1 UPPER LEFT | VERTEX 2 UPPER RIGHT | VERTEX 3 LOWER LEFT | VERTEX 4 LOWER RIGHT |
|---|---|---|---|---|---|
| 01 | VITAL SIGNS | (−50, 25, 3) | (−43, 25, 3) | (−50, 20, 3) | (−43, 20, 3) |
| 02 | SURGICAL SITE IMAGE | (−40, 25, 3) | (−33, 25, 3) | (−40, 20, 3) | (−33, 20, 3) |

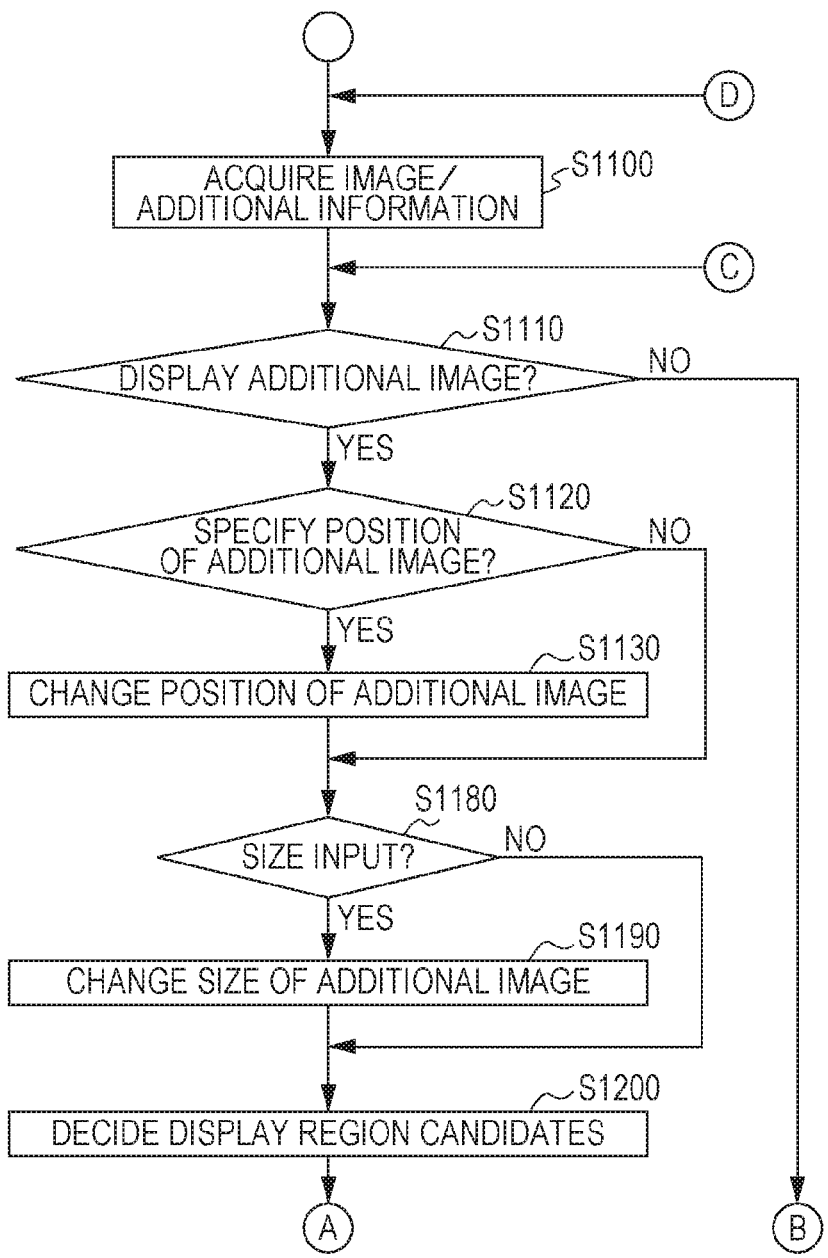

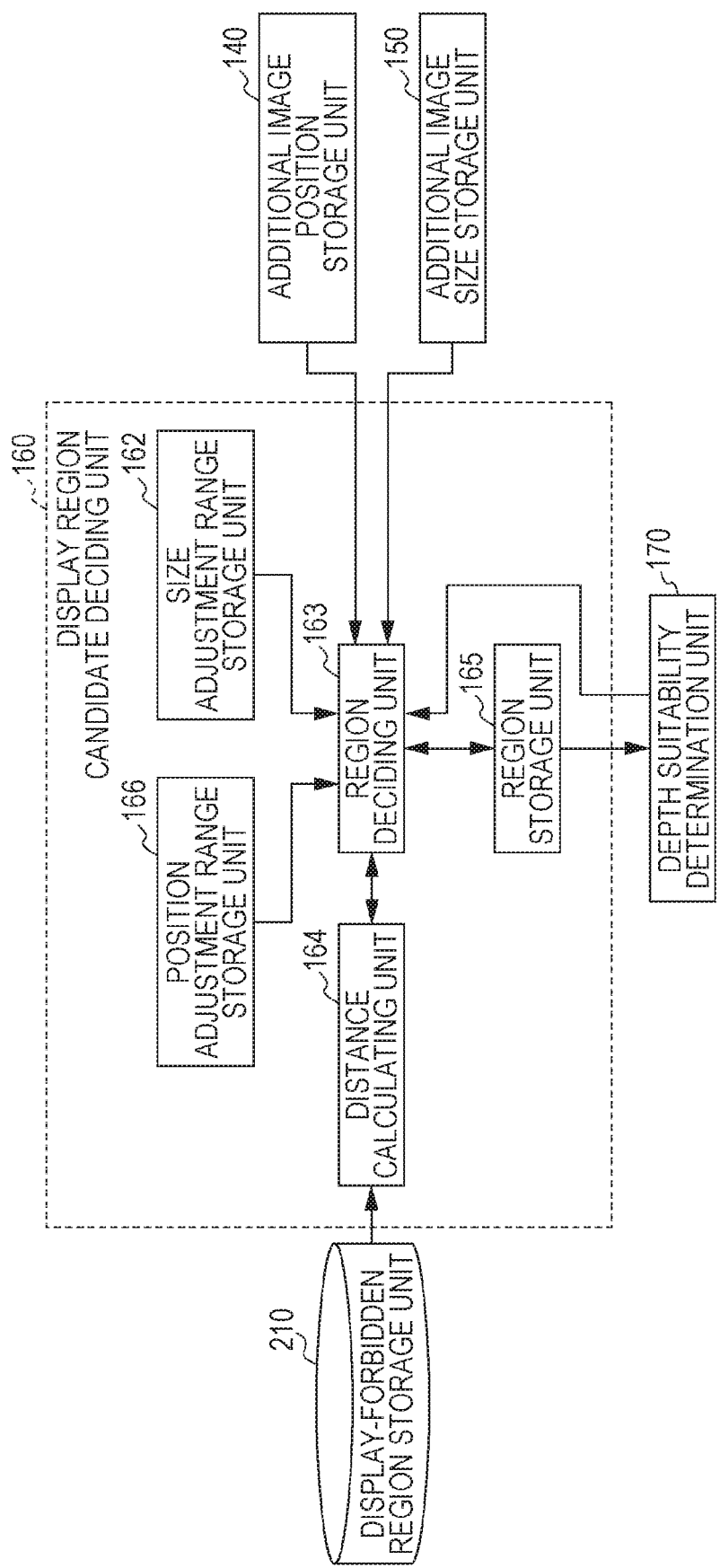

THREE-DIMENSIONAL DISPLAY DEVICE AND THREE-DIMENSIONAL DISPLAY METHOD

CROSS REFERENCE TO RELATED APPLICATION

This is a continuation application of U.S. patent application Ser. No. 14/701,537, filed May 1, 2015, which is a Bypass Continuation application of International Application No. PCT/JP2014/003796, filed on Jul. 17, 2014, and which claims the benefit of Japanese Patent Application No. 2013-175071, filed Aug. 26, 2013, and Japanese Application No. 2013-175061, filed Aug. 26, 2013, all of the disclosures of which are expressly incorporated herein by reference in their entireties.

BACKGROUND

1. Technical Field

The present disclosure relates a three-dimensional (hereinafter "3D") display device and a 3D display method.

2. Description of the Related Art

There are display devices that display moving images or still images, where additional information is superimposed on the image, to improve usability. Japanese Unexamined Patent Application Publication No. 6-292240 discloses a method for displaying a depth-direction ruler on the displayed image if the display device displays 3D images (e.g., a left-eye image and right-eye image). This makes the depth-wise position of an object to be more readily comprehended. Japanese Unexamined Patent Application Publication (Translation of PCT Application) No. 2009-542362 discloses a method for displaying information of forceps outside of a viewing angle, in an outer frame portion adjacent to the display image. Thus, the user can acquire information of the position and state of forceps outside of the display range. However, there has been recognized a need for further improvement over the above-described related art.

SUMMARY

In one general aspect, the techniques disclosed here feature a three-dimensional display device that includes: a display region candidate decider that decides one candidate region from a plurality of region candidates for an additional image to be superimposed on a main image on a screen, a depth suitability determiner that determines, based on a boundary region that is within a predetermined distance from a boundary line between the candidate region and outside of the candidate region in the main image, whether a difference between a depth of the main image displayed at the boundary region and a depth of the additional image is within a predetermined tolerance range, and an image composer that, when it is determined that the difference in depth between the depth of the main image displayed at the boundary region and the depth of the additional image is within the tolerance range, superimposes the additional image upon the main image at the candidate region, thereby composing a composite image of the main image and the additional image, and displays the composite image on the screen.

These general and specific aspects may be implemented using a system, a method, and a computer program, and any combination of systems, methods, and computer programs.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 3 is a diagram illustrating an example of size information of an additional image;

FIG. 4 is a diagram illustrating an example of region information of an additional image;

FIG. 6B is a schematic diagram illustrating an example of lines of view in a case where there is contradiction in depth between a main image and additional image;

FIG. 7 is a block diagram illustrating a functional configuration of a 3D display device according to a second embodiment;

FIG. 15 is a block diagram illustrating a functional configuration of a 3D display device according to a first modification of the second embodiment;

FIG. 16 is an example of display-forbidden region information according to a first modification of the second embodiment;

FIG. 21 is an example of disparity information of boundary regions and boundary plane adjacent regions according to the second modification of the second embodiment;

FIG. 30 is a schematic diagram illustrating an example of stored contents, stored in an additional image region storage unit;

FIG. 32A is a flowchart illustrating processing operations of a 3D display device according to an eighth modification of the second embodiment;

FIG. 33 is a block diagram illustrating a detailed functional configuration of a display region candidate deciding unit according to the eighth modification of the second embodiment;

DETAILED DESCRIPTION

Figure 1:
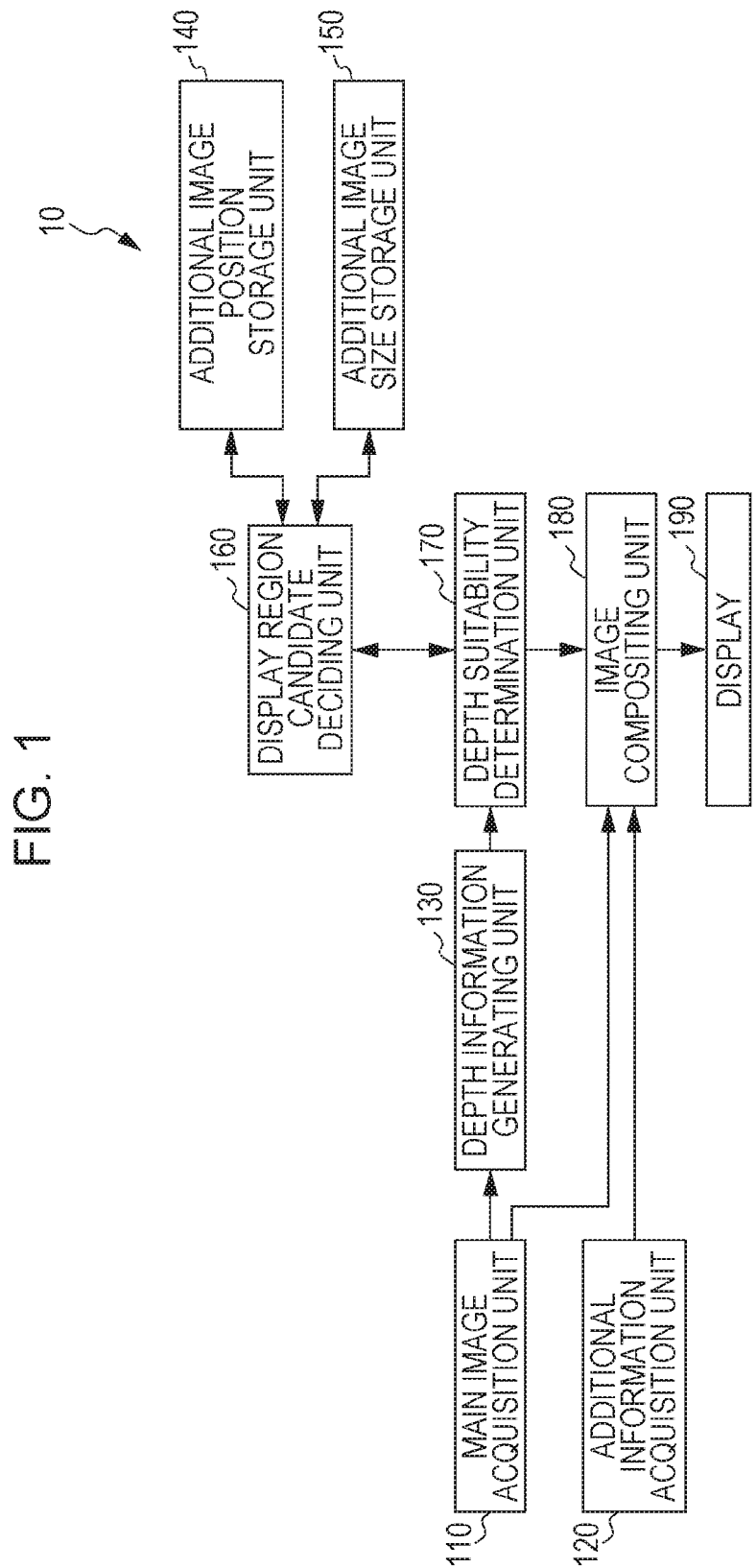
FIG. 1 is a block diagram illustrating a functional configuration of a 3D display device according to a first embodiment.

Underlying Knowledge Forming Basis of the Present Disclosure

First, description will be given regarding studies made by the present inventors to reach the aspects of the present disclosure. The present inventors have found that the following problems occur in the related art.

In a case of displaying a new object in part of a 3D image, like the ruler in Japanese Unexamined Patent Application Publication No. 6-292240, there are cases where the difference between the displayed depth position of the object decided by the disparity of the position of the object in the left-eye image and the position of the object in the right-eye image, and the depth position of an object displayed in the original 3D image is too great, or where there is contradiction in the depth position (an object at a deeper position hides an nearer object). The display in the outer frame portion in Japanese Unexamined Patent Application Publication (Translation of PCT Application) No. 2009-542362 has also had a similar problem in that there are cases where contradiction occurs where the difference between a displayed image in the screen and a displayed image in the frame is too great, or where there is contradiction in the depth position between the displayed image in the screen and a displayed image in the frame. Such excessively great difference in depth and contradiction in depth positions cause user discomfort and fatigue, placing a large load on the user. The present inventors studied the above problems to reach the aspects of the present disclosure.

According to one aspect of the present disclosure, a three-dimensional display device includes: a display region candidate deciding unit that decides one candidate region from a plurality of display region candidates of an additional image which shields part of a main image of a three-dimensional image on a screen; a depth suitability determination unit that determines, in a case of assuming that the additional image is to be displayed in the candidate region which the display region candidate deciding unit has decided, whether or not a difference in depth between depth of the main image displayed at a boundary region which is a region on the main image and within a predetermined distance from a boundary line of the candidate region, and the depth of the additional image, is within a predetermined tolerance range; an image compositing unit that, in a case where determination is made by the depth suitability determination unit that the difference in depth is within the tolerance range, superimposes the additional image upon the candidate region on the main image, thereby compositing the main image and the additional image, and displays an image obtained as a result of the compositing on the screen; and a possibly-unsuitable region deciding unit that decides, in the main image, a first region that has a possibility of the depth protruding to a near side beyond a predetermined depth range, and a second region that has a possibility of the depth recessing to a far side beyond a predetermined depth range. The display region candidate deciding unit further decides a candidate region to shield the first region and the second region decided by the possibly-unsuitable region deciding unit.

According to this aspect, an additional image is displayed in a case where the difference in depth between the main image and additional image across the boundary line of the additional image is within the tolerance range. Depth contradiction due to displaying the additional image at a region greatly protruding to the near side, for example, can be resolved. Accordingly, user discomfort and fatigue can be prevented.

Embodiments will be described in detail with reference to the drawings. Note that the descriptions made in the embodiment described below are all either comprehensive or specific examples. Values, shapes, materials, components, placements and connections of components, steps, orders of steps, and so forth, set forth in the following embodiments, are only exemplary, and are not intended to restrict the Claims. Components in the following embodiments which are not included in an independent Claim indicating the highest concept are described as being optional components.

Description in detail beyond what is necessary may be omitted in the following. For example, detailed description of well-known items and repetitive description of configurations which are essentially the same may be omitted. This is to avoid unnecessarily redundant description, and to facilitate understanding of those skilled in the art.

First Embodiment

Configuration

FIG. 1 is a block diagram illustrating a functional configuration of a 3D display device 10 according to a first embodiment. The 3D display device 10 displays 3D images. That is to say, the 3D display device 10 performs stereoscopic display of images. More specifically, the 3D display device 10 displays 3D images by a head mounted display (HMD). An HMD displays 3D images by a display in close proximity the eyes of the user. An HMD uses a left-eye image and a right-eye image which have disparity, displaying the right-eye image on a display in close proximity with the right eye of the user, and displaying the left-eye image on a display in close proximity with the left eye of the user. The left and right displays are situated so that the left eye cannot see the right-eye image, and the right eye cannot see the left-eye image. There is another type of stereoscopic display, called 3D glasses, examples of which include liquid crystal shutter glasses and polarized glasses. The user wearing the 3D glasses is presented with a left-eye image and a right-eye image which have disparity. The 3D display device 10 may also display 3D images by a naked-eye stereoscopic system. A naked-eye stereoscopic system is a stereoscopic system which does not use 3D glasses, examples of which include the parallax barrier display and lenticular lens display.

The 3D display device 10 illustrated in FIG. 1 includes a main image acquisition unit 110, an additional information acquisition unit 120, a depth information generating unit 130, an additional image position storage unit 140, an additional image size storage unit 150, a display region candidate deciding unit 160, a depth suitability determination unit 170, an image compositing unit 180, and a display 190.

The main image acquisition unit 110 acquires image information for 3D display having left and right disparity (3D images). The images have been imaged at the same time by two cameras arrayed in tandem, for example. The image of one camera is the right-eye image, and the image of the other camera is the left-eye image. The images may be currently being imaged, or may be recorded beforehand. Alternatively, the 3D display images having left and right disparity may be an image imaged by a single camera which has been subjected to image processing so as to generate left and right images by disparity.

The additional information acquisition unit 120 acquires additional information to be added to the image information which the main image acquisition unit 110 acquires. An example of additional information is information temporally synchronous with the image information, that has been acquired by a sensor other than the camera but situated nearby the camera imaging the main image. Another example of additional information is a 3D image created separately from the main image.

The depth information generating unit 130 obtains the left and right disparity of the 3D image which the main image acquisition unit 110 has obtained, and generates depth information of the main image. For example, the depth information generating unit 130 extracts correlation points between the right-eye image and the left-eye image, obtains the left and right disparity of the correlation points, and calculates the depth.

Figures 2A, 2B:
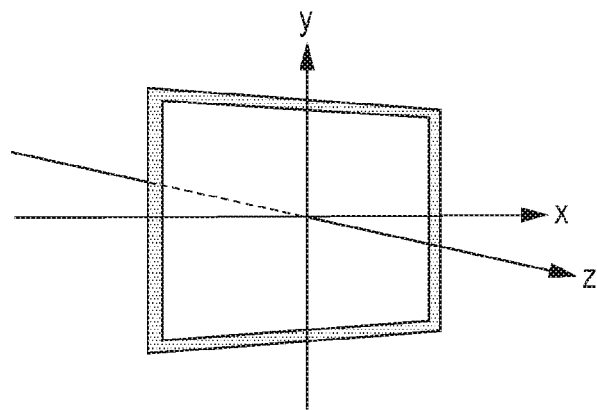
FIG. 2A is a diagram illustrating an example of additional image position information.
FIG. 2B is a schematic diagram illustrating an example of a coordinates system according to the first embodiment.

The additional image position storage unit 140 stores, for the additional information acquired by the additional information acquisition unit 120, the position for display on the screen of the display 190. For example, the additional image position storage unit 140 stores coordinates in 3D space when the 3D image is displayed, as the position. Alternatively, the additional image position storage unit 140 may store the display position on the display 190 of each of the left-eye image and right-eye image as the position. FIG. 2A illustrates an example of additional image position information stored in the additional image position storage unit 140. FIG. 2B schematically illustrates an example of 3D coordinates for identifying additional image positions. The additional image position storage unit 140 stores an additional image position ID for identifying the position of additional images (images representing additional information), and the center-of-gravity position of the additional image positions corresponding to the additional image position IDs, as illustrated in FIG. 2A. The center-of-gravity position is a point on coordinate axes arranged as illustrated in FIG. 2B which represents 3D space.

The additional image size storage unit 150 stores the size of displaying the additional information acquired by the additional information acquisition unit 120 as an additional image on the screen of the display 190. FIG. 3 illustrates an example of size information of additional images stored in the additional image size storage unit 150. The additional image size storage unit 150 in the example in FIG. 3 stores additional image size IDs to identify size information of additional images, and the dimensions of the additional images in terms of height and width. In the first embodiment, the additional images are shaped as rectangles, with the size thereof specified by the length of the sides in the height direction and the length of the sides in the width direction. The way in which the sizes of the additional images are expressed differs depending on the shape. For example, if an additional image is an ellipse, the size is specified by the major and minor axes.

While description has been made that the additional image position storage unit 140 and the additional image size storage unit 150 respectively store the position and size of additional images, the position and size of additional images may be stored in a single storage unit, such as an additional image region storage unit for example. In a case where the additional image is a polygon for example, the additional image region storage unit stores the coordinate positions in 3D space for the vertices of the polygon. This enables the position and size to be stored together. FIG. 4 illustrates an example of contents stored in an additional image region storage unit in a case of storing the position and size of additional image as a region. In the example illustrated in FIG. 4, the additional images are rectangles which have four sides, parallel to the four sides of the screen of the display 190, and the coordinate positions of the four vertices are stored corresponding to IDs identifying the regions of the additional images.

The display region candidate deciding unit 160 decides candidates for a display region to display one or a plurality of additional information on the screen of the display 190 as the additional image. In the following description, the term "display region" as such means a display region for additional information or an additional image.

The depth suitability determination unit 170 detects depth difference greater than a predetermined value, or depth contradiction, in the difference in depth between the display region of an additional image and a peripheral portion of the display region of an additional image in a main image generated by the depth information generating unit 130. This detection is made based on information of additional image display region candidates decided by the display region candidate deciding unit 160 and depth information of the main image generated at the depth information generating unit 130.

The image compositing unit 180 displays the 3D image acquired by the main image acquisition unit 110 on the display 190, and composites the main image and an additional image to display the additional information acquired by the additional information acquisition unit 120 in at least one of the candidates for a display region which the display region candidate deciding unit 160 has decided, as an additional image.

The display 190 displays the image composited by the image compositing unit 180 on the screen.

Operations

Figure 5:
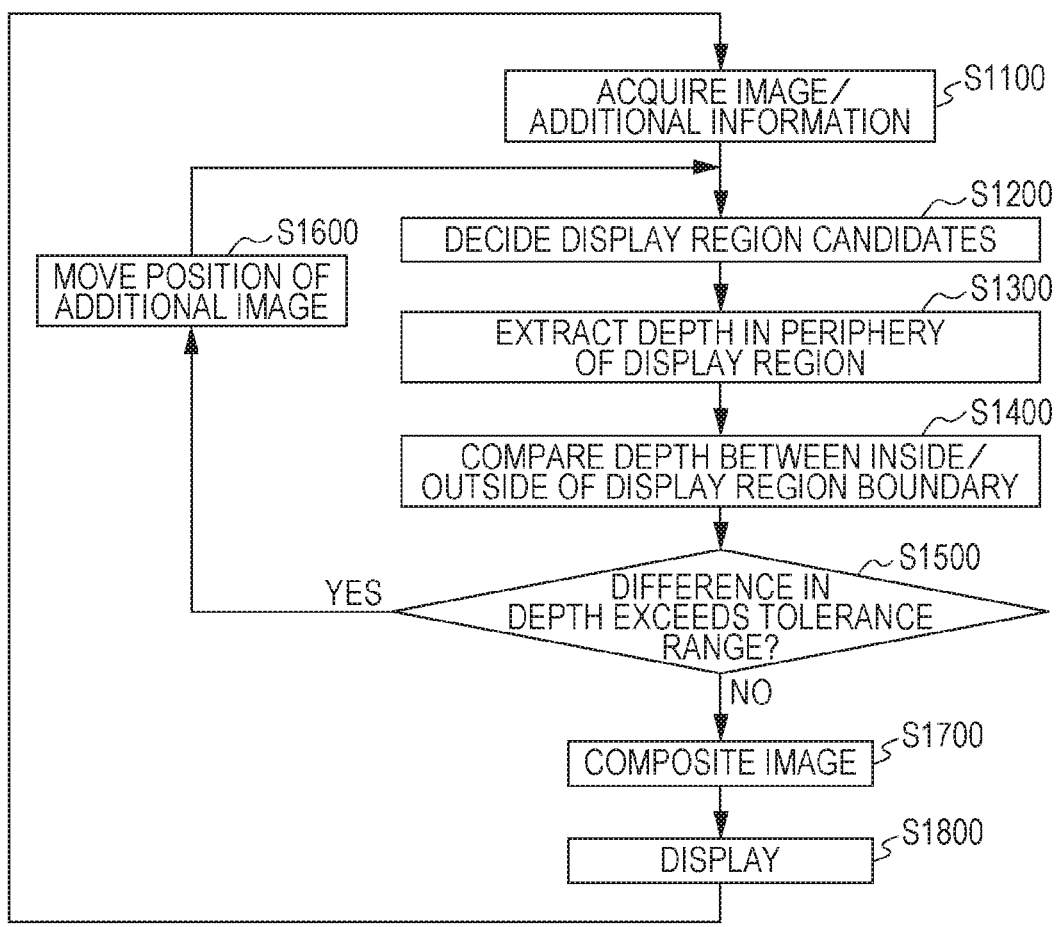
FIG. 5 is a flowchart illustrating processing operations of the 3D display device according to the first embodiment.

FIG. 5 is a flowchart illustrating processing operations of the 3D display device 10 according to the first embodiment. First, the main image acquisition unit 110 acquires image information for 3D display that has left and right disparity, and the additional information acquisition unit 120 acquires additional information corresponding to the main image indicated by the image information (step S1100). The additional information may be information temporally synchronous with the main image, or information not temporally synchronous.

Next, the display region candidate deciding unit 160 decides candidates for the display region, based on the size of the additional image stored in the additional image size storage unit 150 and the position of the additional image stored in the additional image position storage unit 140 (step S1200). One or a plurality of information of additional image size and position is stored, and the display region candidate deciding unit 160 decides one or more additional image display region candidates. The display region candidate deciding method is as follows, for example. First, one additional image position information stored in the additional image position storage unit 140 is selected, thereby deciding a display position, and further, one additional image size information stored in the additional image size storage unit 150 is selected, thereby deciding the additional image size.

The depth suitability determination unit 170 extracts a boundary line or boundary plane of the display region candidate of the additional image decided in step S1200. A boundary plane is a depth-direction face orthogonal to the plane of the display 190. The depth suitability determination unit 170 identifies a portion in the main image acquired in step S1100 in contact with the boundary line or boundary plane of the additional image, and extracts depth information (step S1300). The depth information generating unit 130 generates and holds the depth information of the main image by the time that the main image acquisition unit 110 acquires the main image in step S1100 and the depth suitability determination unit 170 extracts the depth information in step S1300.

Further, the depth suitability determination unit 170 compares the depth of the display region of the additional image obtained by information of the position of the additional image stored in the additional image position storage unit 140 by the display region candidate deciding unit 160, with the depth of the main image at a portion in contact with the boundary line or boundary plane of the additional image extracted in step S1300 (step S1400).

The depth suitability determination unit 170 determines whether or not the difference in depth between the main image and additional image displayed across the boundary lines or boundary plane exceeds a predetermined tolerance range (step S1500). The difference in depth is expressed on a depth-wise coordinate axis, on which the value increases toward the protruding side for example, which is to say toward the user from the display 190. In this case, if a value obtained by subtracting the depth value of the main image nearby the boundary line from the depth value of the additional image is a positive value, this means that the additional image is nearer, protruding toward the user, and the main image is at a deeper position than the additional image. If a value obtained by subtracting the depth value of the main image nearby the boundary line from the depth value of the additional image is a negative value, this means that the additional image is of a smaller value and the main image is at a position protruding toward the user. The additional image is displayed hiding a portion of the main image, so the hidden main image is at a deeper position, and the hiding additional image is nearer than the main image, so that the additional image overwrites the main image. However, if this value is a negative value, this indicates that a depth contraction has occurred in which the depth position of the additional image which has been set is deeper than that of the main image. Depth contradiction causes user fatigue and 3D sickness, so a tolerance range is set where, for example, depth contradiction exceeding 1 cm is unacceptable.

On the other hand, even if there is no depth contradiction, it is known that great depth differences at close portions lead to user fatigue. Accordingly, so a tolerance range is set where, for example, depth difference exceeding 15 cm is unacceptable. Thus, the tolerance range is −1 cm to 15 cm, for example. In a case where determination is made in step S1500 that the difference in depth exceeds the tolerance range, i.e., step S1500 yields a result of "yes", the flow advances to step S1600. On the other hand, in a case where determination is made in step S1500 that the difference in depth is within the tolerance range, i.e., step S1500 yields a result of "no", the flow advances to step S1700.

While the tolerance range for difference in depth will be described as being a fixed value of −0 cm to 15 cm here, the tolerance range may be set variably depending on the depth position of the additional image. The settings may be such that greater the depth of the additional image, i.e., the greater the degree of protrusion of the additional image toward the user, the narrower the tolerance range is, and the smaller the depth coordinates of the additional image is and the farther the additional image appears from the user, the larger the tolerance range for difference in depth is.

The display region candidate deciding unit 160 changes the display position of the additional image (step S1600). Changing of the display position is performed by selecting, from display positions stored in the additional image position storage unit 140, a display position not selected as a display position candidate in step S1200. After step S1600, the flow returns to step S1200.

The image compositing unit 180 composites the main image acquired in step S1100, and the additional image representing the additional information acquired in S1100 (step S1700). More specifically, the image compositing unit 180 displays the main image on the screen of the display 190, and superimposes the additional image over the main image so as to be displayed on the display region selected from the display region candidates decided in step S1200 as the display region, thereby compositing the images.

The display 190 displays the 3D image composited in step S1700 (S1800). After displaying the 3D image on the display 190 in step S1800, the flow returns to step S1100. Repeating steps S1100 through S1800 causes the 3D display device 10 to acquire images and additional information in increments of processing, and continue displaying of images. The present embodiment is applicable in cases where the contents of the main image and additional image are moving images, as well.

Advantages and Effects

Thus, the 3D display device 10 according to the present embodiment decides display regions for additional images when displaying additional information (additional images) over or adjacent to 3D images, such that states where there is a great difference in depth without and outside, or states where there is depth contradiction are avoided. Accordingly, user discomfort and fatigue due to excessively large difference in depth or depth contradiction can be prevented. While the first embodiment has been described with regard to an arrangement where the tolerance range is set for difference in depth, the tolerance range may be set for difference in disparity as well.

Figure 6A:
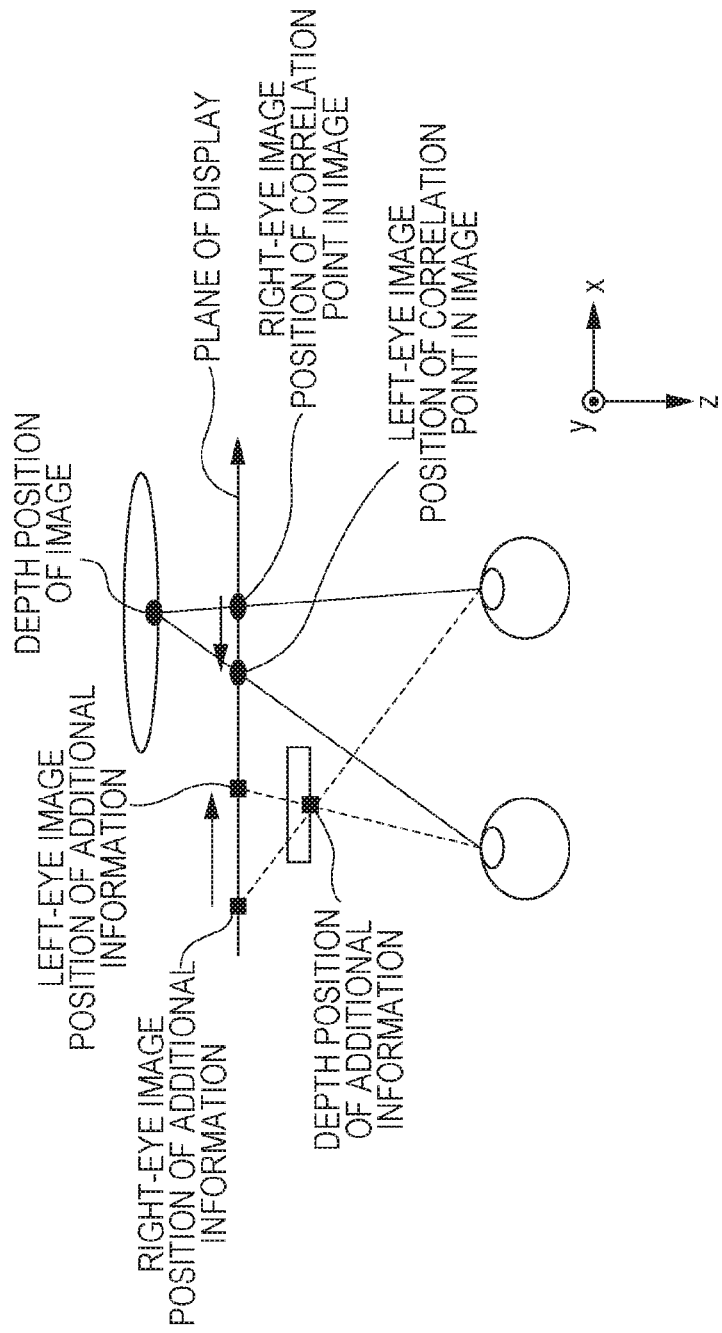
FIG. 6A is a schematic diagram illustrating an example of lines of view in a case where there is no contradiction in depth between a main image and additional image.

FIGS. 6A and 6B schematically illustrate the relationship between the depth position and disparity of the main image and additional image displayed on the display 190. FIG. 6A illustrates a state where there is no depth contradiction, and the additional image is displayed on the near side from the main image. FIG. 6B illustrates a state where there is depth contradiction, and the additional image is displayed at a deeper position than the main image but is displayed without being hidden by the nearer main image.

The coordinates on the display are set such that the values are larger toward the right and smaller toward the left, when facing the display from the front. In a case of calculating disparity as a value obtained by subtracting the value of the x-coordinate of the left-eye image from the value of the x-coordinate of the right-eye image, the disparity of a point displayed on the plane of the display is 0, and the disparity of a point viewed as appearing deeper than the plane of the display, indicated by the left-facing arrows in FIGS. 6A and 6B, is a positive value. On the other hand, the disparity of a point viewed as appearing nearer than the plane of the display, indicated by the right-facing arrows in FIGS. 6A and 6B, is a negative value.

In such a relationship, in a case where the value obtained by subtracting the disparity of the outside of the display region of the additional image from the disparity of the inside of the display region of the additional image is negative, the depth of the inside of the display region of the additional image is nearer and the outside of the display region of the additional image is deeper. That is to say, the display region of the additional image is nearer than the outside of the display region, so the additional image is presented to the near side of the main image acquired by the main image acquisition unit 110, so there is no depth contradiction.

On the other hand, in a case where the value obtained by subtracting the disparity of the outside of the display region of the additional image from the disparity of the inside of the display region is positive, as in the case in FIG. 6B, the depth of the inside of the display region is deeper than the main image acquired by the main image acquisition unit 110 and the additional image should be presented at a depth position hidden by the main image, so there is depth contradiction. Accordingly, the tolerance range is set such that the tolerance range is small in a case where the value obtained by subtracting the disparity of the outside of the display region from the disparity of the inside of the display region is positive, and in a case where the value obtained by the subtraction is a negative value, the tolerance range is set so that the value obtained by the subtraction is not smaller than a certain value. In a case where the value obtained by subtracting the disparity of the outside of the display region from the disparity of the inside of the display region is negative, a smaller value obtained by subtracting the disparity of the outside of the display region from the disparity of the inside of the display region means a larger absolute value, which means a greater difference in disparity, and thus greater difference in depth. The tolerance range in depth can thus be set by setting the disparity, with the range of difference in disparity being stipulated such that the difference in depth is no greater than a certain level.

While description has been made in the first embodiment where the depth suitability determination unit 170 makes a binary determination regarding whether or not the difference in depth between the main image and additional image across the boundary plane of the additional image exceeds the tolerance range, an arrangement may be made where a suitability is calculated from the magnitude of difference from the tolerance range that the difference in depth of the main image and additional image has, and adjusts the display region of the additional image based according to this suitability. This suitability is expressed as a function representing the relationship between the difference in depth of the main image and additional image and suitability, or a correlation table or the like.

Second Embodiment

While the 3D image (main image) and additional image were not described as being an image and information of any particular type in the first embodiment, the 3D image may be an endoscopic surgery image, and the additional information represented by the additional image may include vital signs information during the surgery, such as pulse, blood pressure, and so forth. The additional image may further include image information such as a magnetic resonance imaging (MRI) image or computed tomography (CT) image taken before the surgery.

The 3D image in a second embodiment is a real-time image of an affected area being treated by endoscopic surgery using a stereo camera, and the additional information is vital signs information of the patient during the surgery, and MRI image information taken and stored before the surgery. The types of additional information are only exemplary, and other types of information may be displayed as additional information as well.

Configuration

FIG. 7 is a block diagram illustrating a functional configuration of a 3D display device 20 according to the second embodiment. The configuration is the same as the 3D display device 10 according to the first embodiment illustrated in FIG. 1, other than the points that the main image acquisition unit 110 has been replaced by an endoscope camera 111, the additional information acquisition unit 120 has been replaced by a vital signs sensor 121, and an MRI image storage unit 122, 3D image compositing unit 123, display-forbidden region storage unit 210, and input unit 200 have been newly added. Portions which are the same as those in FIG. 1 are denoted by the same reference numerals, and description will be omitted.

The 3D display device 20 includes the endoscope camera 111, vital signs sensor 121, MRI image storage unit 122, 3D image compositing unit 123, depth information generating unit 130, additional image position storage unit 140, additional image size storage unit 150, display region candidate deciding unit 160, depth suitability determination unit 170, image compositing unit 180, display 190, display-forbidden region storage unit 210, and input unit 200.

The endoscope camera 111 is a 3D imaging endoscope camera including a stereo camera.

The vital signs sensor 121 is a sensor attached to the body of the patient during surgery. Examples of the vital signs sensor 121 include a thermometer, an electrocardiogram, a sphygmomanometer, a pulse oximeter, an electroencephalograph, and so forth. In the present embodiment, description will be made with the vital signs sensor 121 serving as an electrocardiogram and a sphygmomanometer.

The MRI image storage unit 122 stores 3D image information including images of the affected area to be treated by surgery, which have been recorded by an MRI system before surgery. While description is made in the present embodiment regarding image information recorded by an MRI system before surgery as image information, image information of X-ray images, CT image information, and so forth, may be used as well.

The 3D image compositing unit 123 composites image information stored in the MRI image storage unit 122 into images of a format which can be displayed on the display 190, as specified slices or a spectrogram of a specified range.

The display-forbidden region storage unit 210 stores information representing a region determined beforehand where an affected area to be subjected to surgery has been photographed, and information representing a display-forbidden region for the additional image. The user, who is a surgeon, needs to watch the affected area throughout the surgery. Accordingly, the additional image should be displayed outside of a region displaying the affected area.

The display-forbidden region for the additional image is a rectangular fixed region centered on the screen center of the display 190, and the display-forbidden region storage unit 210 stores coordinate positions of the four vertices of the rectangle as information representing the display-forbidden region for the additional image in the second embodiment. The endoscope camera 111 is situated by a guide pipe at a location where the affected area to be treated by surgery can be readily observed. The endoscope camera 111 can zoom in toward the affected area and zoom out away from the affected area, along the axial direction of the guide pipe. The guide pipe is fixed during surgery, so the endoscope camera 111 does not move in any other direction than along the axis of the guide pipe.

While the display-forbidden region has been described as being a fixed region in the second embodiment, the region may be changed depending on the distance between the camera and the affected area. In this case, the display-forbidden region storage unit 210 stores information representing the display-forbidden region corresponding to the distance between the camera and the affected area. For example, the display-forbidden region storage unit 210 stores the coordinates of the vertices of the display region for each range of distance between the camera and the affected area.

The input unit 200 is a processing unit where the user instructs whether or not to display an additional image, and inputs conditions for the content to be displayed as an additional image. The user who is the surgeon can display information acquired by the vital signs sensor 121 and MRI images as necessary, by inputting instructions using the input unit 200 during surgery. If the additional image is unnecessary, display of the additional image can be cancelled. Further, the user who is the surgeon can conduct conditions, such as whether an MRI image should be displayed as a slice 2D image or as a 3D image, what range should be displayed, and so forth, using the input unit 200.

Note that the additional information in the second embodiment is the vital signs information acquired by the vital signs sensor 121 during surgery, and the MRI image information stored before surgery. The two types of additional information are to be displayed as separate additional images in respective display regions.

While description has been made in the second embodiment that vital signs information and MRI image information as to be displayed as separate additional image, one additional image may be generated and displayed including multiple types of additional information together.

Operations

Figure 8:
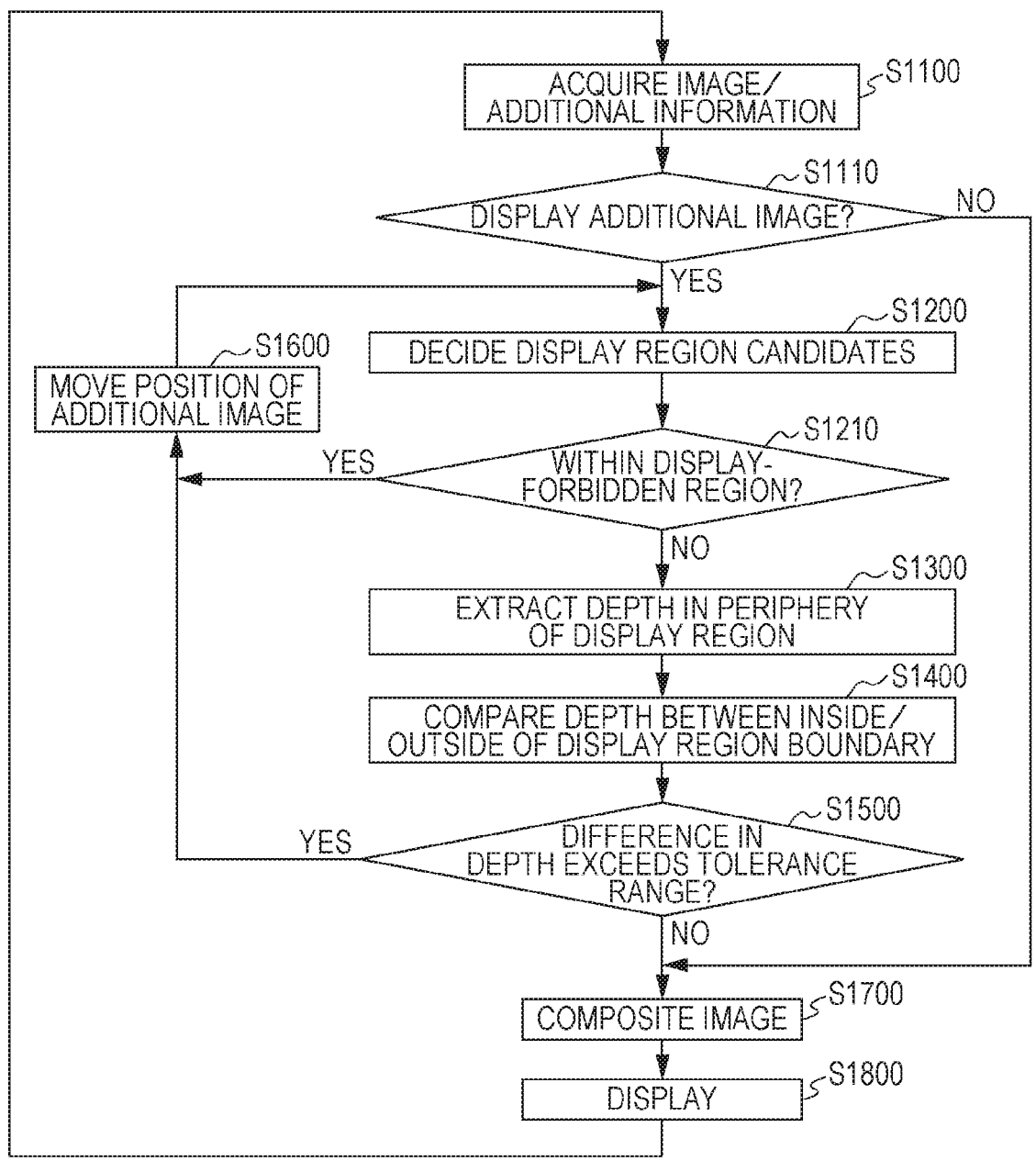
FIG. 8 is a flowchart illustrating processing operations of the 3D display device according to the second embodiment.

FIG. 8 is a flowchart illustrating processing operations of the 3D display device 20 according to the second embodiment. This flowchart is the same as that in FIG. 5 in the first embodiment, other than steps S1110 and S1210 have been added. Portions which are the same as those in FIG. 5 are denoted by the same reference numerals, and description will be omitted.

First, the endoscope camera 111 acquires image information for 3D display having left and right disparity, as a main image, and the vital signs sensor 121 measures the current cardioelectric potential and blood pressure of the patient as additional information (step S1100).

The input unit 200 acquires display control signals according to user input, and detects instruction input to display an additional image (step S1110). In a case where additional image display instruction input is detected in step S1110, i.e., in a case where step S1110 yields "yes", the flow advances to step S1200. In a case where additional image display instruction input is not detected in step S1110, i.e., in a case where step S1110 yields "no", the flow advances to step S1700.

In step S1700, the image compositing unit 180 composites an endoscope camera image which is a main image with no additional image as a display image.

The display region candidate deciding unit 160 decides candidates for the display region, from the size of the additional image stored in the additional image size storage unit 150, and the position of the additional image stored in the additional image position storage unit 140 (step S1200). For example, the display region candidate deciding unit 160 arbitrarily selects one unselected combination of additional image size stored in the additional image size storage unit 150 and additional image position stored in the additional image position storage unit 140, and decides a region represented by the selected combination as a display region candidate.

The display region candidate deciding unit 160 determines whether or not the display region candidate decided in step S1200 includes the display-forbidden region stored in the display-forbidden region storage unit 210 (step S1210). In a case where determination is made in step S1210 that the display region candidate includes the display-forbidden region, i.e., in a case where step S1210 yields "yes", the flow advances to step S1600.

In step S1600, the display region candidate deciding unit 160 moves the display position of the additional image and stores the moved display position in the additional image position storage unit 140. That is to say, the display region candidate deciding unit 160 may move the display position of the additional image to a position where the display region candidate does not include the display-forbidden region, or may move the display position of the additional image in a predetermined direction by a predetermined amount.

In a case where determination is made in step S1210 that the display region candidate does not include the display-forbidden region, i.e., in a case where step S1210 yields "no", the flow advances to step S1300.

Repeating steps S1200, S1210, and S1600 decides the display region candidate while avoiding the display-forbidden region. The depth suitability determination unit 170 extracts a boundary line or boundary plane of the additional image display region candidate decided in step S1200, and extracts depth information in the periphery of the boundary line or boundary plane (step S1300).

The depth suitability determination unit 170 further compares the depth of the display region of the additional image which the display region candidate deciding unit 160 has obtained from the position information of the additional image stored in the additional image position storage unit 140 with the depth of the main image at the portion adjacent to the boundary line or boundary plane of the additional image extracted in step S1300 (step S1400).

The depth suitability determination unit 170 determines whether or not the difference in depth of the main image and additional image displayed across the boundary line or boundary plane exceeds the predetermined tolerance range (step S1500). The tolerance range is −1 cm to 15 cm, in the same way as the first embodiment, for example. In a case where determination is made in step S1500 that the difference in depth exceeds the tolerance range, i.e., in a case where step S1500 yields "yes", the flow advances to step S1600. In a case where determination is made in step S1500 that the difference in depth is within the tolerance range, i.e., in a case where step S1500 yields "no", the flow advances to step S1700.

In step S1600 the display region candidate deciding unit 160 moves the display position of the additional image, stores the moved display position in the additional image position storage unit 140, and thereafter the flow returns to step S1200.

In step S1700, the image compositing unit 180 composites the main image acquired in step S1100 and the additional image representing the additional information acquired in step S1100. Specifically, the image compositing unit 180 displays the main image on the screen of the display 190, and displays the additional image on the main image so as to be displayed in the display region which is the display region candidate decided in step S1200 as the display region, thus compositing the image.

The display 190 displays the 3D image composited in step S1700 (step S1800), and after displaying the 3D image on the display 190 in step S1800, the flow returns to step S1100. Repeating steps S1100 through S1800 causes the 3D display device 20 to acquire main images and additional information in increments of processing, and continue displaying of 3D images. The present embodiment is applicable in cases where the contents of the main image and additional image are moving images, as well.

Depth Suitability Determination Unit 170: Details of Steps S1300 to S1500

An example where there are two additional images will be described in the second embodiment. Note that the number of additional images may also be one, or three or more. One of the additional images in the second embodiment is a graph showing the cardioelectric potential and blood pressure measured by the vital signs sensor 121. This will be referred to as a "vital signs information image" here. In the graph of the vital signs information image, the horizontal axis is the passage of time, and the vertical axis is hectopascals (HPa) which is a display unit of blood pressure, and also microvolts (μV) which is a display unit of cardioelectric potential. The graph is composited as a two-dimensional image. The other additional image is MRI image information recorded before the surgery, and is a 3D image generated by computer graphics (CG, the image is hereinafter referred to as a "CG image"). The MRI image storage unit 122 stores image information for CG images including 3D information such as polygon data, for example.

The 3D image compositing unit 123 decides a range for display of the CG image and a viewpoint of the CG image, based on information recorded in the MRI image storage unit 122, and thus can generate a 3D CG image from this viewpoint. In the second embodiment, the vital signs information image is displayed as a planar image situated at a position floating above the display plane by 2 cm. The CG image is displayed at a depth position where the display plane is the center-of-gravity of a 3D object. The images are generated such that the depth distance of 3D objects generated by CG is constant. For example, the depth distance is a position 3 cm on the far side of the display plane through a position 3 cm on the near side of the display plate, for a total of 6 cm.

Figure 9:
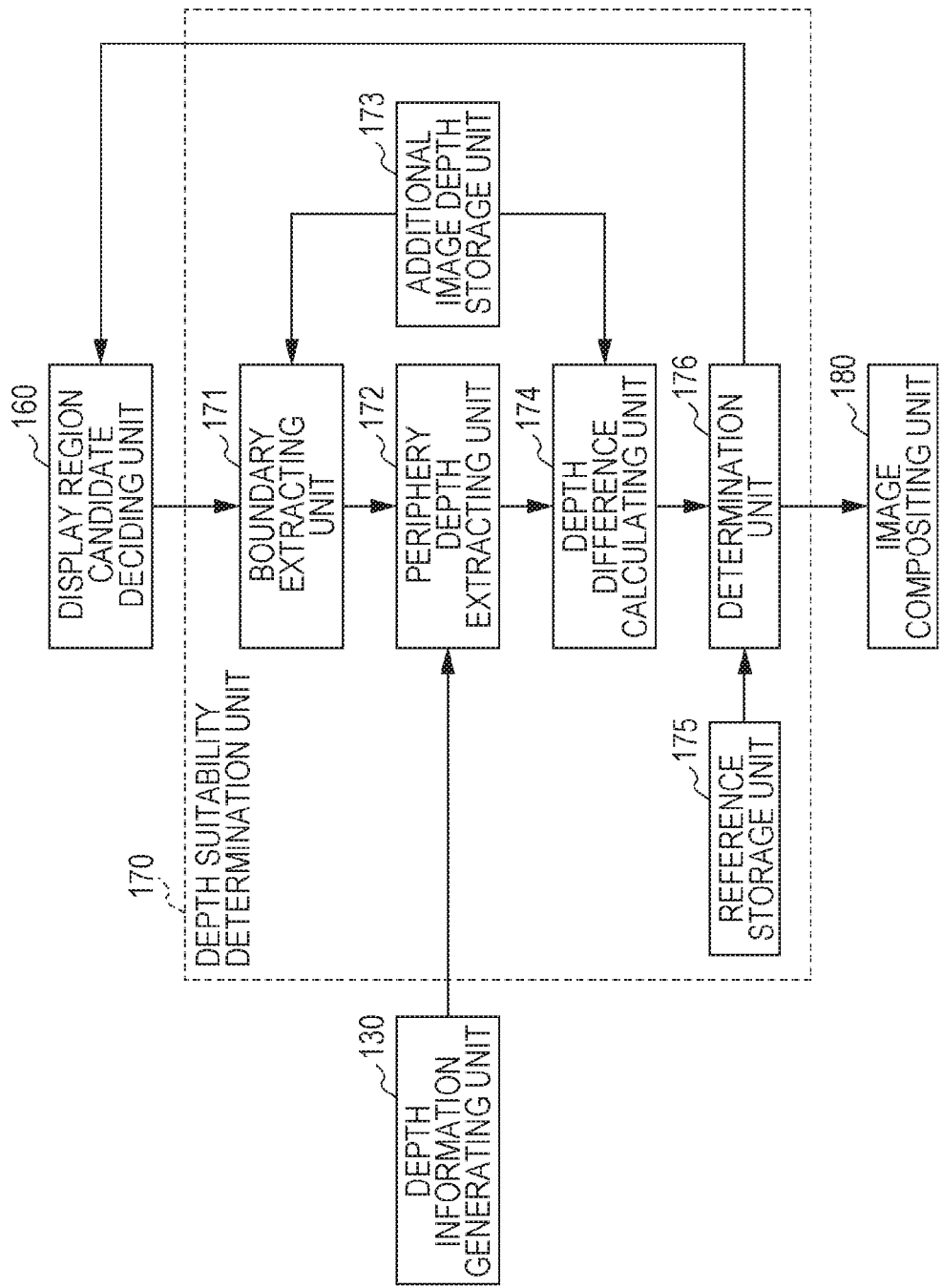
FIG. 9 is a block diagram illustrating a detailed functional configuration of part of the 3D display device according to the second embodiment.

FIG. 9 is a block diagram illustrating a detailed partial configuration of the 3D display device 20 according to the second embodiment. The depth suitability determination unit 170 includes a boundary extracting unit 171, a periphery depth extracting unit 172, an additional image depth storage unit 173, a depth difference calculating unit 174, a reference storage unit 175, and a determination unit 176.

The boundary extracting unit 171 obtains the boundary plane between the main image and the display region of each additional image, based on the display region of additional images which the display region candidate deciding unit 160 has decided in step S1200 and depth information of the additional images stored in the additional image depth storage unit 173. For example, in a case where the four sides of a rectangular additional image are parallel to the four sides of the display, the boundary plane is obtained as an x-z plane and a y-z plane on the coordinates system illustrated in FIG. 2B. In a case where the additional image is not rectangular with four sides parallel to the four sides of the display, the boundary plane is a plane parallel to the z-axis.

The periphery depth extracting unit 172 extracts depth information of the main image at the periphery of the boundary plane, from the depth information of the main generated by the depth information generating unit 130, and the information of the boundary plane which the boundary extracting unit 171 has obtained. Further, the periphery depth extracting unit 172 extracts depth information of the additional images at the periphery of the boundary planes from the depth information of each additional image stored in the additional image storage unit 173.

The depth difference calculating unit 174 calculates the difference between the depth of the main image and the depth of the additional image at each boundary plane, with regard to the depth of the main image and the depth of the additional images at the periphery of the boundary plane of the additional image regions extracted by the periphery depth extracting unit 172. The difference in depth is calculated as follows, for example. With regard to each of the main image side and additional image side across a single boundary plane, the depth difference calculating unit 174 obtains one or more contact positions between the boundary plane and an in-image object, or a plane of an image in a case of a 2D image. The depth difference calculating unit 174 extracts the z-axial coordinate value for each of the main image side and the additional image side at the contact position. The depth difference calculating unit 174 extracts the largest value of the z-axial coordinate value at the contact position for each of the main image side and additional image side. The depth difference calculating unit 174 then calculates a value obtained by subtracting the largest value at the main image side from the largest value at the additional image side as the difference in depth. In a case where each region has multiple boundary planes, the depth difference calculating unit 174 outputs the largest value in difference in depth to the determination unit 176 as the difference in depth at the region.

While the difference in depth has been decided here based on the largest value of z-axial coordinate values of the contact position with the boundary plane, other values may be used, such as the average value of z-axial coordinate values, or the like. While the difference in depth has been obtained here from coordinate values at the contact position with the boundary plane, an arrangement may be made where a 3D coordinate region including the boundary plane is set, and difference in depth is calculated based on the z-axial coordinate values of points making up objects in the coordinate region. The largest value or average value on the z-axis, and so forth, may be used for coordinates objects within the coordinate region as well.

The reference storage unit 175 stores the tolerance range for difference in depth that has been determined beforehand. The determination unit 176 compares the difference in depth across the boundary plane that has been calculated by the depth difference calculating unit 174 with the tolerance range stored in the reference storage unit 175, and determines whether or not the difference in depth between images on the inside and the outside of the boundary of the additional image display region exceeds the tolerance range.

Description of Step S1200

Figure 10A:
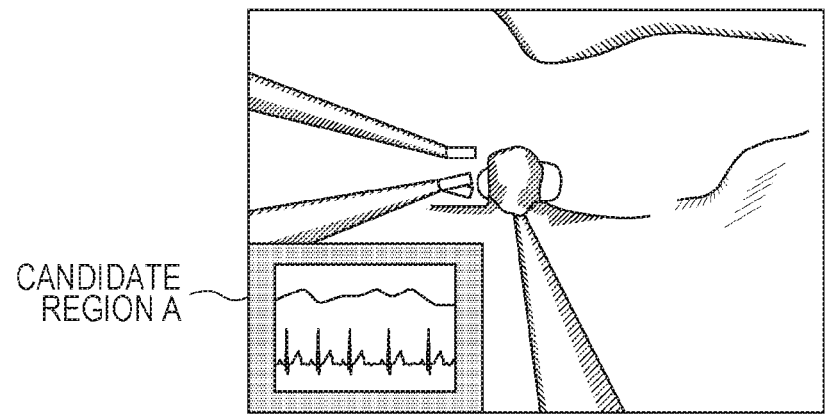
FIG. 10A is a schematic diagram illustrating an example of a display position of an additional image according to the second embodiment.
Figure 10B:
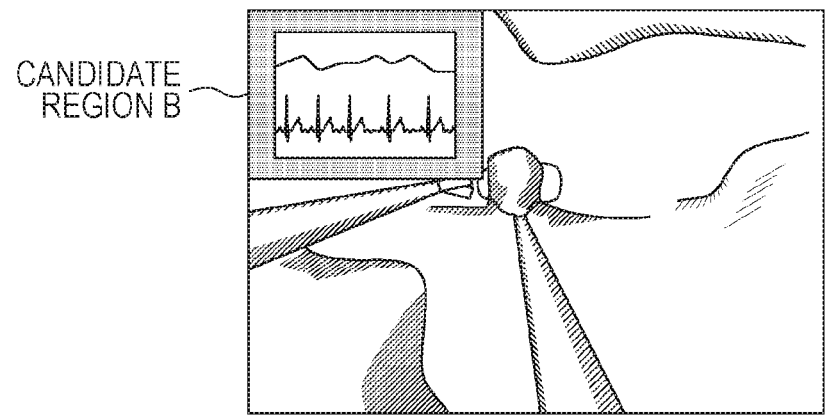
FIG. 10B is a schematic diagram illustrating an example of a display position of an additional image according to the second embodiment.
Figure 10C:
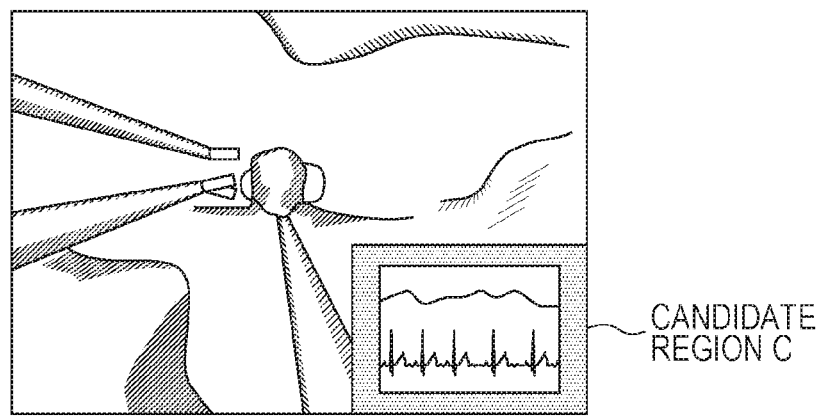
FIG. 10C is a schematic diagram illustrating an example of a display position of an additional image according to the second embodiment.
Figure 10D:
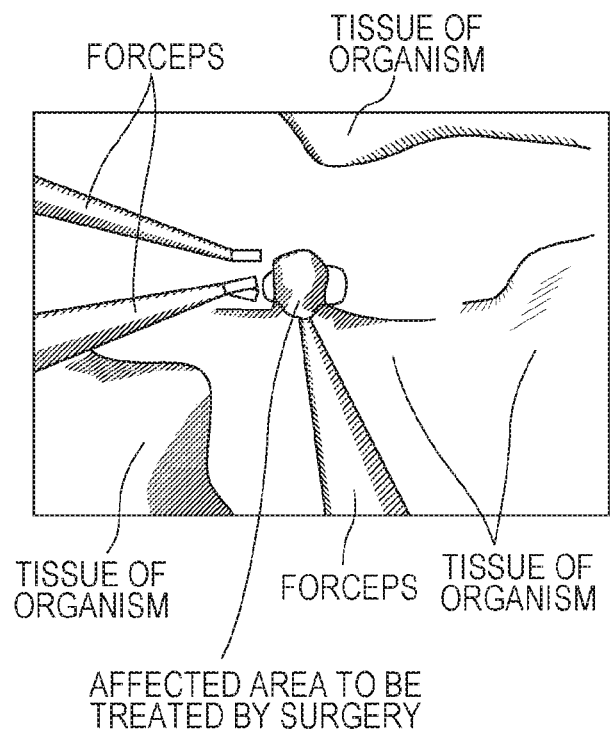
FIG. 10D is a schematic diagram illustrating an example of a main image according to the second embodiment.

FIGS. 10A through 10C illustrate examples of display region candidates which the display region candidate deciding unit 160 decides. FIG. 10D is an example of an image acquired by the stereo endoscope camera 111, which is the main image. FIG. 10A illustrates an example of a candidate region A, FIG. 10B illustrates an example of a candidate region B, and FIG. 10C illustrates an example of a candidate region C. The display region candidate deciding unit 160 decides the three candidate regions, candidate region A, candidate region B, and candidate region C. The number of candidate regions may be any number of one or more. In step S1200, the display region candidate deciding unit 160 decides display region candidates. Position information of the candidate regions is stored in the additional image position storage unit 140.

Operations of Depth Information Generating Unit 130 and Periphery Depth Extracting Unit 172: Details of Step S1300

In step S1300 the depth suitability determination unit 170 extracts a boundary line or boundary plane of a display region candidate of an additional image decided in step S1200, and extracts depth information. The periphery depth extracting unit 172 extracts depth information of the main image at the periphery of the boundary plane from the depth information of the main image generated by the depth information generating unit 130 and the boundary plane information obtained by the boundary extracting unit 171, in order to extract depth information of the boundary plane.

Figure 11A:
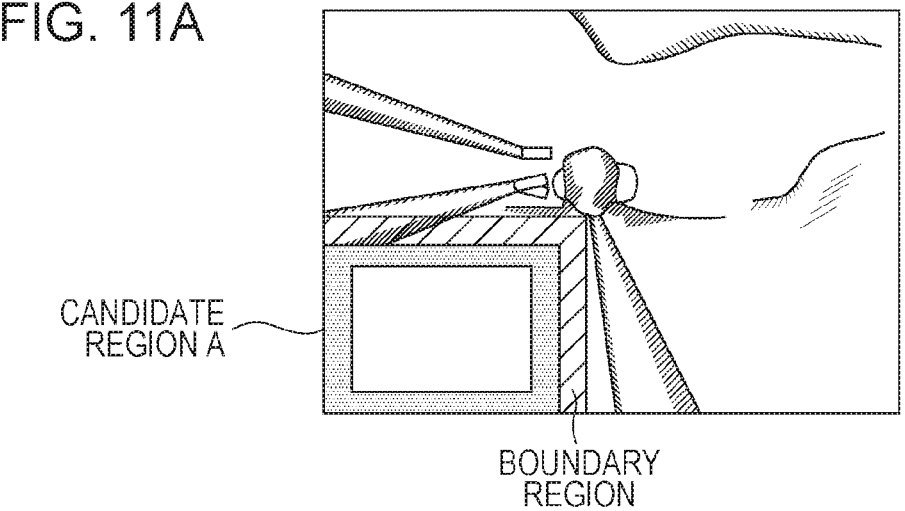
FIG. 11A is a schematic diagram illustrating an example of an additional image and a boundary region according to the second embodiment.
Figure 11B:
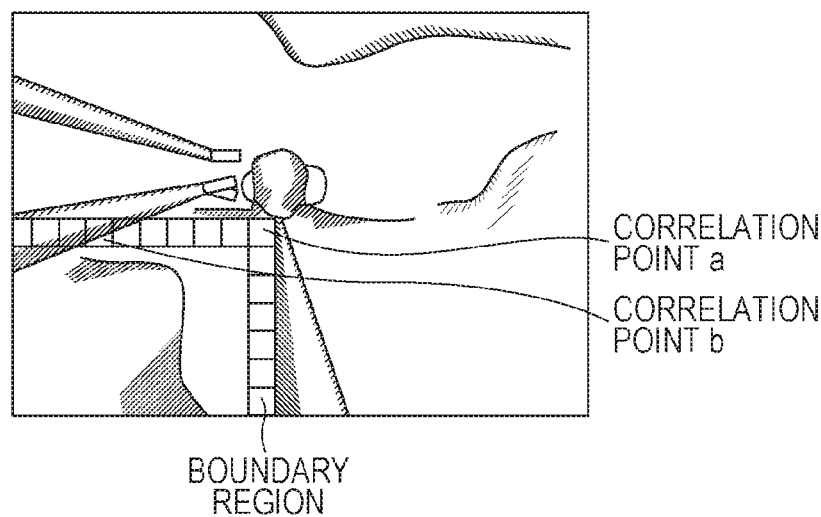
FIG. 11B is a schematic diagram illustrating an example of a display position of an addition image for a left-eye image according to the second embodiment.
Figure 11C:
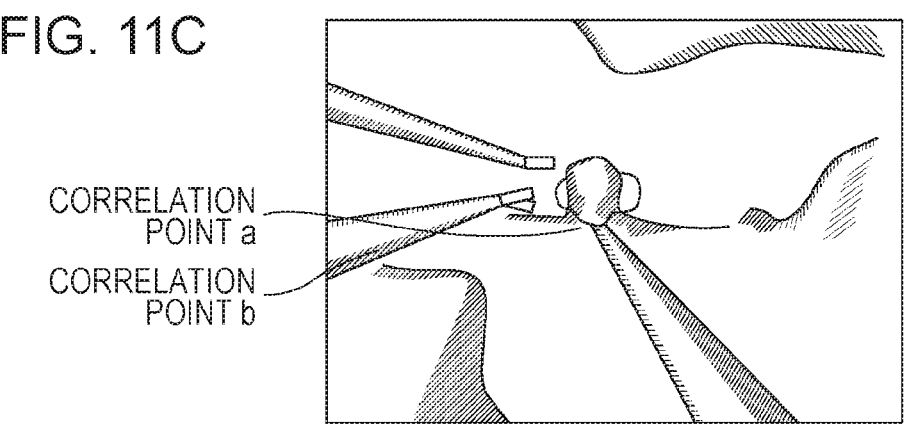
FIG. 11C is a schematic diagram illustrating an example of a right-eye image according to the second embodiment.

FIG. 11A is a schematic diagram illustrating boundary plane periphery portion of the candidate region A illustrated in FIG. 10A. FIG. 11B is a left-eye image of FIG. 11A, and FIG. 11C is a right-eye image of FIG. 11A. FIG. 11B illustrates divided regions obtained by dividing the boundary region in FIG. 11A.

The depth information generating unit 130 extracts correlation points in the left-eye image and the right-eye image. It is sufficient for the extraction of correlation points to be performed between steps S1100 and S1300. The correlation points are obtained by extracting the edges of each of the left-eye image and right-eye image, for example, and finding correlation from the positions and shapes of edges extracted in the left and right images. Also, an arrangement may be made where color regions of the left and right images are obtained, and the correlation points are found by finding correlation in the color regions.

A correlation point a and correlation point b in FIGS. 11B and 11C are examples of correlation points in the left-eye image and right-eye image. The correlation point a is a similar positions on the screen in both left and right images, while the position of the correlation point b on the screen differs among the left and right images. The depth information generating unit 130 generates disparity at the left and right correlation points rendered on the screen, i.e., offset information regarding the horizontal position in the left and right images. The periphery depth extracting unit 172 extracts correlation points in the boundary region in of one of the left and right images. The correlation points in the boundary region in the left-eye image are extracted in this example.

The periphery depth extracting unit 172 obtains the difference in horizontal position between a certain point within the boundary region of the left-eye image and a point in the right-eye image which corresponds to that point. The difference in horizontal position is represented as difference in X-coordinate on an x-y plane in a coordinate system such as illustrated in FIG. 2B, for example. A value obtained by subtracting the value of the x-coordinate on the left-eye image from the value of the x-coordinate on the right-eye image is taken as the offset in horizontal position, i.e., the disparity. In this case, the point appears deeper than the plane of the screen of the disparity is positive, and the point appears nearer than the plane of the screen of the disparity is negative.

Figures 12A, 12B:
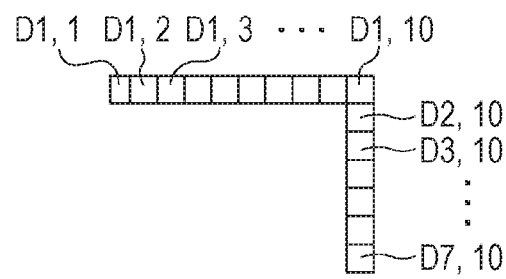
FIG. 12A schematic diagram illustrating an example of IDs given to partial regions of a boundary region of an additional image according to the second embodiment.
FIG. 12B is a diagram illustrating an example of disparity information at a boundary region according to the second embodiment.

FIG. 12A is a schematic diagram illustrating a boundary region set on a left-eye image. The boundary region is divided into partial regions, and an ID is set for each divided region. IDs of D1,1 through D7,10 are illustrated in the example in FIG. 12A.

FIG. 12B illustrates an example of disparity for each divided region which the periphery depth extracting unit 172 has obtained from the correlation points extracted from within the boundary region in the left-eye image. The periphery depth extracting unit 172 outputs information such as in FIG. 12B, for example, to the depth difference calculating unit 174.

With regard to the depth of the main image and depth of the additional image at the boundary plane periphery of the additional image region which the periphery depth extracting unit 172 has extracted, the depth difference calculating unit 174 calculates the difference in depth of the main image and depth of the additional image for each boundary plane. For example, for the boundary region of D1,1 through D1,10 in FIG. 12A, the depth is obtained from the largest disparity from D1,1 through D1,10 which is a partial boundary region making up the x-z plane of the boundary between the additional image and main image. The depth difference calculating unit 174 takes the difference between the depth of the boundary region which has been obtained and the depth of the additional image as the difference in depth of the x-z boundary plane of the candidate region A of the additional image. The depth difference calculating unit 174 performs similar calculations regarding the region from D1,10 through D7,10 to calculate the difference in depth of the y-z boundary plane of the candidate region A. While description has been made here of calculating the depth of the boundary region from the greatest disparity of the boundary region making up the boundary plane, the average disparity of the boundary region making up the boundary plane, or the like, may be used instead.

Advantages and Effects

According to the second embodiment described above, at the time of displaying an additional image over or adjacent to a 3D image from a stereo endoscope, the 3D display device 20 decides the display region of the additional image avoiding states with great difference in depth between the inside and outside of the boundary of the display region of the additional image, and states with depth contradiction. In 3D images for endoscope surgery using a stereo endoscope in particular, the affected area to be treated by surgery is displayed around the middle of the screen, while the arms of forceps are often displayed at the periphery portion of the screen. The forceps are often inserted toward the affected area from the same direction as the stereo endoscope, and thus the arms thereof are imaged as slender objects extending in the depth direction. Displaying the additional image of which the depth is close to that of the plane of the display, so as to overlap the image of the forceps greatly protruding toward in the near side of the screen, results in an additional image which appears to have embedded itself in the arms of the forceps. The above-described arrangement can avoid such depth contradiction and alleviate fatigue of the user, i.e., the surgeon.

Description has been made regarding the second embodiment that the display region candidate deciding unit 160 decides display region candidates not including the additional image display-forbidden region stored in the display-forbidden region storage unit 210, and the depth suitability determination unit 170 does not use information of the display-forbidden region. However, an arrangement may be made where the depth suitability determination unit 170 acquires distance indices of the distance from the display-forbidden region for each display region candidate, and gives display region candidates farther away from the display-forbidden region priority as processing regions.

Figures 13A, 13B:
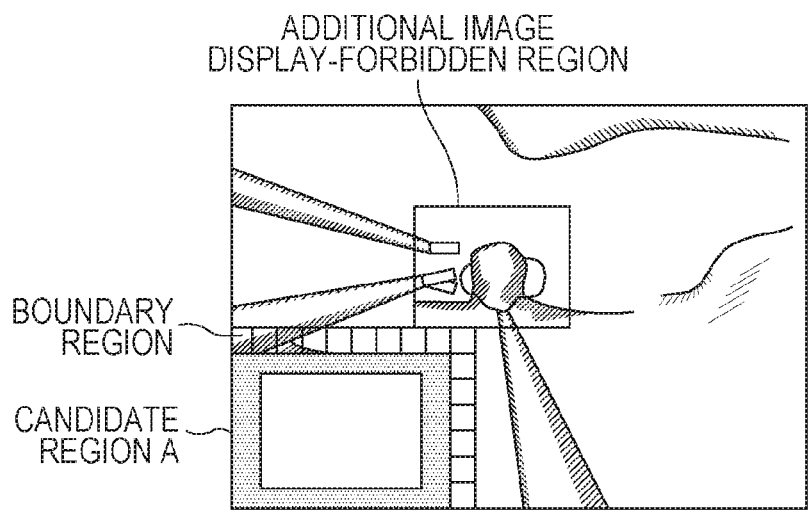
FIG. 13A is a schematic diagram illustrating an example of a display region of an additional image, an additional image display-forbidden region, and a boundary region, according to the second embodiment.
FIG. 13B illustrates an example of information of difference in depth for a display region of an additional image including information of distance from a display-forbidden candidate region according to the second embodiment.

FIG. 13A is a schematic diagram illustrating a candidate region A, a boundary region, and an additional image display-forbidden region, on the main image. FIG. 13B illustrates an example of information regarding difference in depth for each candidate region which the display region candidate deciding unit 160 outputs to the depth suitability determination unit 170, and information of distance from the forbidden region. Information regarding the distance from the forbidden region, and information of difference in depth between the main image and additional image in the periphery of the boundary, is included for each candidate region illustrated in FIGS. 10A through 10C.

In the example in FIG. 13B, first, the candidate region C is smaller than −1 cm, which is the lower limit for the tolerance range in difference in depth, so this is not selected as a display region for the additional image. Comparing the candidate region A and the candidate region B shows that the difference in depth is smaller at the candidate region B and thus the candidate region B is more suitable as a display region of the additional image, when the difference in depth alone is taken into consideration. However, the distance from the additional image display-forbidden region is smaller for the candidate region B as compared to the candidate region A.

This can be dealt with by using corrected values, for example, where 5 is added to the difference in depth for a range of up to 50 pixels from the additional image display-forbidden region, 3 is added for up to 75 pixels, 2 is added to up to 100 pixels, and 1 is added to up to 200 pixels. After 200 pixels, there is no correction by addition. Applying such corrected values to the example in FIG. 13B gives 11 for the difference in depth of the candidate region B since 5 has been added to the difference in depth 6, and gives 9 for the difference in depth of the candidate region A since 2 has been added to the difference in depth 7. In this case, the depth suitability determination unit 170 will select the candidate region A as the optimal region to serve as the display region for the additional image. Note that values for correcting difference in depth based on distance from the additional image display-forbidden region, and the method of correction, are not restricted to the above-described, and other methods may be used as well.

Description has been made regarding the second embodiment that the depth suitability determination unit 170 makes determination regarding whether or not the difference between the depth of the main image and the depth of the additional image at the periphery of the boundary plane of a candidate region for an additional image display region is within the tolerance range. However, an arrangement may be made for cases where the difference in depth only slightly exceeds the tolerance range, by providing a frame wider than normal for the display region of the additional image, so as to provide a buffer region regarding the difference in depth, and determining the difference in depth with the buffer region as a region where the additional image can be displayed. The term "slightly exceeds the tolerance range" means a case where, for example, the amount of difference in depth exceeding the tolerance range, i.e., the difference between the difference in depth and the tolerance range, is a predetermined value or smaller.

Figure 14A:
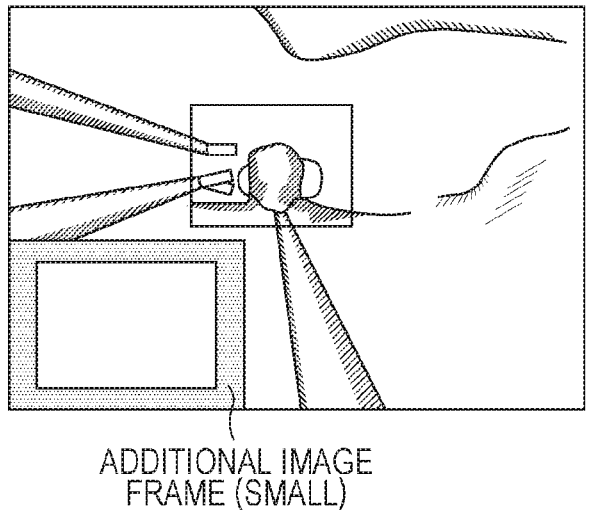
FIG. 14A is a schematic diagram illustrating an example of a small frame of an additional image according to the second embodiment.
Figure 14B:
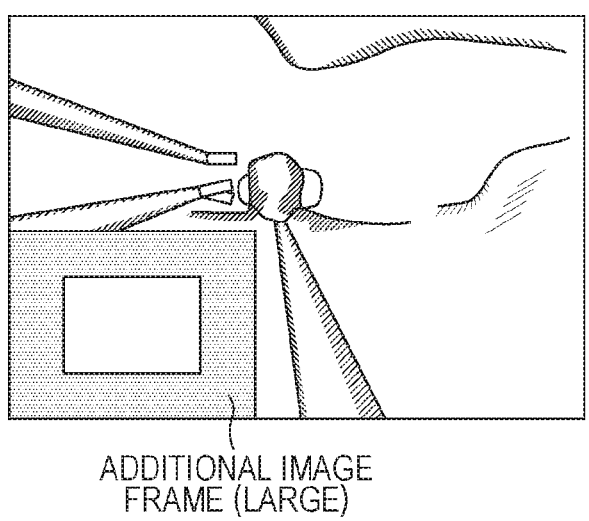
FIG. 14B is a schematic diagram illustrating an example of a large frame of an additional image according to the second embodiment.

FIG. 14A illustrates an additional image in a case where the depth suitability determination unit 170 has determined that the difference between the depth of the main image and the depth of the additional image at the periphery of the boundary plane of an additional image display region is within the tolerance range. The frame of this additional image is narrow. FIG. 14B illustrates an additional image in a case where the depth suitability determination unit 170 has determined that the difference between the depth of the main image and the depth of the additional image at the periphery of the boundary plane of an additional image display region is not within the tolerance range, and a buffer region is necessary. The frame of this additional image is broad, serving as a buffer region regarding the difference in depth between the inside and outside of the frame.

One way to set a broader frame is to reduce the display size of the additional image without changing the region in the main image which is shielded. If the region of the main image which is shielded can be enlarged, the frame can be made broader without changing the size of the additional image. FIG. 14B illustrates a case where the additional image is reduced in size and also the shielded region is enlarged.

First Modification of Second Embodiment

The endoscope camera 111 in the 3D display device 20 according to the second embodiment does not change the imaging position, and does not change the distance between the endoscope camera 111 and the affected area, i.e., does not zoom in or zoom out. A case of changing the distance between the endoscope camera 111 and the affected area will be described in the present modification.

In a case of the endoscope camera 111 changing the distance as to the affected area, the depth information of the 3D image changes. The region is centered on the affected area where shielding by the additional image is forbidden, also grows and shrinks accordingly. Accordingly, the display region of the additional image also needs to change. Description will be made in the first modification of the second embodiment regarding a method of calculating the distance from the camera to the affected area from images acquired by the endoscope camera 111, decoding the additional image display-forbidden region according to the distance, and deciding the additional image display region.

FIG. 15 is a block diagram illustrating a functional configuration of the 3D display device 20 according to the first modification of the second embodiment. The configuration is the same as the 3D display device 20 according to the second embodiment illustrated in FIG. 7, other than the display-forbidden region storage unit 210 has been replaced by a display-forbidden region storage unit 211, and a forbidden region deciding unit 212 has been added. Portions which are the same as those in FIG. 7 are denoted by the same reference numerals, and description will be omitted.

Configuration

The 3D display device 20 includes the endoscope camera 111, vital signs sensor 121, MRI image storage unit 122, 3D image compositing unit 123, depth information generating unit 130, additional image position storage unit 140, additional image size storage unit 150, display region candidate deciding unit 160, depth suitability determination unit 170, image compositing unit 180, display 190, display-forbidden region storage unit 211, forbidden region deciding unit 212, and input unit 200.

The display-forbidden region storage unit 211 stores a region to forbid display of an additional image. The forbidden region is around the middle of the screen. The affected area which is to be treated by surgery is shown around the middle of the screen, so in a case where the endoscope camera 111 draws closer to the affected area, a relatively wide range of the screen is an image of around the affected area, so the display-forbidden region of the additional image becomes larger. On the other hand, in a case where the endoscope camera 111 is distanced from the affected area, only a relatively narrow range at the center portion of the screen is an image of around the affected area, so the display-forbidden region of the additional image becomes smaller. The display-forbidden region storage unit 211 stores an additional image display-forbidden region corresponding to the distance between the endoscope camera 111 and the object at the center of the screen.

FIG. 16 illustrates an example of the contents stored in the display-forbidden region storage unit 211. The display-forbidden region storage unit 211 stores ranges of distance between the endoscope camera 111 and an object at the center of the screen, and additional image display-forbidden regions corresponding to the distance ranges. The regions are represented as 3D image coordinates, such as in FIG. 2B. The display-forbidden region is represented as a region on an x-y plane, and the value of the z axis is optional. A cylindrical region orthogonal to the display plane is the display-forbidden region.

The forbidden region deciding unit 212 obtains the distance between the endoscope camera 111 and the object at the center of the screen following the depth information of the main image output from the depth information generating unit 130. The forbidden region deciding unit 212 extracts a display-forbidden region corresponding to the distance between the endoscope camera 111 and the object at the center of the screen, from the information stored in the display-forbidden region storage unit 211, and decides the display-forbidden region of the additional image. The display region of the additional image can thus be decided, in accordance with change in the region where shielding by the additional image is forbidden due to zoom in and zoom out operations of the endoscope camera 111.

Figure 17:
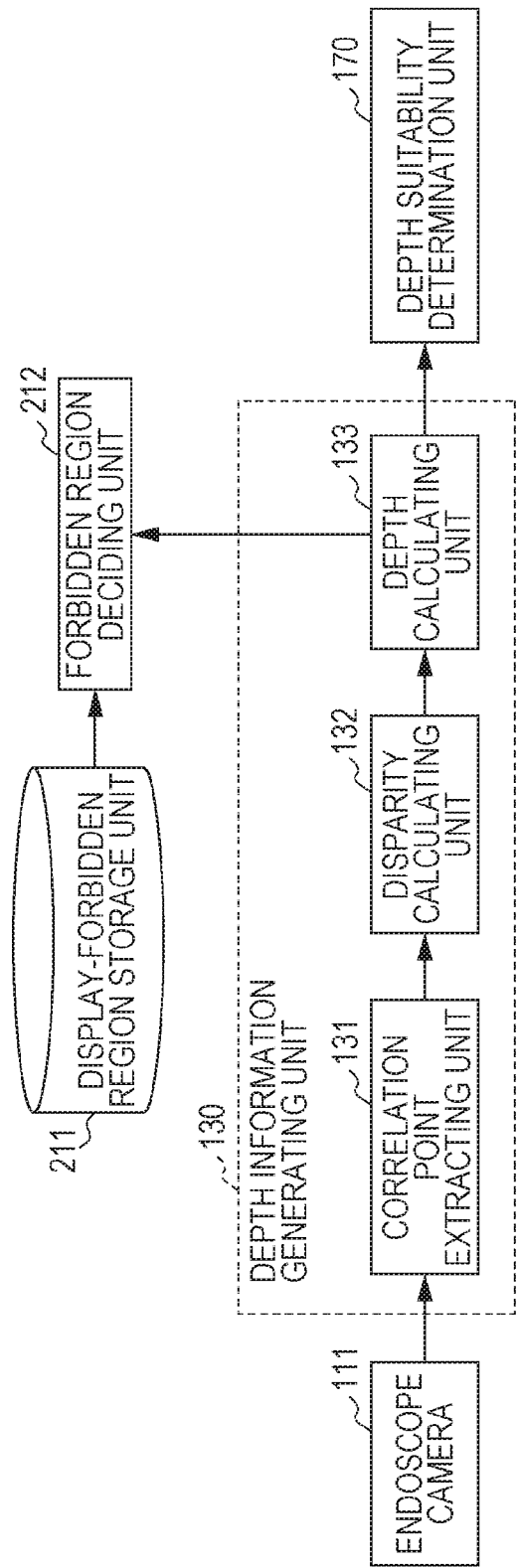
FIG. 17 is a block diagram illustrating a detailed functional configuration of a part of the 3D display device according to the first modification of the second embodiment.

The following is a detailed description of the depth information generating unit 130 and of a method for calculating the distance to an object at the center of the screen. FIG. 17 is a block diagram illustrating the details of part of the 3D display device 20 according to the first modification of the second embodiment.

The depth information generating unit 130 includes a correlation point extracting unit 131, a disparity calculating unit 132, and a depth calculating unit 133.

The correlation point extracting unit 131 obtains correlation points in a right-eye image left-eye image, from a stereo 3D image acquired at the endoscope camera 111. That is to say, points are extracted in the right-eye image and the left-eye image which have been taken of the same point in the same subject. Examples of correlation point extraction include a correlation method where correlation points are detected from the correlation in luminance distribution of the left and right images, and a method of obtaining correlation points by performing edge extraction on the left and right images, for example.

The disparity calculating unit 132 extracts the position in the right-eye image and the position in the left-eye image for each correlation point extracted by the correlation point extracting unit 131, and obtains the difference in the horizontal direction between the left and right images. For example, the correlation points in the left and right images are illustrated following x-y plane coordinates where the horizontal direction on the display plane is the x axis, the vertical direction in the y axis, the right direction is the positive on the x axis of coordinate axes having the center-of-gravity point of the display as the origin, the left direction is negative on the x axis, the upward direction is positive on the y axis, and the downward direction is negative on the y axis. A value obtained by subtracting the x coordinate value of the left-eye image from the x coordinate value of the right-eye image is the calculated disparity. If the object is situated on the display plane, the disparity is zero, and if the object is situated nearer to the viewer from the display plane, the disparity is a negative value. If the object is situated on the far side of the display plane from the viewer, the disparity is a positive value.

The depth calculating unit 133 calculates the distance between the endoscope camera 111 when imaging the object, and the depth position of the object in the image when displaying the object, based on the disparity which the disparity calculating unit 132 has calculated. The depth calculating unit 133 outputs the distance between the endoscope camera 111 and the object at the time of imaging to the forbidden region deciding unit 212, and outputs the depth position of the object in the image at the time of displaying the image to the depth suitability determination unit 170.

While the distance between the endoscope camera 111 and the object at the center of the screen, which is the affected area, has been described in the first modification as being calculated using disparity of the stereo 3D image, an arrangement may be made where an object with unchanging size is determined in one or the other of the left and right images, and the distance between the endoscope camera 111 and the object at the center of the screen is obtained based on the size of this object in the image.

While the display-forbidden region storage unit 211 has been described in the first modification as storing a display-forbidden region corresponding to the distance between the endoscope camera 111 and the object, an arrangement may be made where the display-forbidden region storage unit 211 only stores a standard display-forbidden region, the same as with the display-forbidden region storage unit 210. In this case, the forbidden region deciding unit 212 may enlarge or reduce the size of the display-forbidden region stored in the display-forbidden region storage unit 211 based on the ratio between the distance from the endoscope camera 111 to the object and a standard distance.

Advantages

An additional image display-forbidden region corresponding to the distance between the camera and affected area is stored in the display-forbidden region storage unit 211, the distance between the camera and affected area is calculated from an image acquired at the endoscope camera 111, and a display-forbidden region for the additional image is selected according to that distance. Accordingly, even if the distance between the endoscope camera 111 and the affected area changes by the endoscope camera 111 zooming in or zooming out, and the region of the affected area and the periphery thereof in the image which should not be shielded during surgery changes, the main image and additional image can be displayed without the additional image shielding the affected area and the periphery.

Second Modification of Second Embodiment

While the second embodiment has been described as the depth of the additional image being fixed, the depth of the additional image changes depending on the content of display in the second modification. In a case where the depth of the additional image is fixed, in the second embodiment the depth suitability determination unit 170 extracts only the depth range of the main image regarding the depth of the boundary plane of the display region of the additional image and the periphery thereof, and compares with the depth of an additional image determined beforehand. However, in a case where the depth range of the additional image changes depending on the content of display as in the second modification, there is a need to calculate the depth range of the additional image and perform comparison.

Figure 18:
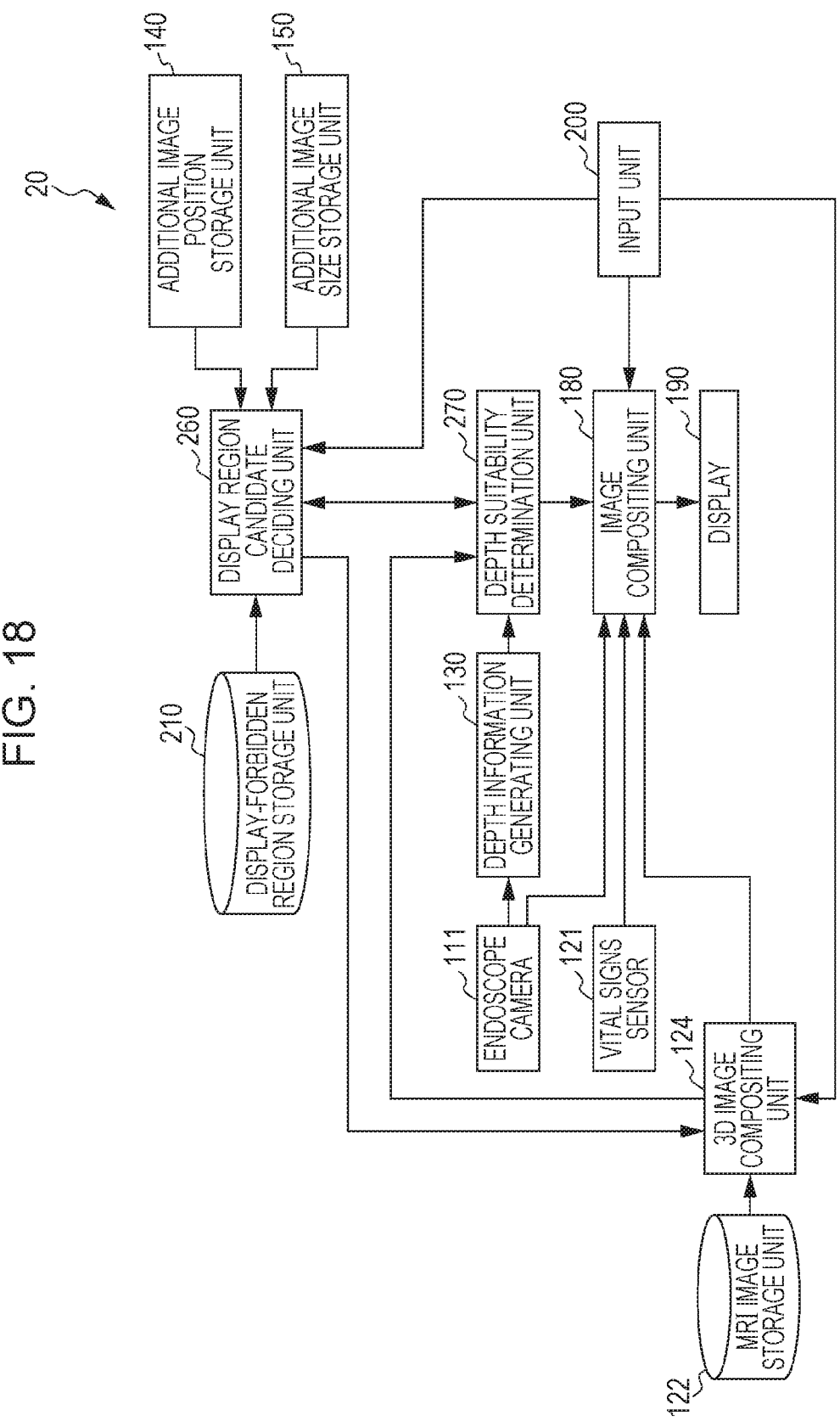
FIG. 18 is a block diagram illustrating a functional configuration of a 3D display device according to a second modification of the second embodiment.

FIG. 18 is a block diagram illustrating a function configuration of the 3D display device 20 according to the second modification of the second embodiment. The configuration is the same as the 3D display device 20 according to the second embodiment illustrated in FIG. 7, other than the points that the 3D image compositing unit 123 has been replaced by a 3D image compositing unit 124, the display region candidate deciding unit 160 has been replaced by a display region candidate deciding unit 260, and the depth suitability determination unit 170 has been replaced by a depth suitability determination unit 270. Portions which are the same as those in FIG. 7 are denoted by the same reference numerals, and description will be omitted.

Configuration

The 3D display device 20 includes the endoscope camera 111, vital signs sensor 121, MRI image storage unit 122, 3D image compositing unit 124, depth information generating unit 130, additional image position storage unit 140, additional image size storage unit 150, display region candidate deciding unit 260, depth suitability determination unit 270, image compositing unit 180, display 190, display-forbidden region storage unit 210, and input unit 200.

The display region candidate deciding unit 260 selects an additional image size from additional image size information stored in the additional image size storage unit 150, in accordance with additional image size specification information input at the input unit 200. The display region candidate deciding unit 260 also decides candidates for an additional image display region based on information of the additional image position stored in the additional image position storage unit 140 and the information of the additional image display-forbidden region stored in the display-forbidden region storage unit 210, and outputs information indicating a decided candidate to the depth suitability determination unit 270 and 3D image compositing unit 124.

The 3D image compositing unit 124 composites the image information stored in the MRI image storage unit 122 into an image which can be displayed in the additional image display region decided at the display region candidate deciding unit 260, based on instructions regarding display contents input from the input unit 200, such as for example display range, display scale, type of MRI image (whether 2D image or 3D image), and so forth. The 3D image compositing unit 124 further outputs depth information of the composited image to the depth suitability determination unit 270.

The depth suitability determination unit 270 extracts the boundary plane of the additional image display region based on information of the candidate of the display region decided by the display region candidate deciding unit 260, and extracts the depth of the main image at the periphery of the boundary plane from the depth information of the main image generated at the depth information generating unit 130. The depth suitability determination unit 270 further extracts depth information of the additional image at the periphery of the boundary plane from the depth information of the image which the 3D image compositing unit 124 has composited. The depth suitability determination unit 270 compares the difference in depth between the main image side and additional image side of the boundary plane of the additional image display region that has been extracted, and detects difference in depth exceeding a predetermined value or depth contradiction.

Figure 19:
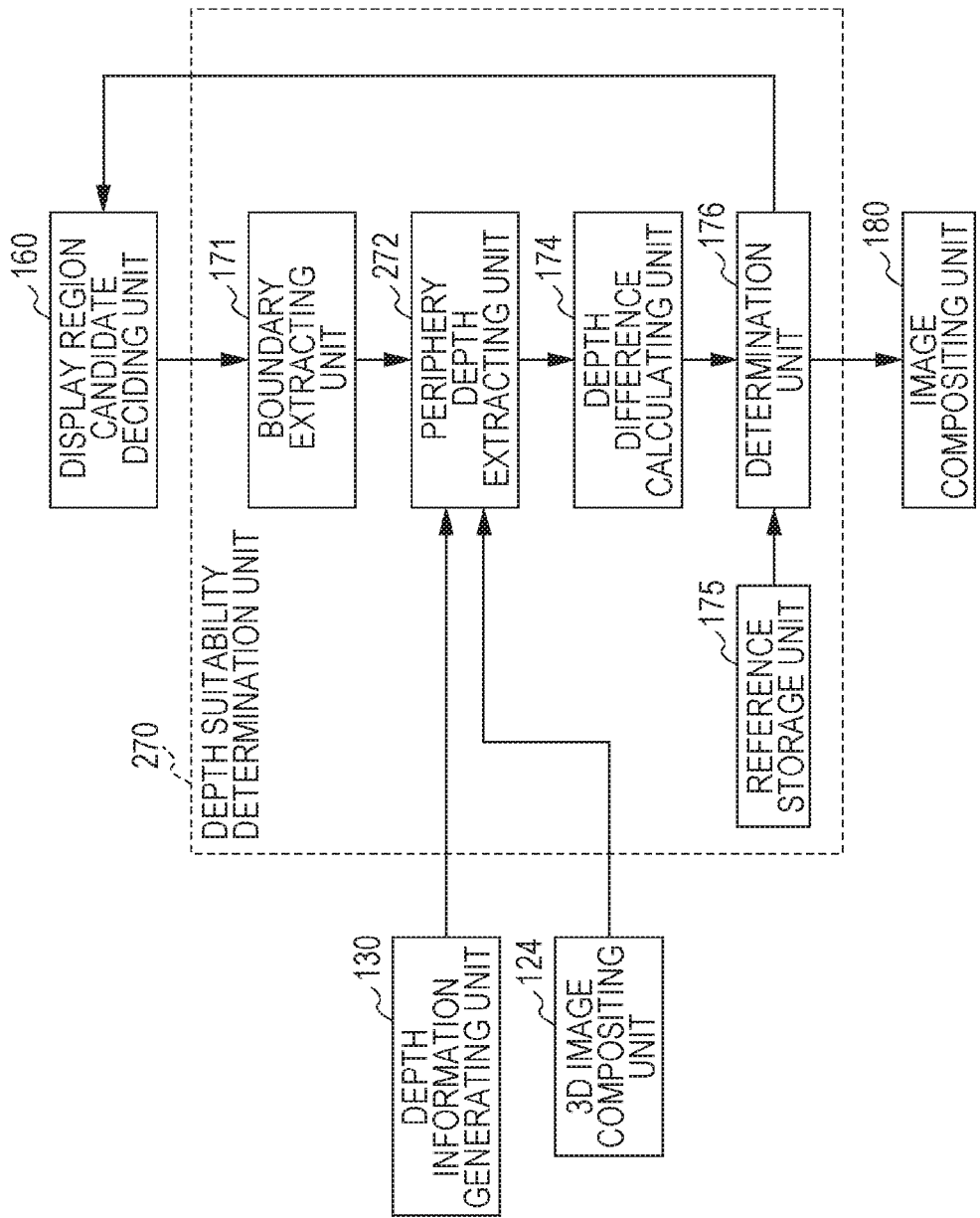
FIG. 19 is a block diagram illustrating a detailed functional configuration of a part of the 3D display device according to the second modification of the second embodiment.

FIG. 19 is a block diagram illustrating part of the 3D display device 20 according to the second modification of the second embodiment in detail. The configuration in FIG. 19 that in FIG. 9 according to the second embodiment, other than the points that the periphery depth extracting unit 172 has been replaced by a periphery depth extracting unit 272, and the additional image storage unit 173 has been omitted. Portions which are the same as those in FIG. 9 are denoted by the same reference numerals, and description will be omitted.

The depth suitability determination unit 270 includes the boundary extracting unit 171, periphery depth extracting unit 272, depth difference calculating unit 174, reference storage unit 175, and determination unit 176. The periphery depth extracting unit 272 extracts depth information of the main image at the boundary plane periphery from the depth information of the main image which the depth information generating unit 130 has generated, and the boundary plane information which the boundary extracting unit 171 has obtained. The periphery depth extracting unit 272 further extracts the depth information of the additional image at the boundary plane periphery from the depth information of the additional image generated by the 3D image compositing unit 124 and the boundary plane information obtained by the boundary extracting unit 171.

Figure 20A:
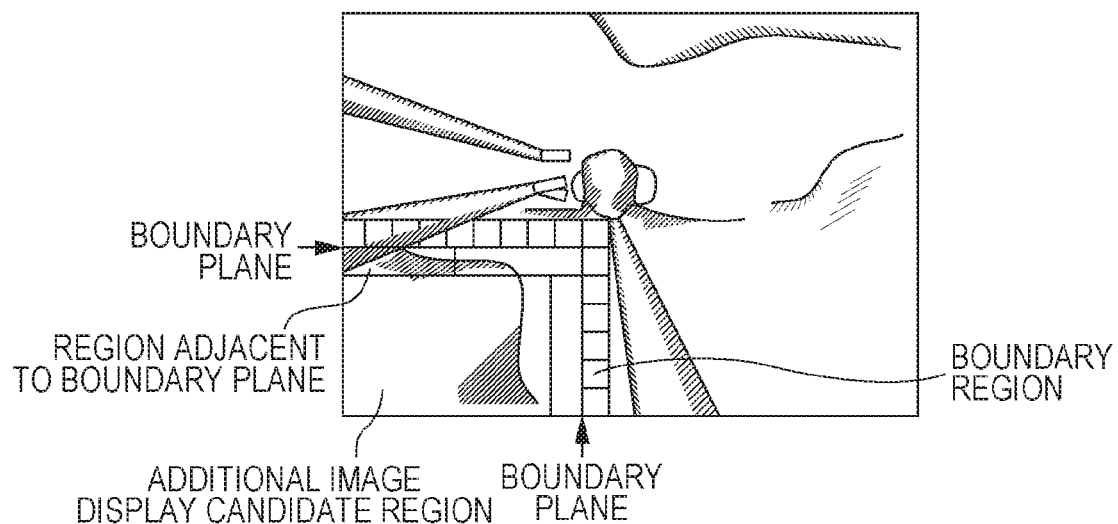
FIG. 20A is a schematic diagram illustrating an example of a boundary plane of a display region candidate for an additional image, a boundary region, and a boundary adjacent region, according to the second modification of the second embodiment.
Figure 20B:
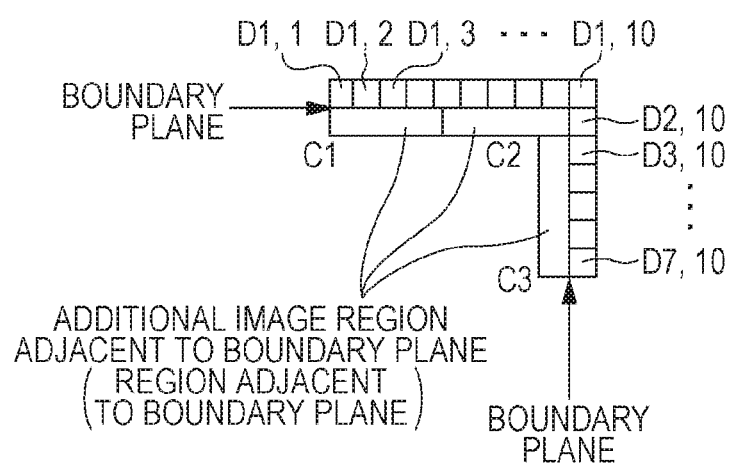
FIG. 20B illustrates an example of IDs given to partial regions of a boundary region and a boundary plane adjacent region according to the second embodiment.

FIG. 20A illustrates an additional image display candidate region, a boundary region on a main image which is a peripheral region of an additional image display region, and a boundary plane adjacent region which is an additional image side boundary plane peripheral region. FIG. 20B illustrates an example of each divided region and IDs thereof regarding the boundary region and boundary plane adjacent region in FIG. 20A.

The method for obtaining the depth of the boundary region is the same as with the second embodiment. A method for calculating depth information of the boundary plane adjacent region will now be described. The 3D image compositing unit 124 acquires information of the display region for the additional image display region candidate from the display region candidate deciding unit 260, and generates image information for displaying a computer graphics 3D image at the specified display region. The image information includes the correlation points for the left-eye image and right-eye image, and disparity information for the correlation points.

The periphery depth extracting unit 272 extracts a boundary within a predetermined distance from the boundary plane as to the main image as the boundary plane adjacent region, for one or the other of the left-eye image and right-eye image, as illustrated in FIG. 20A. The periphery depth extracting unit 272 further divides the boundary plane adjacent region into partial regions as illustrated in FIG. 20B, for example. In this case, the boundary plane adjacent region has been set on the left-eye image, and partial region (boundary region) C1 through partial region (boundary region) C3 have been set. Note that a boundary plane adjacent region and partial regions thereof may be set on the right-eye image. The periphery depth extracting unit 272 extracts the disparity between a point making up an object displayed within the boundary plane adjacent region and a correlation point on the right-eye image, from the image information which the 3D image compositing unit 124 has generated. The periphery depth extracting unit 272 obtains the greatest disparity value in disparity at each point of the object, for each partial region. While the greatest value is used here as a representative value of disparity in the partial regions, other statistical values may be used, such as average value or the like.

Note that the main image has a broad range of depth, and change in depth is marked. Accordingly, there are cases where difference in depth may be great between adjacent boundary regions. Reducing the size of the boundary regions enables the depth of the boundary regions to be calculated accurately. On the other hand, the additional image has a narrow range of depth, and change is gradual. Accordingly, the depth at the boundary plane adjacent region can be accurately calculated even if the size of the boundary plane adjacent regions is relatively large.

FIG. 21 is an example of information output from the periphery depth extracting unit 272. Along with the boundary region and boundary plane adjacent region, the largest value of disparity for each partial region is extracted as a representative value of disparity of the region. Based on disparity information such as illustrated in FIG. 21, the depth difference calculating unit 174 calculates the depth position of each region from the disparity of which the absolute value is the largest from boundary region D1,1 to D1,4, and the disparity of boundary plane adjacent region C1, and obtains the difference in depth between the boundary region which is at the main image side and the boundary plane adjacent region which is at the additional image side. In the same way, the depth difference calculating unit 174 obtains the difference in depth for each of boundary region D1,5 to D1,10, and boundary plane adjacent region C2, and boundary region D2,10 to D7,10, and boundary plane adjacent region C3.

Figure 22:
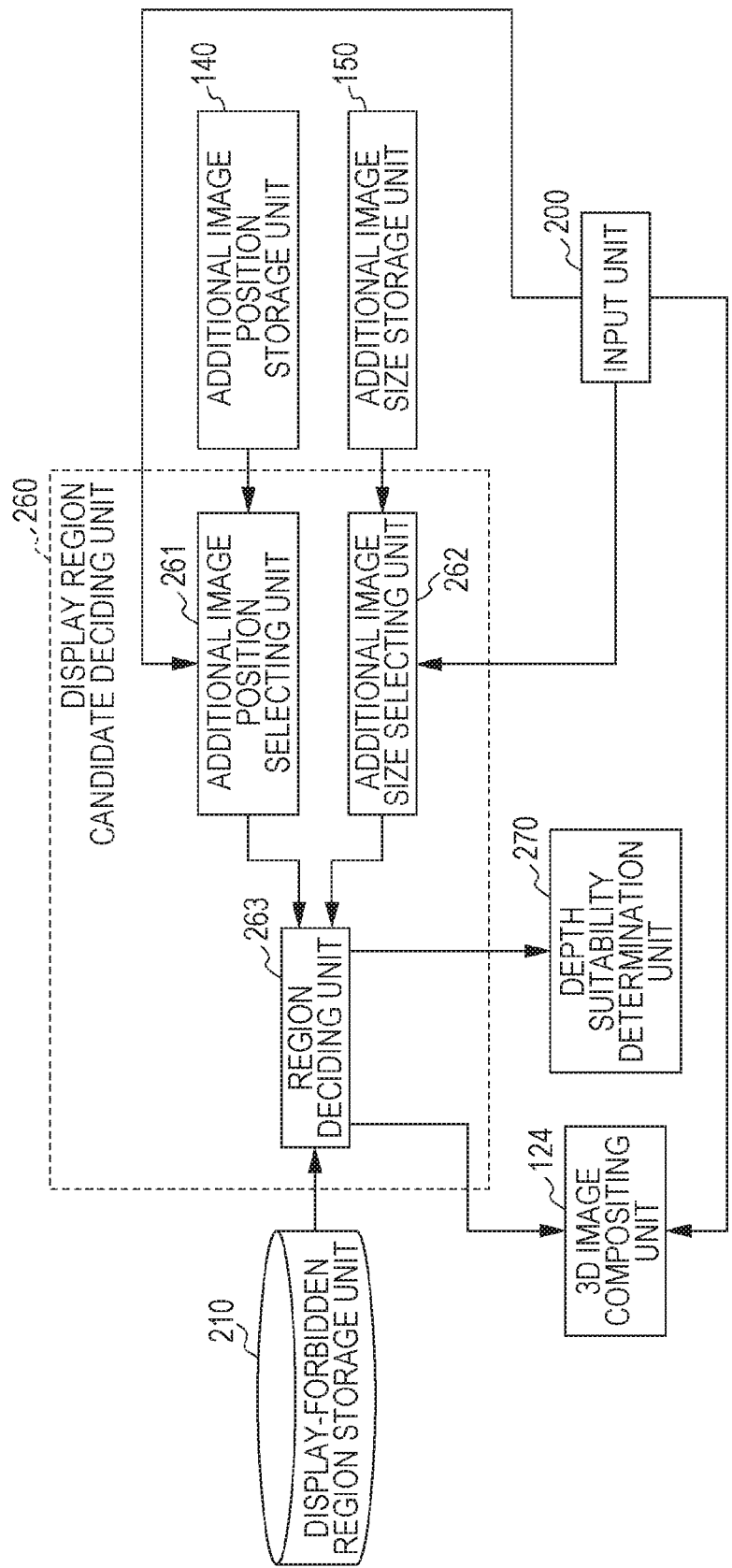
FIG. 22 is a block diagram illustrating a detailed functional configuration of a part of a 3D display device according to the second modification of the second embodiment.

FIG. 22 is a block diagram illustrating part of the 3D display device 20 according to the second modification of the second embodiment in detail. The display region candidate deciding unit 260 has an additional image position selecting unit 261, an additional image size selection unit 262 and a region deciding unit 263.

The additional image position selecting unit 261 selects information of additional image positions of a number specified by the input unit 200, from additional image position information stored in the additional image position storage unit 140.

The additional image size selecting unit 262 selects size information of the additional image from information stored in the additional image size storage unit 150, following the additional image size information specified at the input unit 200.

The region deciding unit 263 decides a candidate for a region to display the additional image, based on the additional image position selected by the additional image position selecting unit 261 and the additional image size selected at the additional image size selecting unit 262, and outputs this to the 3D image compositing unit 124 and the depth suitability determination unit 270.

Advantages

The display region candidate deciding unit 260 decides a candidate for an additional image region following additional image size information, out of display conditions for the additional image input at the input unit 200. On the other hand, the 3D image compositing unit 124 composites the additional image at the image size which the display region candidate deciding unit 260 has decided, following the display conditions for the additional image input at the input unit 200. The depth suitability determination unit 270 extracts main image side depth information for the boundary plane of the additional image display region from the depth information generating unit 130, and additional image side depth information from the 3D image compositing unit 124, and decides whether or not the difference in depth across the boundary plane of the display region is within a suitable range. Due to this configuration, even if the depth of an image displayed as an additional image changes due to user instructions, the display range of the additional image can be set so that the difference in depth across the boundary of the display region of the additional image does not exceed the suitable range.

Third Modification of Second Embodiment

While the display-forbidden region storage unit 213 according to the second embodiment only stores a predetermined forbidden region, the display-forbidden region storage unit 213 according to a third modification sets and stores a new display-forbidden region from an image imaged by the endoscope camera 111. In a case of endoscopic surgery, the endoscope camera and surgical tools are inserted into the body through multiple guide tubes. While the position and direction of the guide tubes differ from one surgery to another, the guide tubes hardly every move during surgery. Accordingly, while there may be differences such as whether a surgical instrument is inserted or not inserted during the surgery, but the positional relation between the camera and inserted surgical instrument, and the positional relation between the camera and the structure within the body does not change greatly. Accordingly, images are detected which have a depth such that there is a possibility that depth contradiction or excessively large depth difference will occur between the main image imaged by the endoscope camera 111 after surgery starts and the additional image which shields a part of the main image, and such detected images are stored as additional image display-forbidden regions. Thus, the search range for the additional image display region can be restricted, thereby reducing the load of the additional image display region deciding. Further, movement of the additional image display region can be reduced, so the display of the additional image stabilizes.

Figure 23:
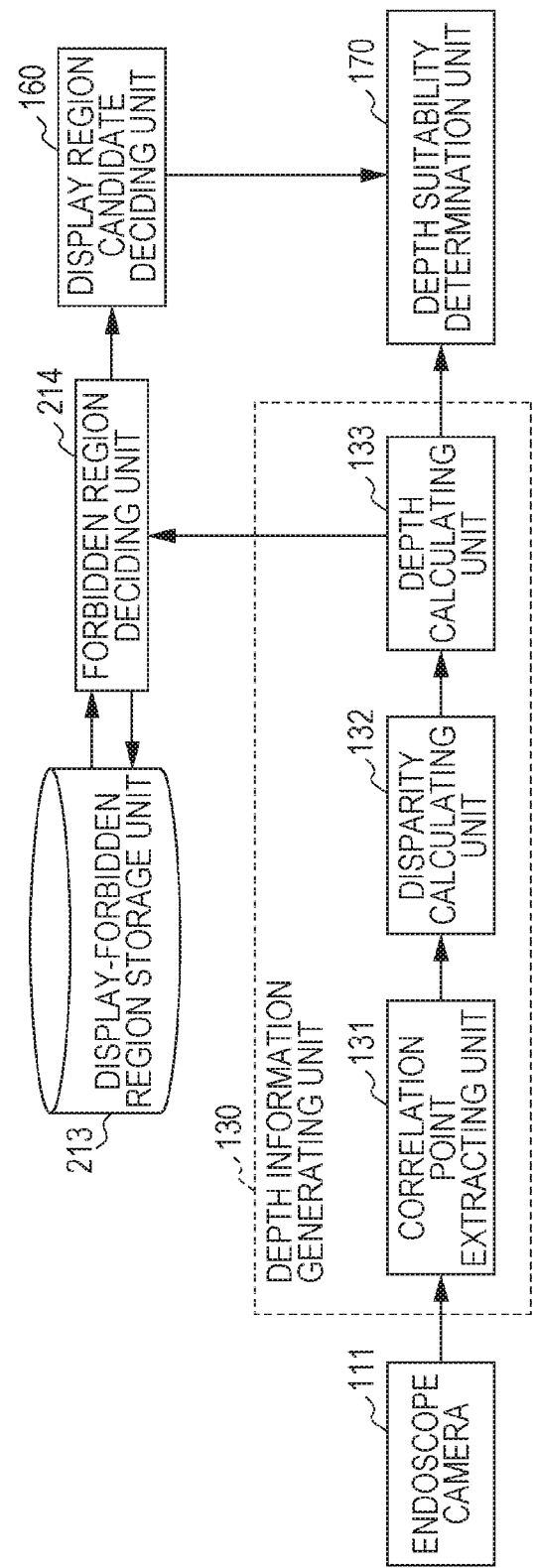
FIG. 23 is a block diagram illustrating a detailed functional configuration of a part of the 3D display device according to a third modification of the second embodiment.

FIG. 23 is a block diagram illustrating a part of the 3D display device 20 according to the third modification of the second embodiment in detail. The configuration in FIG. 23 is the same as the first modification of the second embodiment in FIG. 17, other than the points that the display-forbidden region storage unit 211 has been replaced by a display-forbidden region storage unit 213, and the forbidden region deciding unit 212 has been replaced by a forbidden region deciding unit 214. Portions which are the same as those in FIG. 17 are denoted by the same reference numerals, and description will be omitted.

The 3D display device 20 according to the third modification of the second embodiment is the same as that according to the first embodiment of the second embodiment in FIG. 15, other than the points that the display-forbidden region storage unit 211 has been replaced by a display-forbidden region storage unit 213, and the forbidden region deciding unit 212 has been replaced by a forbidden region deciding unit 214. Accordingly, description of the block diagram illustrating the functions of the 3D display device 20 will be omitted.

The display-forbidden region storage unit 213 stores information of regions to forbid display of additional images. That is to say, the display-forbidden region storage unit 213 stores, as information of regions to forbid display of additional images, the information of the region around the center of the screen that has been determined beforehand, and information of portions where depth is markedly great, i.e., portions deeply recessed, and where depth is markedly small, i.e., portions greatly protruding, detected from the image imaged by the endoscope camera 111.

The forbidden region deciding unit 214 extracts information of regions to forbid display of the additional images, stored in the display-forbidden region storage unit 213, and outputs to the display region candidate deciding unit 160. The forbidden region deciding unit 214 further decides a new forbidden region, based on information of a display region including depth information of an object or background imaged by the endoscope camera 111, that has been generated at the depth information generating unit 130, and outputs the decided forbidden region to the display-forbidden region storage unit 213.

Deciding of the new forbidden region is performed by the forbidden region deciding unit 214 as follows. In a case where a region which is recessed to the deep side beyond the predetermined depth range, or a region protruding to the near side beyond the predetermined depth range, are not included in the display-forbidden region stored in the display-forbidden region storage unit 213, this region is a new display-forbidden region. For example, in a case of imaging a tubular structure such as a digestive organ in the longitudinal direction, the main image will be an image looking through the tubular structure, so the recessed amount to the deep side will be extremely great. If the depth exceeds the maximum depth of the depth range for the additional image and is larger than a predetermined value, there is a possibility that the difference in depth between the additional image and the main image may be too great. Such a region is made to be an additional image display-forbidden region.

For example, in a case where the depth range of the additional image is −5 cm on the z axis in FIG. 2B, which is the far side of the display, to 5 cm on the z axis which is the near side of the display, an object or background at −20 cm or deeper on the z axis from the display may have difference in depth between the main image and additional image that exceeds 15 cm. Accordingly, that region is set to an additional image display-forbidden region. Also, an object such as a forceps arm for example, at 16 cm or nearer on the z axis from the display, may have depth contradiction between the main image and additional image that exceeds −1 cm. Accordingly, that region is set to an additional image display-forbidden region.

Advantages

Portions having depth contradiction and excessively large difference in depth between the main image and additional image, due to body structures and inserting of medical instruments such as forceps and the like are handled as follows. Regions where determination is made that the detected depth position of body structures and medical instruments imaged in the main image may exceed the depth suitability range are stored as additional image display-forbidden regions, where no additional images are displayed even in a state with the medical instruments and the like removed. Accordingly, this does away with trouble such as a case where removal of inserted forceps temporarily resolves depth contradiction and so forth between the main image and additional image, the additional image is displayed on the region where the depth contradiction and so forth has been temporarily resolved, the forceps are inserted again resulting in depth contradiction, so the display position of the additional image is greatly changed. The search region range for the additional image display region also becomes narrower, so the load due to calculation is reduced.

Fourth Modification of Second Embodiment

While an arrangement has been described in the third modification of the second embodiment where the additional image display-forbidden region determined beforehand and the additional image display-forbidden region determined from an image imaged by the endoscope camera 111 are handled in the same way, the additional image display-forbidden region determined beforehand and the additional image display-forbidden region determined from an imaged image may be handled separately. The additional image display-forbidden region determined beforehand is the affected area to be treated by surgery and the perimeter thereof, at the center of the screen, and is a region where the main image must be displayed during surgery without fail. However, the additional image display-forbidden region determined from an imaged image is a region where depth contradiction may occur or difference in depth may be too great between the main image and the additional image. Since the additional image display-forbidden region determined from an imaged image is a region there depth contradiction may occur or difference in depth may be too great, so shielding such a region by an additional image can prevent depth contradiction or excessively great difference in depth from occurring. Note that in the present modification, a region where depth contradiction may occur or difference in depth may be too great will be referred to as a "possibly-unsuitable region".

Configuration

Figure 24:
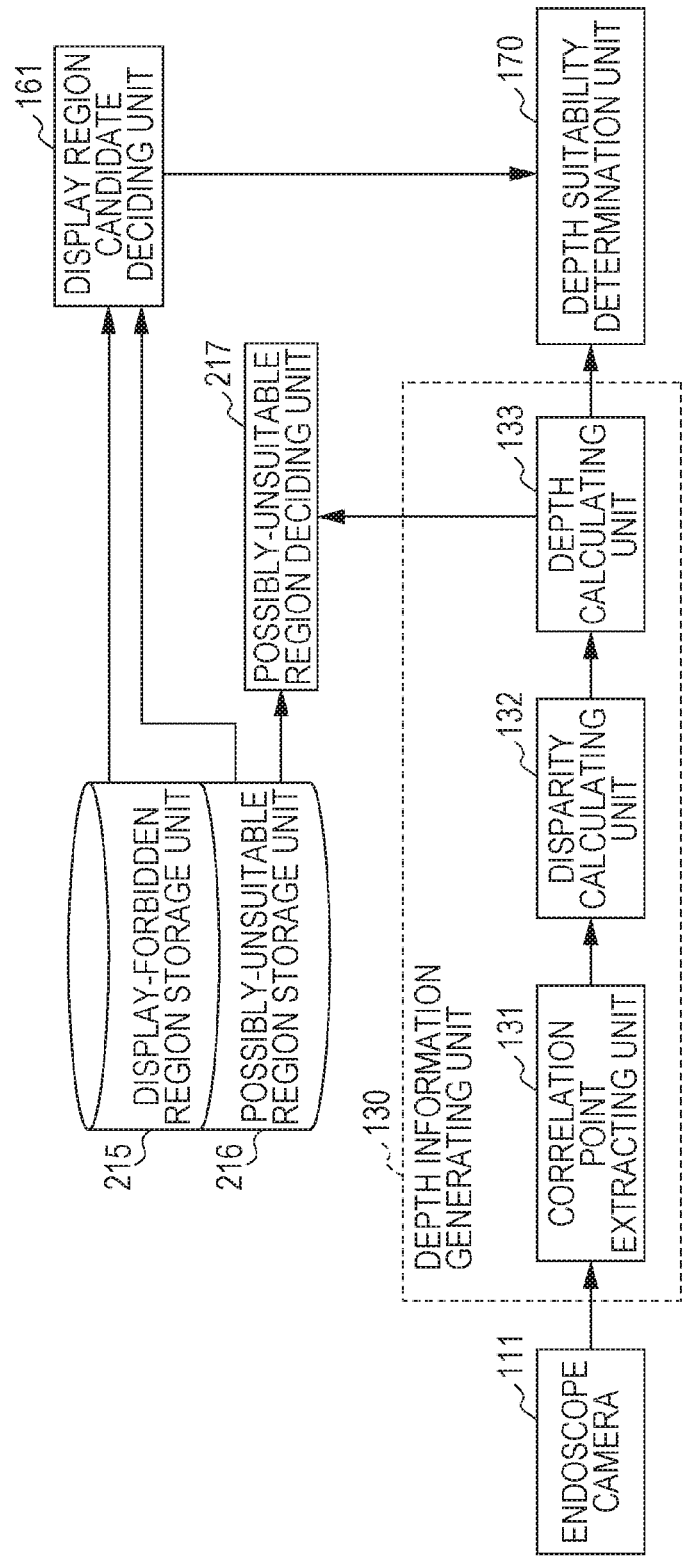
FIG. 24 is a block diagram illustrating a detailed functional configuration of a part of the 3D display device according to the fourth modification of the second embodiment.

FIG. 24 is a block diagram illustrating a part of a 3D display device according to a fourth modification of the second embodiment in detail. The configuration is the same as that in FIG. 22, other than the points that the display-forbidden region storage unit 213 has been replaced by a display-forbidden region storage unit 215, the display region candidate deciding unit 160 has been replaced by a display region candidate deciding unit 161, the forbidden region deciding unit 214 has been replaced by a possibly-unsuitable region deciding unit 217, and a possibly-unsuitable region storage unit 216 has been added. Portions which are the same as those in FIG. 22 are denoted by the same reference numerals, and description will be omitted.

The display-forbidden region storage unit 215 stores information of the additional image display-forbidden region determined beforehand.

The possibly-unsuitable region deciding unit 217 decides, from the depth information of an image imaged by the endoscope camera 111 that has been output from the depth information generating unit 130, a region where the possibility is great that depth contradiction will occur between the main image and additional image, or where the possibility is great that the difference in depth will be too great. That is to say, the possibly-unsuitable region deciding unit 217 decides regions in the main image where the depth protrudes too far in the near side beyond a predetermined depth range, and regions where the depth is recessed too far in the deep side beyond the predetermined depth range.

The possibly-unsuitable region storage unit 216 stores regions decided by the possibly-unsuitable region deciding unit 217.

The display region candidate deciding unit 161 decides a display region for the additional image, based on position information of the additional image which the additional image position storage unit 140 has acquired, size information of the additional image which the additional image size storage unit 150 has acquired, the additional image display-forbidden region that has been determined beforehand, acquired by the display-forbidden region storage unit 215, and information of regions in the image imaged by the endoscope camera 111 where the possibility is high that depth contradiction will occur or the difference in depth will be too great, acquired from the possibly-unsuitable region storage unit 216.

Operations

Figure 25:
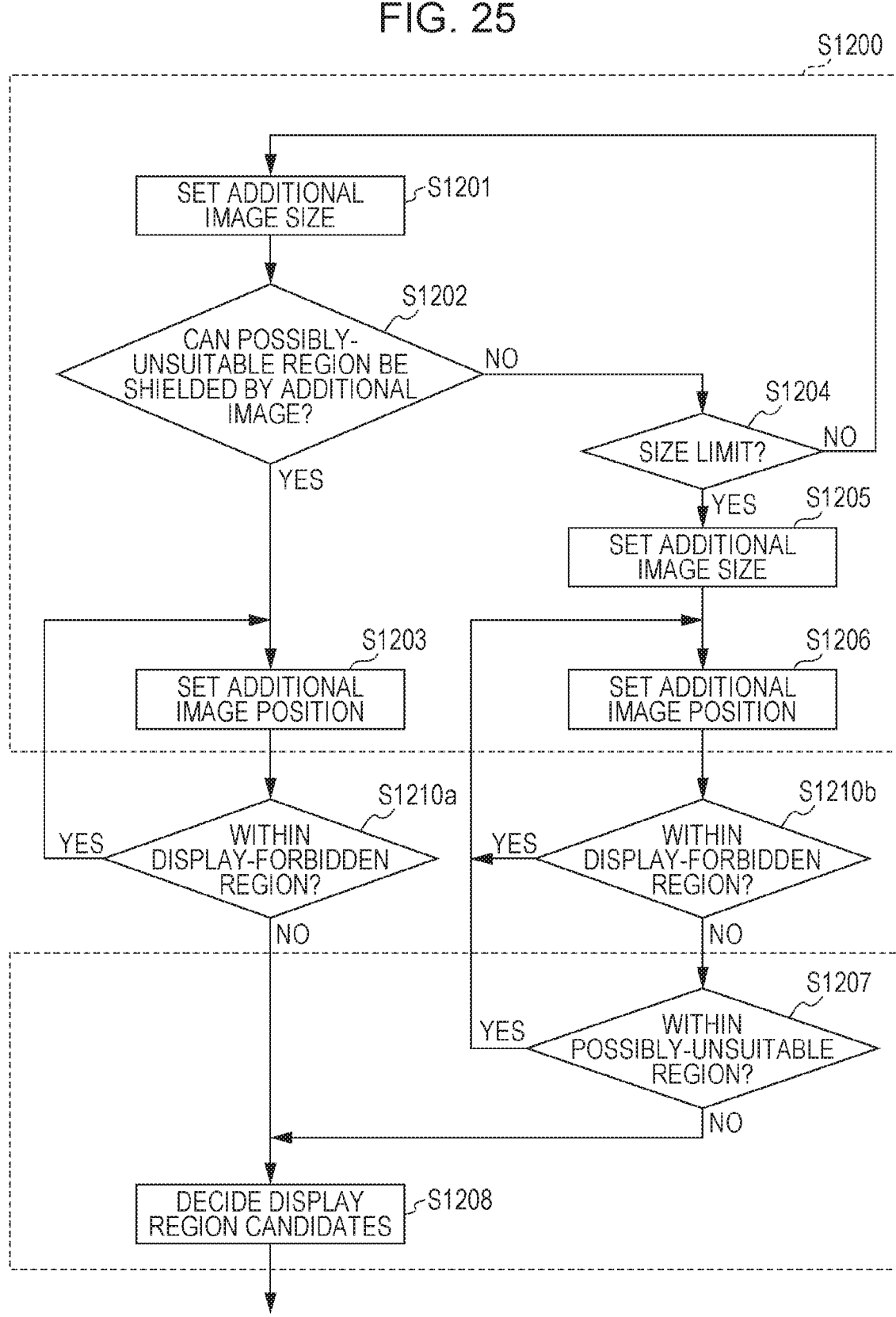
FIG. 25 is a flowchart illustrating detailed operations of part of processing operations of the 3D display device according to the fourth modification of the second embodiment.

FIG. 25 is a flowchart illustrating operations of the display region candidate deciding unit 161 deciding a display region for an additional image. The operations of FIG. 25 are a detailed illustration of the operations equivalent to steps S1200 and S1210 in FIG. 8, in a case where the additional image display-forbidden region determined beforehand and the additional image display-forbidden region determined from an imaged image are handled separately.

The display region candidate deciding unit 161 first sets the additional image size according to the size information of the additional image stored in the additional image size storage unit 150 (step S1201).

The display region candidate deciding unit 161 next compares the possibly-unsuitable region acquired from the possibly-unsuitable region storage unit 216 with the size of the additional image set in step S1201, and determines whether the possibly-unsuitable region can be shielded by the additional image (step S1202). In a case where determination is made in step S1202 that the possibly-unsuitable region can be shielded by the additional image, i.e., step S1202 yields "yes", the flow advances to step S1203. In a case where determination is made in step S1202 that the possibly-unsuitable region cannot be shielded by the additional image, i.e., step S1202 yields "no", the flow advances to step S1204.

The display region candidate deciding unit 161 sets the position of the additional image based on the position information stored in the additional image position storage unit 140 (step S1203).

The display region candidate deciding unit 161 then determines whether or not the region of the additional image, decided by the size of the additional image set in step S1201 and position of the additional image set in step S1203, includes a region regarding which display of an additional image has been forbidden, stored in the display-forbidden region storage unit 215 (step S1210a).

In a case where the set additional image region is determined in step S1210a to include a display-forbidden region, i.e., step S1210a yields "yes", the flow returns to step S1203. In a case where the set additional image region is determined in step S1210a to not include a display-forbidden region, i.e., step S1210a yields "no", the flow advances to step S1208.

On the other hand, the display region candidate deciding unit 161 determines whether or not the size of the additional image set in step S1201 is the limit value of the additional image size set beforehand in step S1201 or larger (step S1204). In a case where determination is made in step S1204 that the size of the additional image is equal or larger than the limit value, i.e., step S1204 yields "yes", the flow advances to step S1205. In a case where determination is made in step S1204 that the size of the additional image smaller than the limit value, i.e., step S1204 yields "no", the flow returns to step S1201.

In step S1205, the display region candidate deciding unit 161 references the additional image size storage unit 150 and resets the size of the additional image (step S1205).

The display region candidate deciding unit 161 further sets the position of the additional image based on the position information stored in the additional image position storage unit 140 (step S1206).

The display region candidate deciding unit 161 then determines whether or not the region of the additional image decided by the size of the additional image reset in step S1205 and the position of the additional image set in step S1206 includes a region regarding which display of an additional image has been forbidden, stored in the display-forbidden region storage unit 215 (step S1210b).

In a case where the set additional image region is determined in step S1210b to include a display-forbidden region, i.e., step S1210b yields "yes", the flow returns to step S1206. In a case where the set additional image region is determined in step S1210b to not include a display-forbidden region, i.e., step S1210b yields "no", the flow advances to step S1207.

The display region candidate deciding unit 161 then determines whether or not the set region of the additional image includes a region stored in the possibly-unsuitable region storage unit 216 (step S1207).

In a case where the additional image display region is determined in step S1207 to include a possibly-unsuitable region, i.e., step S1207 yields "yes", the flow returns to step S1206. In a case where the additional image display region is determined in step S1207 to not include a possibly-unsuitable region, i.e., step S1207 yields "no", the flow advances to step S1208.

In step S1208, the display region candidate deciding unit 161 decides the additional image display region of the set size and position to be a display region candidate (step S1208).

Advantages and Effects

As described above, a region in the main image where there is a possibility of depth contradiction or excessively large difference in depth occurring between the main image and additional image is shielded by the additional image, by adjusting the size and position of the additional image. In a case where this region in the main image cannot be shielded, the additional image is displayed at a position avoiding the region where there is a possibility of depth contradiction or excessively large difference in depth occurring between the main image and additional image. Thus, a natural 3D image which does not place a load on the user can be presented.

While description has been made in the fourth modification of the second embodiment that the size of the additional image is automatically adjusted, the size of the additional image may be adjusted only in a case where there is input from the input unit 200 to change the size of the additional image. Particularly, the processing to shield a region in the main image where there is a possibility of depth contradiction or excessively large difference in depth occurring between the main image and additional image by the additional image may be performed in a case where there is input instructing enlarging the size of the additional image.

Change of the size of the additional image may be made such that a portion of the periphery of the screen, where the arm portions of forceps that have been imaged are an extreme protruding image, is shielded by extending the shape of the additional image in the horizontal direction.

Thus, regions on the right-eye image and left-eye image that correspond to an object with large disparity due to extreme protrusion can be shielded in both images.

Fifth Modification of Second Embodiment

Description has been made in the second embodiment that the 3D display device 20 avoids the display-forbidden region stored in the display-forbidden region storage unit 210 based on the display position of the additional image stored in the additional image position storage unit 140, without the user operating the position of the additional image, and the additional image is moved to a position where unsuitable depth at the periphery of the boundary plane of the additional image display region can be avoided. A case will be described in the present modification where the user specifies the size of the additional image by input at the input unit 200.

The configuration of the 3D display device 20 according to a fifth modification is the same as that of the second embodiment, except that the output of the input unit 200 is input to the additional image size storage unit 150. Accordingly, illustration by way of drawings and description thereof will be omitted.

Figure 26:
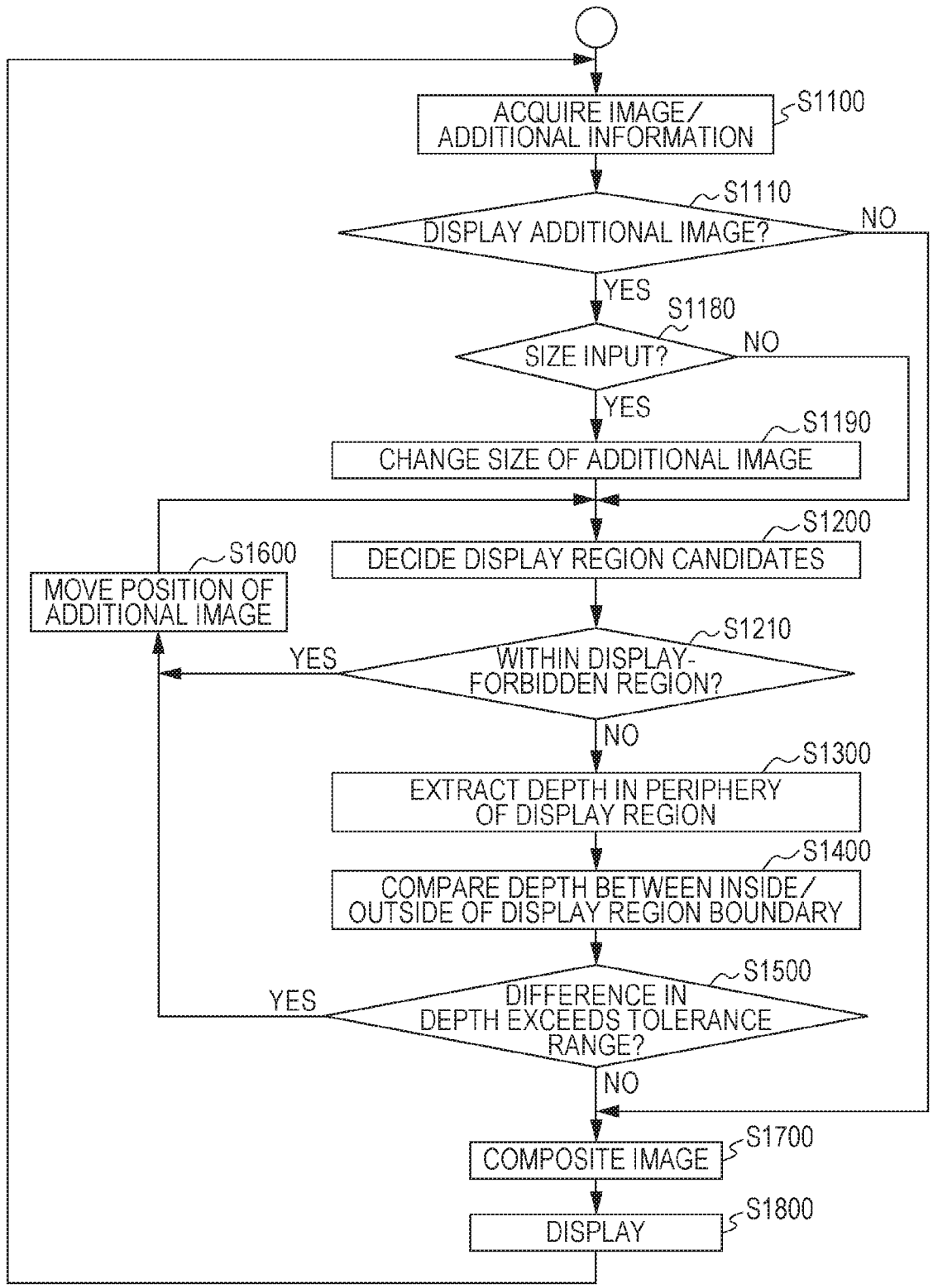
FIG. 26 is a flowchart illustrating processing operations of a 3D display device according to a fifth modification of the second embodiment.

FIG. 26 is a flowchart illustrating the operations of the 3D display device 20 according to the fifth modification of the second embodiment. FIG. 26 is the same as FIG. 8 in the second embodiment, other than steps S1180 and S1190 having been added. Portions which are the same as those in FIG. 8 will be denoted with the same reference numerals, and description will be omitted.

First, the endoscope camera 111 generates image information for 3D display having left and right disparity, as a main image, and the vital signs sensor 121 measures the current cardioelectric potential and blood pressure of the patient as additional information (step S1100).

The input unit 200 acquires operations according to user input, and detects instruction input to display an additional image (step S1110). In a case where additional image display instruction input is detected in step S1110, i.e., in a case where step S1110 yields "yes", the flow advances to step S1180. In a case where additional image display instruction input is not detected in step S1110, i.e., in a case where step S1110 yields "no", the flow advances to step S1700.

In step S1700, the image compositing unit 180 composites an endoscope camera image which is a main image with no additional image as a display image.

In step S1180, the input unit 200 further detects input of operating the size of the additional image (step S1180). In a case where input specifying the size of the additional image is detected in step S1180, i.e., in the case step S1180 yields "yes", the flow advances to step S1190. In a case where input specifying the size of the additional image is not detected in step S1180, i.e., in the case step S1180 yields "no", the flow advances to step S1200.

In step S1190, the input unit 200 outputs the information of size of the additional image in the instruction input relating to display of the additional image acquired in step S1110 to the additional image size storage unit 150. The additional image size storage unit 150 stores the information of the size of the additional image which the input unit 200 has output (step S1190).

The display region candidate deciding unit 160 decides one candidate for the display region, from the size of the additional image stored in the additional image size storage unit 150, and the position of the additional image stored in the additional image position storage unit 140 (step S1200).

For example, the display region candidate deciding unit 160 arbitrarily selects one unselected combination of additional image size stored in the additional image size storage unit 150 and additional image position stored in the additional image position storage unit 140, and decides a region represented by the selected combination as a display region candidate.

Note that the newest information of the additional image information stored in the additional image size storage unit 150 is used in step S1200. Accordingly, in a case where step S1190 has been executed, the size information recorded in step S1190 is used to decide the display region candidate.

The display region candidate deciding unit 160 determines whether or not the display region candidate decided in step S1200 includes the display-forbidden region stored in the display-forbidden region storage unit 210 (step S1210). In a case where determination is made in step S1210 that the display region candidate includes the display-forbidden region, i.e., in a case where step S1210 yields "yes", the flow advances to step S1600.

In step S1600, the display region candidate deciding unit 160 moves the display position of the additional image and stores the moved display position in the additional image position storage unit 140.

In a case where determination is made in step S1210 that the display region candidate does not include the display-forbidden region, i.e., in a case where step S1210 yields "no", the flow advances to step S1300.

Repeating steps S1200, S1210, and S1600 decides the display region candidate while avoiding the display-forbidden region. The depth suitability determination unit 170 extracts a boundary line or boundary plane of the additional image display region candidate decided in step S1200, and extracts depth information in the periphery of the boundary line or boundary plane (step S1300).

The depth suitability determination unit 170 further compares the depth of the display region of the additional image obtained from the position information of the additional image stored in the additional image position storage unit 140 with the depth of the main image at the portion adjacent to the boundary line or boundary plane of the additional image extracted in step S1300 (step S1400).

The depth suitability determination unit 170 determines whether or not the difference in depth of the main image and additional image displayed across the boundary line or boundary plane exceed the tolerance range (step S1500). In a case where determination is made in step S1500 that the difference in depth exceeds the tolerance range, i.e., in a case where step S1500 yields "yes", the flow advances to step S1600, and after executing step S1600, returns to step S1200. In a case where determination is made in step S1500 that the difference in depth is within the tolerance range, i.e., in a case where step S1500 yields "no", the flow advances to step S1700.

In step S1700, the image compositing unit 180 composites the main image acquired in step S1100 and the additional image representing the additional information acquired in step S1100. Specifically, the image compositing unit 180 displays the main image on the screen of the display 190, and displays the additional image so as to be displayed in the display region which is the display region candidate decided in step S1200, thus compositing the image.

The display 190 displays the 3D image composited in step S1700 (step S1800), and subsequently the flow returns to step S1100. Repeating steps S1100 through S1800 causes the 3D display device 20 to main acquire images and additional information in increments of processing, and continue displaying of images. The present embodiment is applicable in cases where the main image and additional image are moving images, as well.

Figure 27A:
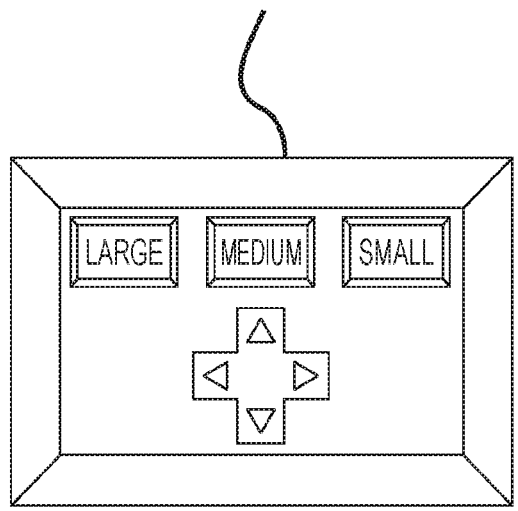
FIG. 27A is a schematic diagram illustrating an example of an input unit according to the fifth modification of the second embodiment.
Figure 27B:
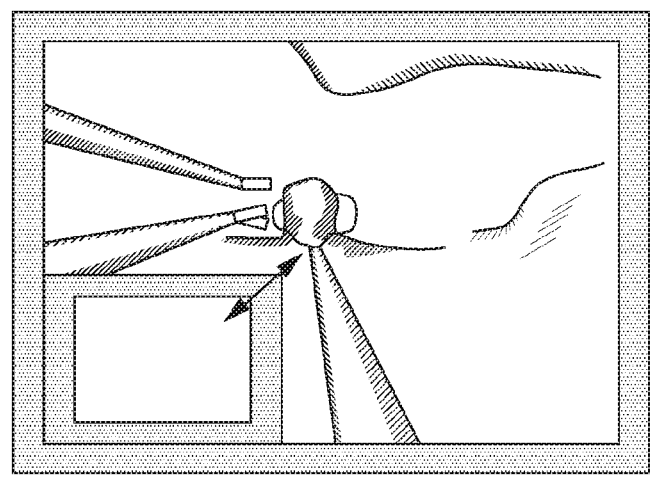
FIG. 27B is a schematic diagram illustrating an example of a display for describing the input unit according to the fifth modification of the second embodiment.

Now, the input unit 200 may be a switchbox such as illustrated in FIG. 27A, for example. In this arrangement, the user can select the size by pressing one of multiple buttons in the switchbox corresponding to multiple sizes (large, medium, and small buttons). Alternatively, the input unit 200 may be a pointing device such as a mouse or a stylus. In the example of an additional image size specifying screen illustrated in FIG. 27B, the user can move an arrow shown at a vertex of the additional image region by operating a pointing device. This, the additional image on the screen can be enlarged or reduced at will, and an operational size can be specified.

In another arrangement, the input unit 200 may include a camera which shoots the user, and an image processing device which distinguishes user operations from images of the user shot by the camera. This enables user operations to specify size. In another arrangement, the input unit 200 may include an input device whereby the user can input planar or 3D coordinate positions, direction of movement, and amount of movement, such as a touch panel or the like. In a case where the additional image is rectangular, the size may be specified by inputting the height and width of the sides as numerical values to specify the size. A text input device capable of inputting numerical values, such as a keyboard, can be used as the input unit 200 of the 3D display device 20. The input unit 200 of the 3D display device 20 further may be a touch panel, a handwriting recognition device which can take stylus input, or an audio input device capable of audio input. The size of the additional image region can be specified for shapes other than rectangles, by specifying the length of sides, diagonal lines, or the like.

Advantages

According to the fifth modification of the second embodiment described above, at the time of displaying an additional image over or adjacent to a 3D image from a stereo endoscope, the 3D display device 20 decides the display region of the additional image upon the user specifying the display size of the additional image, avoiding states with great difference in depth between the inside and outside of the boundary of the display region of the additional image, and states with depth contradiction. This enables the additional image to be displayed at a size which the user, i.e., the surgeon needs, while avoiding depth contradictions such as an additional image which appears to have embedded itself in the arms of the forceps, thereby alleviating fatigue of the user, i.e., the surgeon.

Sixth Modification of Second Embodiment

Description has been made in the fifth modification of the second embodiment regarding the 3D display device 20 which decides sizes following size instruction for additional images input from the input unit 200. The input unit 200 according to the fifth modification of the second embodiment includes an input device for input of planar or 3D coordinate positions, direction of movement, and amount of movement, and includes an input interface device used in a general environment. Description will be made in the sixth modification of the second embodiment regarding a method of instructing change of the size of additional image, based on motion of forceps.

Figure 28A:
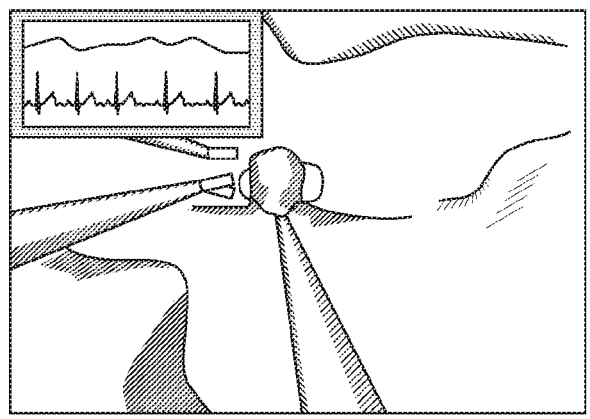
FIG. 28A is a schematic diagram illustrating an example of a display for describing input of additional image size according to a sixth modification of the second embodiment.
Figure 28B:
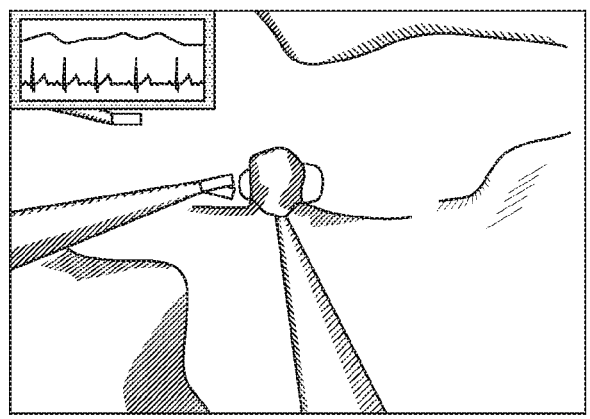
FIG. 28B is a schematic diagram illustrating an example of a display for describing input of additional image size according to the sixth modification of the second embodiment.

FIGS. 28A and 28B are diagrams schematically illustrating an arrangement where forceps are incorporated as a part of the input unit 200, and the size of the additional image display region is adjusted based on the movement of the forceps. FIGS. 28A and 28B show a main image of a wire looped over the affected area along with the forceps, and vital signs data is illustrated in a graph in which the horizontal axis is passage of time. The vital signs data is the additional image displayed superimposed on the main image. None of the forceps tips shown at the left side in FIGS. 28A and 28B overlap the additional image. In FIG. 28B, the region of the additional image is smaller as compared to FIG. 28A. When the surgeon pulls the forceps to the near side for example, the tips pass through the display region of the additional image (the boundary between the additional image and the main image). In a case where the forceps tips passage from outside of the display region of the additional image to inside the display region of the additional image is detected, the input unit 200 changes the shape of the additional image in accordance with the direction of movement of the forceps. In a case where the forceps tips move in a direction from the outside of the region toward the inside of the region, the movement of the tips is regarded as being input to reduce the size of the additional image display region, and in a case where the forceps tips move in a direction from the inside of the region toward the outside of the region, the movement of the tips is regarded as being input to enlarge the size of the additional image display region.

Figure 29:
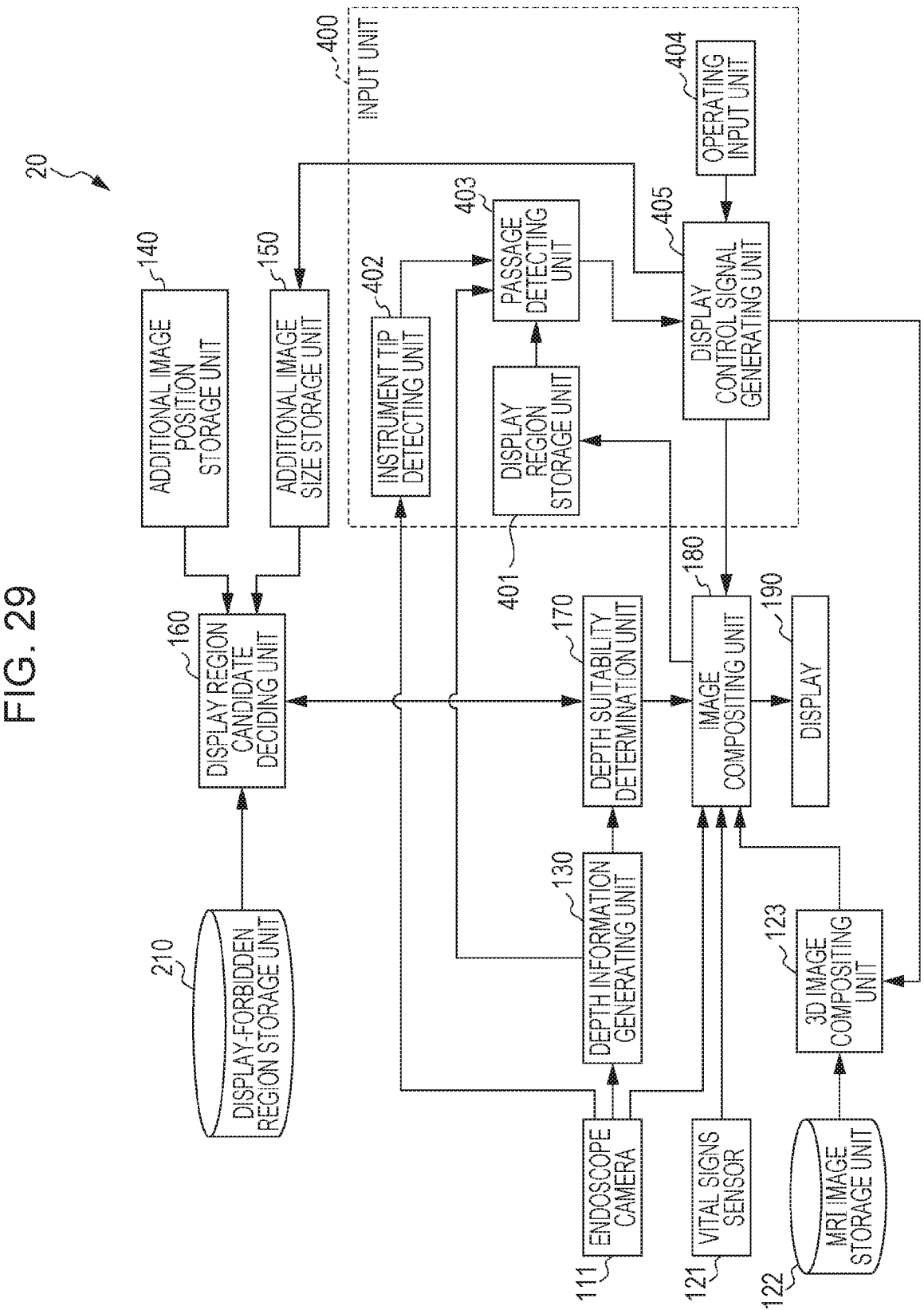
FIG. 29 is a block diagram illustrating a functional configuration of a 3D display device according to a seventh modification of the second embodiment.

FIG. 29 is a block diagram illustrating a functional configuration of the 3D display device 20 according to the sixth modification of the second embodiment. The configuration in FIG. 29 is the same as that of the 3D display device 10 according to the first embodiment illustrated in FIG. 2, except for addition of a display region storage unit 401, an instrument tip detecting unit 402, a passage detecting unit 403, an operating input unit 404, and a display control signal generating unit 405, as functional components of an input unit 400. Portions which are the same as those in FIG. 7 are denoted with the same reference numerals as in FIG. 7, and description thereof will be omitted.

The 3D display device 20 includes the endoscope camera 111, vital signs sensor 121, MRI image storage unit 122, 3D image compositing unit 123, depth information generating unit 130, additional image position storage unit 140, additional image size storage unit 150, display region candidate deciding unit 160, depth suitability determination unit 170, image compositing unit 180, display 190, display-forbidden region storage unit 210, and input unit 400. The input unit 400 includes the display region storage unit 401, instrument tip detecting unit 402, passage detecting unit 403, operating input unit 404, and a display control signal generating unit 405.

The endoscope camera 111 is a 3D imaging endoscope camera including a stereo camera.

The vital signs sensor 121 is a sensor attached to the body of the patient during surgery. In the sixth modification of the second embodiment, description will be made with the vital signs sensor 121 serving as an electrocardiogram and a sphygmomanometer.

The MRI image storage unit 122 stores 3D image information including images of the affected area to be treated by surgery, which have been recorded by an MRI system before surgery.

The 3D image compositing unit 123 composites image information stored in the MRI image storage unit 122 into images of a format which can be displayed on the display 190, as specified slices or a spectrogram of a specified range.

The additional image position storage unit 140 stores the position where the additional information is to be displayed on the screen as an additional image.

The additional image size storage unit 150 stores the size at which the additional information is to be displayed on the screen as an additional image.

The display-forbidden region storage unit 210 stores information representing a region determined beforehand where an affected area to be subjected to surgery has been photographed, as an additional image display-forbidden region. The display-forbidden region in the sixth modification of the second embodiment is a fixed rectangular region centered on the center of the screen.

The display region candidate deciding unit 160 decides display region candidates to display one or more of additional information on the screen of the display 190 as additional images. The additional information in the present modification is the two types of vital signs information acquired by the vital signs sensor 121 during surgery, and MRI image information recorded before the surgery. These two types of additional information are each to be displayed at display regions, as separate additional images.

The depth suitability determination unit 170 detects difference in depth greater than a predetermined value or depth contradiction, with regard to difference in depth between the display regions of the additional images and the portions of the main image which are at the periphery of the display regions of the additional images, based on information of display region candidates which the display region candidate deciding unit 160 has decided, and depth information of the main image which the depth information generating unit 130 has generated. The tolerance range is, for example –1 cm to 15 cm.

The image compositing unit 180 composites the 3D image and additional images such that the 3D image acquired by the endoscope camera 111 is displayed on the screen of the display 190, and the additional information acquired by the vital signs sensor 121 is displayed as additional images in at least one of the regions decided by the display region candidate deciding unit 160.

The display 190 displays the image composited by the image compositing unit 180.

The operating input unit 404 is a unit used by the user to instruct whether or not to display an additional image, and to input conditions for display of additional images.

The display control signal generating unit 405 acquires operations made by the user regarding the additional image input from the operating input unit 404, and generates control signals for the image compositing unit 180 to control image compositing.

The display region storage unit 401 stores a display region where additional information is currently displayed as an additional image. FIG. 30 illustrates an example of contents stored in the display region storage unit 401. The display region storage unit 401 stores IDs of additional image regions, the contents of the additional information for each ID, and three-dimensional coordinate positions of the four vertices for describing the display region as a rectangular plane.

The instrument tip detecting unit 402 detects the tips of surgical instruments in the image imaged by the endoscope camera 111. An example will be given here where forceps tips are detected. The method of detection is as follows. The instrument tip detecting unit 402 extracts metallic-colored regions as instrument regions from the color regions of the image imaged by the endoscope camera 111. The instrument tip detecting unit 402 obtains correlation points in the left and right images regarding the extracted regions. The instrument tip detecting unit 402 obtains the depth of the instrument regions from the correlation points that have been obtained. The instrument tip detecting unit 402 extracts the deepest part of a color region where the color is continuous as being the tip portion. Alternatively, after extracting a metallic-colored region, the outline of the extracted region and the outline of an instrument prepared beforehand may be subjected to pattern matching, thus deciding the tip. Other types of image processing may be performed to detect the tip of the instruments, as well.

The passage detecting unit 403 detects that the tip portion of the instrument detected by the instrument tip detecting unit 402 has passed through the additional image display region indicated by information stored in the display region storage unit 401. The method of detection is as follows. The passage detecting unit 403 extracts a three-dimensional coordinate position of the tip of the instrument which the instrument tip detecting unit 402 has detected, based on three-dimensional coordinate position of an object in the image generated by the depth information generating unit 130. For example, in a case of detecting that the three-dimensional coordinates of the tip of the instrument have passed through or come into contact with an additional image plane stored in the display region storage unit 401, the passage detecting unit 403 detects that the instrument tip has passed through the additional image region. When performing this detection, the passage detecting unit 403 also determines the direction of passage of the instrument tip, which is to say whether the instrument tip is moving in a direction from inside the additional image region toward the outside of the region, or moving in a direction from outside the additional image region toward the inside of the region. The passage detecting unit 403 outputs the information of the instrument tip passing through the additional image plane to the display control signal generating unit 220 along with the direction of passage.

Description has been made there that the passage detecting unit 403 uses three-dimensional coordinates to detect passage of the instrument tip through the additional image region, but an arrangement may be made where the three-dimensional coordinates of the additional image region and the three-dimensional coordinates of the instrument tip are mapped to the display plane, and passage of the instrument tip on the two-dimensional coordinates of the display plane is detected. In a case where the tip position of an instrument mapped to the display plane is within or in contact with the additional image region mapped to the display play, the instrument tip may be regarded to have passed through the additional image, and detection of passage thus performed.

The passage of the instrument tip through the additional image region and the passage direction thereof identifies an additional image regarding which the size is to be specified, and also indicates size changing information of this additional image. When changing the size, the amount of size change or the size change ratio per change may be made constant. Alternately, the amount of size change may be decided by the moving speed and moving distance of the instrument tip. The passage detecting unit 403 outputs to the display control signal generating unit 405 information of size specification input for a particular additional image from instrument operations performed by the surgeon, based on the three-dimensional coordinate information of the instrument tip output from the instrument tip detecting unit 402, and the coordinate information of the region for each additional image that has been stored in the display region storage unit 401.

The operations of the 3D display device 20 according to the sixth modification of the second embodiment are the same as those of the fifth modification of the second embodiment illustrated in FIG. 29.

In a case where an instruction input to display an additional image is detected in step S1110, the flow advances to step S1180.

The display control signal generating unit 405 detects input of operating the size of the additional image in step S1180. That is, the display control signal generating unit 405 detects the passage detecting unit 403 outputting information of size specification input for a particular additional image from instrument operations performed by the surgeon, based on the three-dimensional coordinate information of the instrument tip output from the instrument tip detecting unit 402, and coordinate information of the region for each additional image that has been stored in the display region storage unit 401.

In a case where input specifying the size of an additional image is detected in step S1180, the flow advances to step S1190. In a case where input specifying the size of an additional image is not detected in step S1180, the flow advances to step S1200.

Advantages

According to the sixth modification of the second embodiment described above, at the time of displaying an additional image over or adjacent to a 3D image from a stereo endoscope, the user, i.e., the surgeon, can use a surgical instrument in use which is in the images being shot by the endoscope camera. The display region of the additional image is decided, avoiding states with great difference in depth between the inside and outside of the boundary of the display region of the additional image, and states with depth contradiction. This enables the additional image to be displayed at a size which the user, i.e., the surgeon needs, while avoiding depth contradictions such as an additional image which appears to have embedded itself in the arms of the forceps, thereby alleviating fatigue of the user, i.e., the surgeon. Further, the user can specify the size of the additional image using the surgical instrument being used for the surgery, without using a special interface device. That is to say, the surgeon can specify the size of the additional image without turning loose of the surgical instrument being used. Accordingly, the 3D display device can be operated without loosing efficiency in surgery.

Seventh Modification of Second Embodiment

Description has been made that the 3D display device 20 according to the second embodiment displays an additional image at an additional image display position stored in the additional image position storage unit 140 which is also a position avoiding a display-forbidden region stored in the display-forbidden region storage unit 210, without the user operating the position of the additional image. Description will be made in the present modification regarding a case where the user inputs a display position of the additional image using the operating input unit 404, thereby instructing a display position.

The configuration of the 3D display device 20 according to a seventh modification is the same as that of the sixth modification of the second embodiment, except that the output of the display control signal generating unit 405 is input to the additional image position storage unit 140. Accordingly, illustration by way of drawings and description thereof will be omitted.

Figure 31:
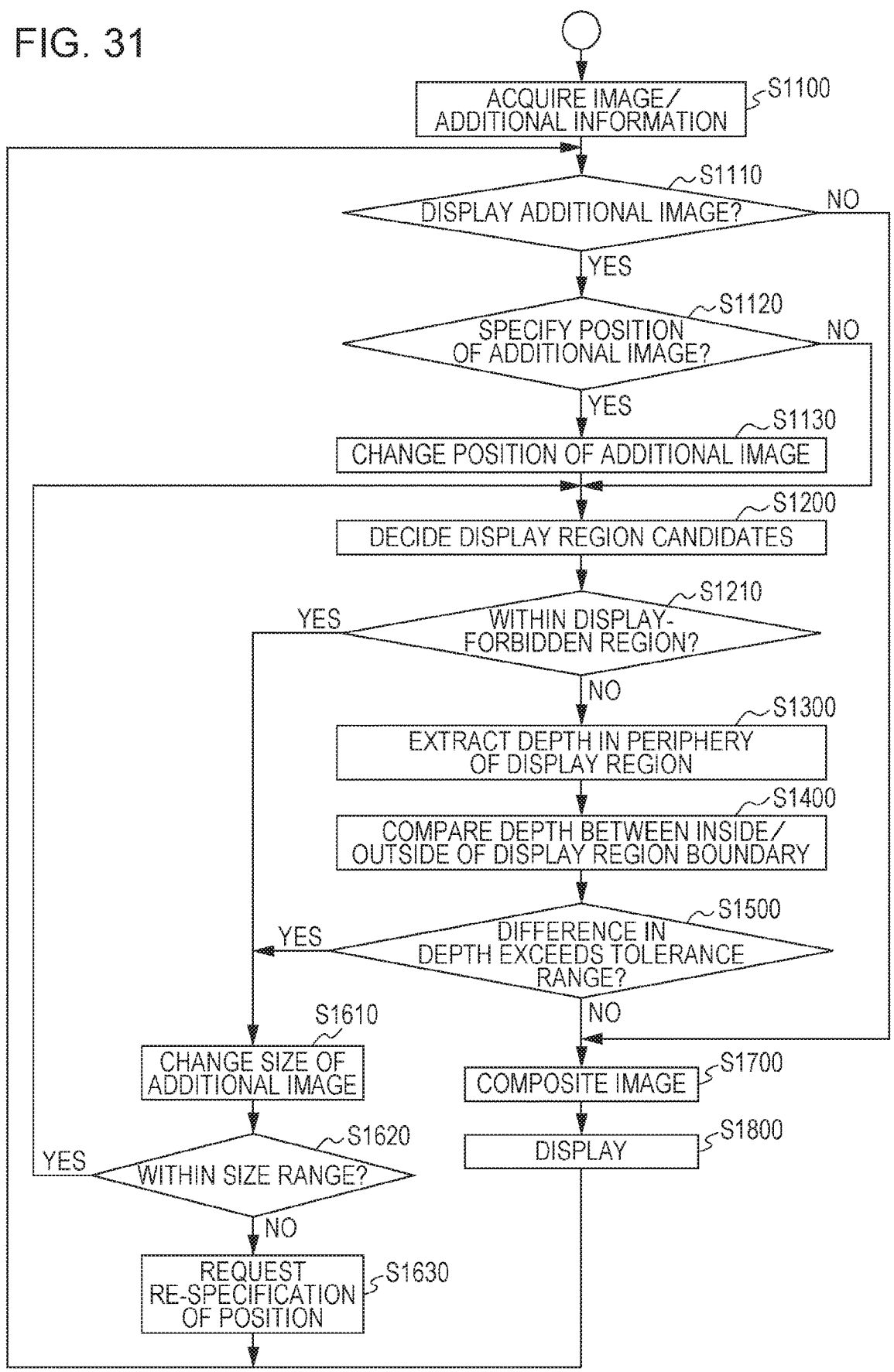
FIG. 31 is a flowchart illustrating processing operations of the 3D display device according to the seventh modification of the second embodiment.

FIG. 31 is a flowchart illustrating the operations of the 3D display device 20 according to the seventh modification of the second embodiment. FIG. 31 is the same as FIG. 8 in the second embodiment, other than step S1600 having been omitted and steps S1120, S1130, S1610, S1620, and S1630 having been added. Portions which are the same as those in FIG. 8 will be denoted with the same reference numerals, and description will be omitted.

First, the endoscope camera 111 generates image information for 3D display having left and right disparity, as a main image, and the vital signs sensor 121 measures the current cardioelectric potential and blood pressure of the patient as additional information (step S1100).

The display control signal generating unit 405 acquires operations which the user has made regarding the additional image at the operating input unit 404, and detects instruction input to display an additional image (step S1110). In a case where additional image display instruction input is detected in step S1110, i.e., in a case where step S1110 yields "yes", the flow advances to step S1120. In a case where additional image display instruction input is not detected in step S1110, i.e., in a case where step S1110 yields "no", the flow advances to step S1700.

In step S1700, the image compositing unit 180 composites an endoscope camera image which is a main image with no additional image as a display image.

In step S1120, the display control signal generating unit 405 further detects input of operating the position of the additional image. In a case where input specifying the position of the additional image is detected in step S1120, i.e., in the case step S1120 yields "yes", the flow advances to step S1130. In a case where input specifying the position of the additional image is not detected in step S1120, i.e., in the case step S1120 yields "no", the flow advances to step S1200.

In step S1130, the display control signal generating unit 405 outputs the information of position of the additional image in the instruction input relating to display of the additional image acquired in step S1110 to the additional image position storage unit 140. The additional image position storage unit 140 stores the information of the position of the additional image which the display control signal generating unit 405 has output (step S1130).

The display region candidate deciding unit 160 decides one candidate for the display region, from the size of the additional image stored in the additional image size storage unit 150, and the position of the additional image stored in the additional image position storage unit 140 (step S1200). For example, the display region candidate deciding unit 160 arbitrarily selects one unselected combination of additional image size stored in the additional image size storage unit 150 and additional image position stored in the additional image position storage unit 140, and decides a region represented by the selected combination as a display region candidate.

Note that the newest information of the additional image position information stored in the additional image position storage unit 140 is used to decide the display region candidate in step S1200. Accordingly, in a case where step S1130 has been executed, the position information recorded in step S1130 is used to decide the display region candidate.

The display region candidate deciding unit 160 determines whether or not the display region candidate decided in step S1200 includes the display-forbidden region stored in the display-forbidden region storage unit 210 (step S1210). In a case where determination is made in step S1210 that the display region candidate includes the display-forbidden region, i.e., in a case where step S1210 yields "yes", the flow advances to step S1610.

In a case where determination is made in step S1210 that the display region candidate does not include the display-forbidden region, i.e., in a case where step S1210 yields "no", the flow advances to step S1300.

The depth suitability determination unit 170 extracts a boundary line or boundary plane of the additional image display region candidate decided in step S1200, and extracts depth information in the periphery of the boundary line or boundary plane (step S1300).

The depth suitability determination unit 170 further compares the depth of the display region of the additional image obtained from the position information of the additional image stored in the additional image position storage unit 140 with the depth of the main image at the portion adjacent to the boundary line or boundary plane of the additional image extracted in step S1300 (step S1400).

The depth suitability determination unit 170 determines whether or not the difference in depth of the main image and additional image displayed across the boundary line or boundary plane (step S1500). In a case where determination is made in step S1500 that the difference in depth exceeds the tolerance range, i.e., in a case where step S1500 yields "yes", the flow advances to step S1610. In a case where determination is made in step S1500 that the difference in depth is within the tolerance range, i.e., in a case where step S1500 yields "no", the flow advances to step S1700.

In step S1700, the image compositing unit 180 composites the main image acquired in step S1100 and the additional image representing the additional information acquired in step S1100. Specifically, the image compositing unit 180 displays the main image on the screen of the display 190, and displays the additional image so as to be displayed in the display region which is the display region candidate decided in step S1200, thus compositing the image.

The display 190 displays the 3D image composited in step S1700 (step S1800), and subsequently the flow returns to step S1100.

In step S1610, the display region candidate deciding unit 160 changes the size of the additional image, and stores the changed size in the additional image size storage unit 150 (step S1610). For example, the display region candidate deciding unit 160 reduces the size of the additional image without changing the display position of the additional image so that the additional image display region does not include the display-forbidden region, i.e., so that the additional image display region is outside of the display-forbidden region. Changing of size is performed by maintaining the center-of-gravity position of the additional image display region while reducing the additional image so that the perimeter of the display region moves closer toward the center-of-gravity. Alternatively, one of the sides of the additional image display region that does not include the display-forbidden region may be fixed and the display region reduced in relation to the additional image.

The display region candidate deciding unit 160 determines whether or not the size of the additional image changed in step S1610 is within a predetermined certain range (step S1620). In a case where determination is made in step S1620 that the size of the additional image is within the predetermined certain range, i.e., "yes" in step S1620, the flow returns to step S1200. In a case where determination is made in step S1620 that the size of the additional image is not within the predetermined certain range, i.e., "no" in step S1620, the flow advances to step S1630. For example, in a case where the additional image is rectangular, the predetermined size range of the additional image is 3 cm to 10 cm in height, and 5 cm to 13 cm in width. In a case where the size of the additional image reduced in step S1610 is within this range, e.g., the size of the additional image is 4 cm in height and 7 cm in width, the flow returns to step S1200. In a case where the size of the additional image reduced in step S1610 is not within this range, e.g., the size of the additional image is 2 cm in height and 4 cm in width, the flow advances to step S1630.

In step S1630, the display region candidate deciding unit 160 transmits a signal to the image compositing unit 180 indicating that the size of the additional image is outside of the predetermined range. The image compositing unit 180 responds to this signal and generates an image of a message prompting the user to re-input the display position of the additional image. The display 190 then displays the message screen which the image compositing unit 180 has generated (step S1630). After executing step S1630, the flow returns to step S1110.

Repeating steps S1200 through S1610 causes the 3D display device 20 to decide display region candidates while avoiding the display-forbidden region. Further, repeating steps S1110 through S1630 causes the 3D display device 20 to decide display regions where the difference in depth within and outside of the boundary plane of the additional image does not exceed the tolerance range.

The following methods may also be used as methods to input the position of additional images using the operating input unit 404. For example, the user may select one display position from predetermined display positions. Alternatively, the user may specify the center-of-gravity point of the additional image display region, or the user may specify the position of the sides of the additional image display region.

Advantages

According to the seventh modification of the second embodiment described above, at the time of displaying an additional image over or adjacent to a 3D image from a stereo endoscope, the user specifies the display position of the additional image. The 3D display device 20 decides the display region of the additional image, avoiding states with great difference in depth between the inside and outside of the boundary of the display region of the additional image, and states with depth contradiction, and also following the position specified by the user. This enables the additional image to be displayed at a position which the user, i.e., the surgeon needs, while avoiding depth contradictions such as an additional image which appears to have embedded itself in the arms of the forceps, thereby alleviating fatigue of the user, i.e., the surgeon.

Eighth Modification of Second Embodiment

Description has been made that the 3D display device 20 according to the second embodiment displays an additional image at an additional image display position stored in the additional image position storage unit 140 which is also a position avoiding a display-forbidden region stored in the display-forbidden region storage unit 210, without the user operating the position of the additional image. Description will be made in the present modification regarding a case where the user inputs a display position and size of the additional image using the operating input unit 404, thereby instructing a display position and size. Note that in a case where the display region of the additional image of which the display position and size is specified by user input includes the display-forbidden region, and in a case where the difference in depth between within and outside of the boundary plane of the additional image display region exceeds the tolerance range, the 3D display device automatically adjusts the position and size of the additional image display region. If the user is dissatisfied with the results of automatic adjustment, or of the display region obtained within the range of automatic adjustment is unsatisfactory, the 3D display device request the user to re-input the position and size of the additional image display region.

The configuration of the 3D display device 20 according to an eighth modification is the same as that of the sixth modification of the second embodiment, except that the output of the display control signal generating unit 405 is input to the additional image position storage unit 140 and the additional image size storage unit 150. Accordingly, illustration by way of drawings and description thereof will be omitted.

Figure 32B:
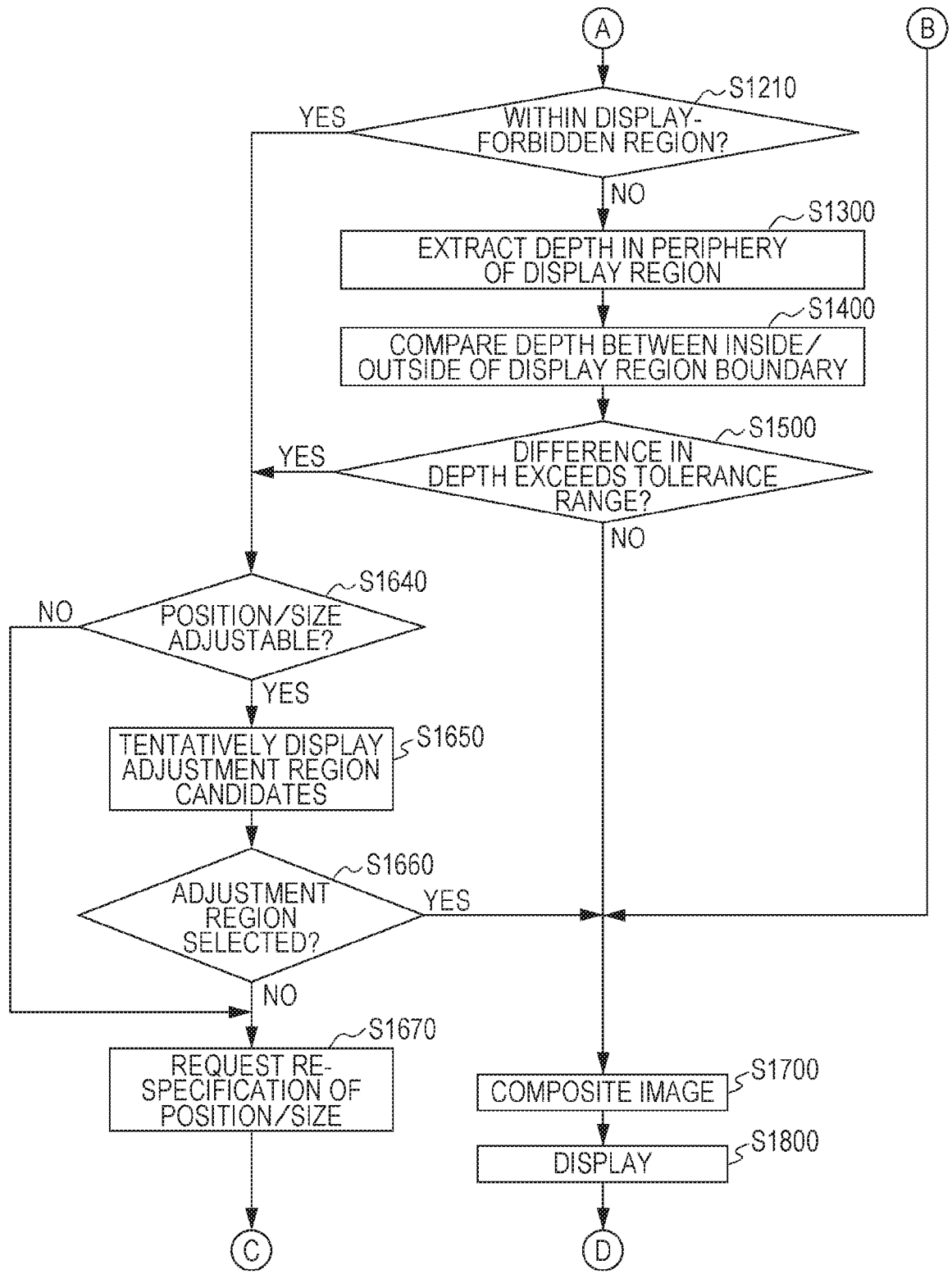
FIG. 32B is a flowchart illustrating processing operations of the 3D display device according to the eighth modification of the second embodiment.

FIGS. 32A and 32B are a flowchart illustrating the operations of the 3D display device 20 according to the eighth modification.

First, the endoscope camera 111 acquires image information for 3D display having left and right disparity, as a main image, and the vital signs sensor 121 measures the current cardioelectric potential and blood pressure of the patient as additional information (step S1100).

The display control signal generating unit 405 acquires operations which the user has made regarding the additional image at the operating input unit 404, and detects instruction input to display an additional image (step S1110). In a case where additional image display instruction input is detected in step S1110, i.e., in a case where step S1110 yields "yes", the flow advances to step S1120. In a case where additional image display instruction input is not detected in step S1110, i.e., in a case where step S1110 yields "no", the flow advances to step S1700.

In step S1700, the image compositing unit 180 composites an endoscope camera image which is a main image with no additional image as a display image.

In step S1120, the display control signal generating unit 405 further detects input of operating the position of the additional image. In a case where input specifying the position of the additional image is detected in step S1120, i.e., in the case step S1120 yields "yes", the flow advances to step S1130. In a case where input specifying the position of the additional image is not detected in step S1120, i.e., in the case step S1120 yields "no", the flow advances to step S1180.

In step S1130, the display control signal generating unit 405 outputs the information of position of the additional image in the instruction input relating to display of the additional image acquired in step S1110 to the additional image position storage unit 140. The additional image position storage unit 140 stores the information of the position of the additional image which the display control signal generating unit 405 has output (step S1130).

In step S1180, the display control signal generating unit 405 further detects input of operating the size of the additional image. In a case where input specifying the size of the additional image is detected in step S1180, i.e., in the case step S1180 yields "yes", the flow advances to step S1190. In a case where input specifying the size of the additional image is not detected in step S1180, i.e., in the case step S1180 yields "no", the flow advances to step S1200.

In step S1190, the display control signal generating unit 405 outputs the information of size of the additional image in the instruction input relating to display of the additional image acquired in step S1110 to the additional image size storage unit 150. The additional image size storage unit 150 stores the information of the size of the additional image which the display control signal generating unit 405 has output (step S1190).

The display region candidate deciding unit 160 decides one candidate for the display region, from the size of the additional image stored in the additional image size storage unit 150, and the position of the additional image stored in the additional image position storage unit 140 (step S1200). That is to say, the display region candidate deciding unit 160 decides as a display region candidate a region represented by the combination of the size of the additional image stored in the additional image size storage unit 150 and the position of the additional image stored in the additional image position storage unit 140.

Note that the newest information of the position of the additional image stored in the additional image position storage unit 140, and the newest information of the size of the additional image stored in the additional image size storage unit 150, are used in step S1200. Accordingly, in a case where step S1130 has been executed, the position information recorded in step S1130 is used to decide the display region candidate.

The display region candidate deciding unit 160 determines whether or not the display region candidate decided in step S1200 includes the display-forbidden region stored in the display-forbidden region storage unit 210 (step S1210). In a case where determination is made in step S1210 that the display region candidate includes the display-forbidden region, i.e., in a case where step S1210 yields "yes", the flow advances to step S1640.

In a case where determination is made in step S1210 that the display region candidate does not include the display-forbidden region, i.e., in a case where step S1210 yields "no", the flow advances to step S1300.

The depth suitability determination unit 170 extracts a boundary line or boundary plane of the additional image display region candidate decided in step S1200, and extracts depth information in the periphery of the boundary line or boundary plane (step S1300).

The depth suitability determination unit 170 further compares the depth of the display region of the additional image obtained by the display region candidate deciding unit 160 from the position information of the additional image stored in the additional image position storage unit 140 with the depth of the main image at the portion adjacent to the boundary line or boundary plane of the additional image extracted in step S1300 (step S1400).

The depth suitability determination unit 170 determines whether or not the difference in depth of the main image and additional image displayed across the boundary line or boundary plane exceeds the predetermined tolerance range (step S1500). In a case where determination is made in step S1500 that the difference in depth exceeds the tolerance range, i.e., in a case where step S1500 yields "yes", the flow advances to step S1610. In a case where determination is made in step S1500 that the difference in depth is within the tolerance range, i.e., in a case where step S1500 yields "no", the flow advances to step S1700.

In step S1700, the image compositing unit 180 composites the main image acquired in step S1100 and the additional image representing the additional image information acquired in step S1100. Specifically, the image compositing unit 180 displays the main image on the screen of the display 190, and displays the additional image so as to be displayed in the display region which is the display region candidate decided in step S1200, thus compositing the image.

The display 190 displays the 3D image composited in step S1700 (step S1800), and subsequently the flow returns to step S1100.

In step S1640, the display region candidate deciding unit 160 determines whether or not the position and size of the additional image can be adjusted (step S1640). The method of determination in step S1640 will be described later. In a case where determination is made in step S1640 that the position and size of the additional image can be adjusted, i.e., step S1640 yields "yes", the flow advances to step S1650. In a case where determination is made in step S1640 that the position and size of the additional image cannot be adjusted, i.e., step S1640 yields "no", the flow advances to step S1670.

In step S1650, the image compositing unit 180 composites a tentative display image where the additional image display region output from the depth suitability determination nit 170 has been overlaid on the main image, and the display 190 displays the tentative display image composited by the image compositing unit 180 (step S1650). The actual additional information may be displayed as the additional image in the tentative display image, or alternatively, a uniform plane image or a fixed test image for tentative display of the region may be used.

The display control signal generating unit 405 acquires user operations of the additional image made at the operating input unit 404 with regard to the tentative display of the additional image display region displayed on the display 190 in step S1650, and detects instruction input accepting the region of the additional image of which the tentative display position and size have been adjusted (step S1660). In a case where instruction input accepting the tentatively displayed additional image display region has been detected, i.e., step S1660 yields "yes", the flow advances to step S1700. In a case where instruction input accepting the tentatively displayed additional image display region is not detected, i.e., step S1660 yields "no", the flow advances to step S1670.

In step S1670 the image compositing unit 180 indicates to the user that the additional image cannot be displayed with the position and size of the additional image which the user has instructed, generates a message screen to prompt the user to re-specify the position and size of the additional image, and the display 190 displays the message generated at the image compositing unit 180 (step S1670). After displaying the message screen on in step S1670, the flow returns to step S1110.

Repeating steps S1110 through S1630 causes the 3D display device 20 to decide display region candidates while avoiding the display-forbidden region, and to decide display region candidates where the difference in depth within and outside of the boundary plane of the additional image does not exceed the tolerance range.

Details of Step S1640

FIG. 33 is a block diagram illustrating part of the 3D display device 20 according to the eighth modification of the second embodiment in detail. The display region candidate deciding unit 160 includes a position adjustment range storage unit 166, a size adjustment range storage unit 162, a region deciding unit 163, a distance calculating unit 164, and a region storage unit 165.

The position adjustment range storage unit 166 stores a predetermined range where an additional image can be moved, as a range where the display position of an additional image which the user has specified can be automatically adjusted. For example, this automatically-adjustable range is a range 20% or less the length of the long side of the additional image which the user has specified, in the long side direction or major axis direction, and 20% or less the length of the short side in the short side direction or minor axis direction. For example, in a case where the additional image is a rectangle, the display position of the additional image can be adjusted by moving horizontally within a range of 20% or less of the long side, and by moving vertically within a range of 20% or less of the short side. The display position of the additional image in the depth direction is not changed here.

The size adjustment range storage unit 162 stores the predetermined automatically-adjustable range as a range where the display size of the additional image specified user can be automatically adjusted. For example, this automatically-adjustable range is a range of 15% or less increase or decrease in the length of the major axis and minor axis of the additional image which the user has specified. For example, in a case where the additional image is a rectangle, the major axis and minor axis can both be adjusted within a range of 85% to 115% as to the size which the user has specified. Note however, that the scale of change is the same for the long sides and the short side, i.e., deformation of the additional image display region (size change with the aspect ratio changes) is not performed here. Further, the size of the additional image in the depth direction is not changed here.

The region deciding unit 163 receives input from the additional image position storage unit 140, the additional image size storage unit 150, the size adjustment range storage unit 162, the distance calculating unit 164, the region storage unit 165, and the depth suitability determination unit 170, and outputs information relating to display region candidates for the additional image to the distance calculating unit 164 and the region storage unit 165. The region deciding unit 163 acquires the display position of the additional image and the size of the additional image which the user has specified, from the additional image position storage unit 140 and additional image size storage unit 150, and decides the display region of the additional image. The region deciding unit 163 further follows input from the distance calculating unit 164 or input from the depth suitability determination unit 170 and adjusts the position and size of the display region of the additional image, based on the adjustment range of the additional image display position stored in the position adjustment range storage unit 166 and the adjustment range of the additional image display size stored in the size adjustment range storage unit 162.

The distance calculating unit 164 calculates the distance between the additional image display region candidate acquired by the region deciding unit 163, and the display-forbidden region stored in the display-forbidden region storage unit 210, in the image display space. For example, the distance calculating unit 164 maps each of the display-forbidden region and the additional image display region candidate in the image display space, onto the display plane, and compare the positions of the two on the display plane, thereby calculating the distance between the two. The distance calculating unit 164 can calculate the distance between the two regions from the difference in x coordinates and y coordinates in the coordinate system such as illustrated in FIG. 2B, for example. The distance calculating unit 164 outputs the calculation results to the region deciding unit 163.

The region storage unit 165 stores information relating to the additional image display region candidates decided by the region deciding unit 163.

Figure 34:
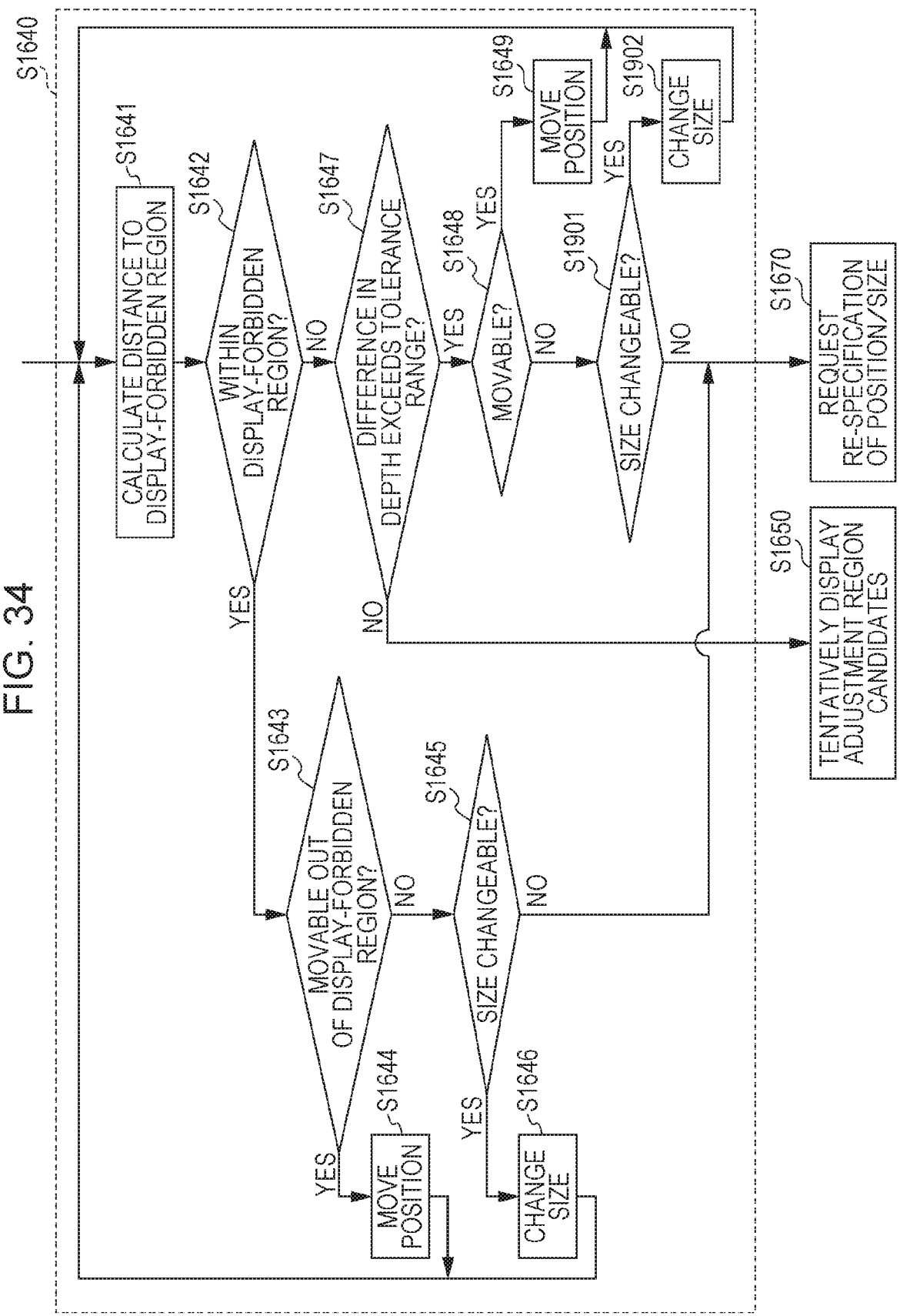
FIG. 34 is a flowchart illustrating processing operations of the display region candidate deciding unit according to the eighth modification of the second embodiment.

FIG. 34 is a flowchart illustrating detailed operations of step S1640 in the operations of the 3D display device 20 in the eighth embodiment of the second embodiment. In step S1640, the display region candidate deciding unit 160 determines whether or not the position and the size of the additional image can be adjusted.

The distance calculating unit 164 calculates the distance between the newest additional image display region candidate decided at the region deciding unit 163 and the display-forbidden region stored in the display-forbidden region storage unit 210 (step S1641). The distance is expressed by a positive value if the two regions mapped to the display plane are separated, and a negative value if two regions are overlapping. In a case where there is no overlapping between the two regions, the distance between the regions is the distance between the two closest points of the two regions. In a case where the two regions are overlapping, the distance is the negative value of the longest line that can be fit into the overlapped region.

Based on the distance between regions measured in step S1641, the region deciding unit 163 determines whether or not the newest additional image display region candidate includes the display-forbidden region stored in the display-forbidden region storage unit 210 (step S1642). If the distance is a negative value, this means that the two regions are overlapped, and consequently the additional image display region candidate includes the display-forbidden region. In a case where determination is made in step S1642 that the additional image display region candidate includes the display-forbidden region, i.e., step S1642 yields "yes", the flow advances to step S1643. In a case where determination is made in step S1642 that the additional image display region candidate does not include the display-forbidden region, i.e., step S1642 yields "no", the flow advances to step S1647.

In step S1643, the region deciding unit 163 determines whether or not the display region candidate can be moved to a position not including the display-forbidden region, based on the negative inter-region distance calculated in step S1641, i.e., the overlapping distance of the regions, and the adjustment range of the position stored in the position adjustment range storage unit 166. This determination is made by whether or not the absolute value of the inter-region distance is within the position adjustment range, for example. In a case where determination is made in step S1643 that the display region candidate can be moved to a position not including the display-forbidden region, i.e., step S1643 yields "yes", the flow advances to step S1644. In a case where determination is made in step S1643 that the display region candidate cannot be moved to a position not including the display-forbidden region, i.e., step S1643 yields "no", the flow advances to step S1645.

In step S1644, the region deciding unit 163 moves this additional image display region candidate, and resets this position where the display region candidate does not include the display-forbidden region as the position of the display region candidate. After executing step S1644, the flow returns to step S1641.

In step S1645, the region deciding unit 163 determines whether or not the size of the display region candidate can be adjusted so that the display region candidate does not include the display-forbidden region, based on the negative inter-region distance calculated in step S1641, i.e., the overlapping distance of the regions, and the size adjustment range stored in the size adjustment range storage unit 162. This determination is made by whether or not the absolute value of the inter-region distance is within the length adjustment range, for example. For the additional image display region candidate to be made to not include the display-forbidden region without changing the position thereof, the size of the display region candidate is reduced without changing the center-of-gravity position of the display region candidate serving as a position reference, for example. In a case where determination is made in step S1645 that the size of the display region candidate can be adjusted so that the display region candidate does not include the display-forbidden region, i.e., step S1645 yields "yes", the flow advances to step S1646. In a case where determination is made in step S1645 that the size of the display region candidate cannot be adjusted so that the display region candidate does not include the display-forbidden region, i.e., step S1645 yields "no", the flow advances to step S1670.

In step S1646, the region deciding unit 163 changes the size of this additional image display region candidate, and resets this size where the display region candidate does not include the display-forbidden region as the size of the display region candidate. After executing step S1646, the flow returns to step S1641.

Repeating steps S1641 through S1644 or 1646 adjusts the position or size within the predetermined adjustment range, thereby deciding an additional image display region candidate not including the display-forbidden region. In a case where an additional image display region candidate not including the display-forbidden region cannot be decided by adjusting the position or size within the predetermined adjustment range, the image compositing unit 180 presents the user is a request to re-specify the position and size of the display region of the additional image (step S1670). For example, the image compositing unit 180 displays a request message on the screen of the display 190 for re-specifying.

On the other hand, in step S1647 the depth suitability determination unit 170 determines whether or not the difference between the depth within and outside of the boundary plane of the additional image display region candidate decided by the region deciding unit 163 exceeds the tolerance range. The operations of step S1647 are the same as the operations of steps S1300 through S1500. In a case where determination is made in step S1647 that the difference between the depth within and outside of the boundary plane exceeds the tolerance range, i.e., "yes" in step S1647, the flow advances to step S1648. In a case where determination is made in step S1647 that the difference between the depth within and outside of the boundary plane does not exceed the tolerance range, i.e., "no" in step S1647, the flow advances to step S1650.

In step S1648, the region deciding unit 163 determines whether or not the position of the additional image display region candidate can be moved within the position adjustment range stored in the position adjustment range storage unit 166. That is to say, the region deciding unit 163 determines whether or not there is a possibility of movement not exceeding the adjustment range of the additional image display region stored in the position adjustment range storage unit 166, e.g., the adjustment range which is 20% of the length of the additional image region in the movement direction from the specified display position. An example will be considered here where the additional image is rectangular, there are four selections which can be made from the specified display position in the horizontal direction, which are movement of 10% of the horizontal axis to the right, movement of 20% to the right, movement of 10% of the horizontal axis to the left, and movement of 20% to the left, and there are four selections which can be made from the specified display position in the vertical direction, which are movement of 10% of the vertical axis upwards, movement of 20% upwards, movement of 10% of the vertical axis downwards, and movement of 20% downwards. In this case, if there is any combination of the four types of movement in the horizontal direction and the four types of movement in the vertical direction that has not been subjected to position adjustment operations, the region deciding unit 163 determines that the position of the display region candidate can be moved. On the other hand, in a case that all combinations have been subjected to position adjustment operations, the region deciding unit 163 determines that the position of the display region candidate cannot be moved.

In a case where determination is made in step S1648 that the position of the display region candidate can be moved, i.e., step S1648 yields "yes", the flow advances to step S1649. In a case where determination is made in step S1648 that the position of the display region candidate cannot be moved, i.e., step S1648 yields "no", the flow advances to step S1901.

In step S1649, the region deciding unit 163 selects one of the selectable display positions of the additional image display region candidates, and moves the display position of the additional image display region candidate (step S1649). After executing step S1649, the flow returns to step S1641.

In step S1901, the region deciding unit 163 determines whether or not the size of the additional image display region candidate can be changed within the size adjustment range stored in the size adjustment range storage unit 162. That is to say, the region deciding unit 163 determines whether or not the size of the additional image display region specified by user input in step S1120 can be changed within the adjustment range of the additional image display region stored in the size adjustment range storage unit 162. For example, determination is made regarding whether or not there is a possibility of extending or compressing the size of the additional image display region specified by user input within 15% in the major axis direction or minor axis direction of the display region. An example will be considered here where the additional image is rectangular, and can be expanded by 5%, expanded by 10%, expanded by 15%, compressed by 5%, compressed by 10%, or compressed by 15%, in length of the additional image rather than area of the additional image. If there are any of the six types of size change remaining as an option, the region deciding unit 163 determines that the size of the display region candidate can be changed. If all of the six types of size change have already been used for adjustment operations, the region deciding unit 163 determines that the size of the display region candidate cannot be changed.

In a case where determination is made in step S1901 that the size of the display region candidate can be changed, i.e., step S1901 yields "yes", the flow advances to step S1902. In a case where determination is made in step S1901 that the size of the additional image display region candidate cannot be changed, i.e., step S1901 yields "no", the flow advances to step S1670.

In step S1902, the region deciding unit 163 selects one of the selectable sizes of the additional image display region candidate, and changes the size of the additional image display region candidate (step S1902). After executing step S1902, the flow returns to step S1641.

Repeating steps S1641 through S1649 or S1902 enables the difference in depth within and outside of the boundary plane of the additional image to be adjusted to within the tolerance range. In a case where the difference in depth within and outside of the boundary plane of the additional image cannot be adjusted to be within the tolerance range by position and size adjustment within the predetermined adjustment range, the image compositing unit 180 presents the user is a request to re-specify the position and size of the additional image display region (step S1670). For example, the image compositing unit 180 displays a request message for re-specifying on the screen of the display 190.

While description has been made in the eighth modification of the second embodiment that the display region candidate deciding unit 160 does not adjust the display position in the depth direction, an arrangement may be made where the display position is moved in the depth position in the same way as the horizontal direction and vertical direction to perform adjustment. Particularly, in a case where there is difference in depth at the boundary plane of the additional image which slightly exceeds the tolerance range, there may be cases where moving the display region of the additional image in the depth direction is effective. In this case, the additional image can be moved toward the near side and the far side to adjust the depth direction, with the range of adjustment in the depth direction begin set to 10% or less of the original depth range, or set to 10% or less of the distance to the display plane from the original average depth position or smallest depth position.

Advantages

According to the eighth modification of the second embodiment described above, at the time of the 3D display device 20 displaying an additional image over or adjacent to a 3D image from a stereo endoscope, the user specifies the display position of the additional image. The 3D display device 20 decides the display region of the additional image, avoiding states with great difference in depth between the inside and outside of the boundary of the display region of the additional image, and states with depth contradiction, and also following the position specified by the user. This enables the additional image to be displayed at a position which the user, i.e., the surgeon needs, while avoiding depth contradictions such as an additional image which appears to have embedded itself in the arms of the forceps, thereby alleviating fatigue of the user, i.e., the surgeon.

Ninth Modification of Second Embodiment

Description has been made regarding the fifth through eighth modifications of the second embodiment that the difference in depth within and outside of the boundary plane of the additional image is kept from exceeding the tolerance range, by adjusting the position and size of the additional image display region which the user has specified. However, deformation of the additional image display region is not performed in the fifth through eighth modifications of the second embodiment. In the ninth embodiment, the difference in depth within and outside of the boundary plane of the additional image is prevented from exceeding the tolerance range, by deforming the additional image display region. The configuration of the display of additional information is changed in the ninth embodiment in accordance with deformation of the additional image display region. In a case where the additional information is information of a type which the spatial configuration cannot be deformed, such as image information, deformation of the display region is not valid. Description will be made in the present modification regarding deformation of the display region involving changing of the configuration of the display, using an example of vital signs information.

Configuration

Figure 35:
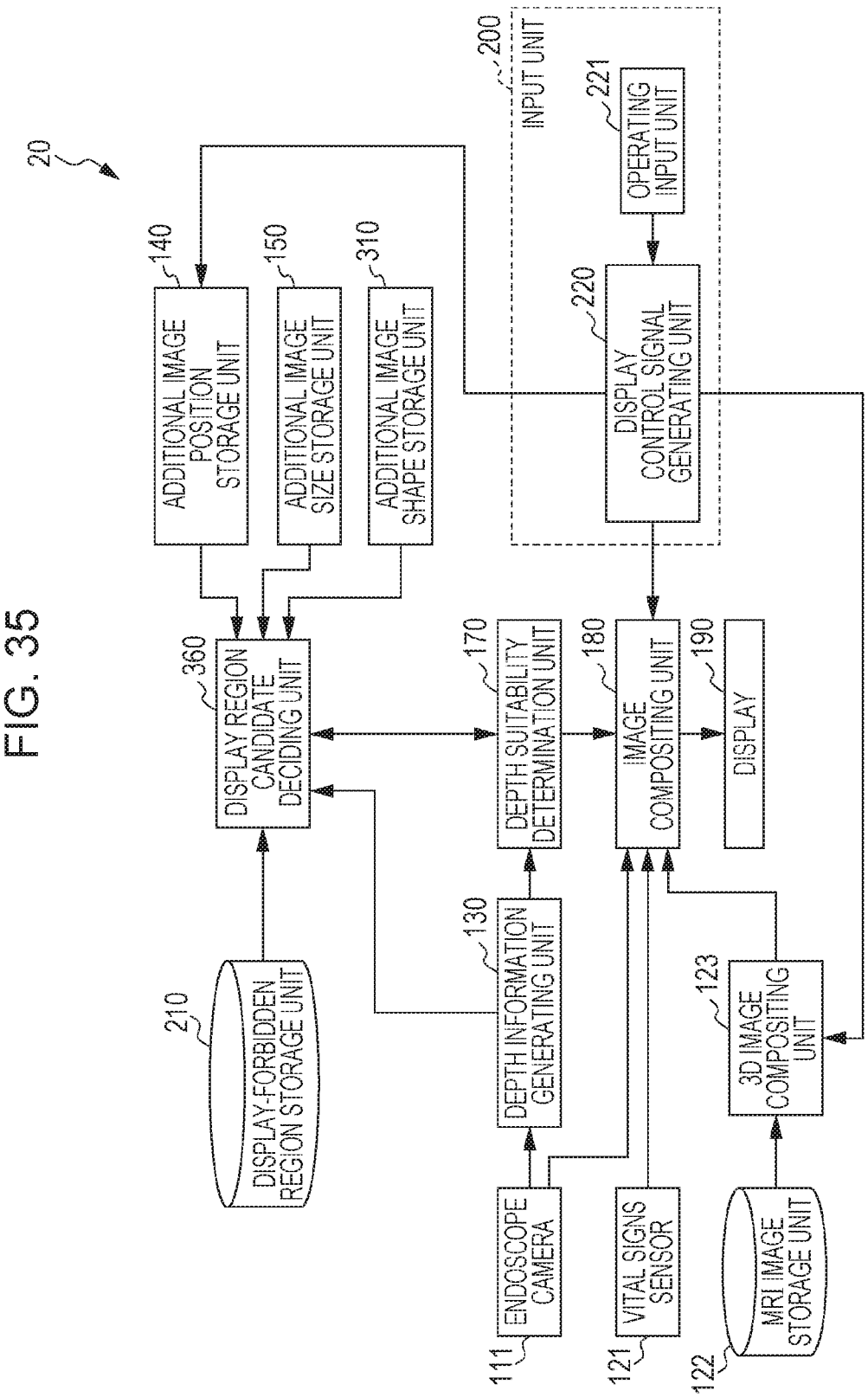
FIG. 35 is a block diagram illustrating a functional configuration of a 3D display device according to a ninth modification of the second embodiment.

FIG. 35 is a block diagram illustrating a functional configuration of the 3D display device 20 according to the ninth modification of the second embodiment. The 3D display device 20 in FIG. 35 is the same as the 3D display device 20 in FIG. 7, except for the points that the display region candidate deciding unit 160 has been replaced with a display region candidate deciding unit 360, an additional image shape storage unit 310 has been added, a display control signal generating unit 220 and operating input unit 221 have been added as the input unit 200, the output of the display control signal generating unit 220 is input to the additional image position storage unit 140, and the output of the depth information generating unit 130 is input to the display region candidate deciding unit 360. Processing units which are the same as those in FIG. 8 are denoted with the same reference numerals, and description thereof will be omitted.

The 3D display device 20 includes the endoscope camera 111, vital signs sensor 121, MRI image storage unit 122, 3D image compositing unit 123, depth information generating unit 130, additional image position storage unit 140, additional image size storage unit 150, additional image shape storage unit 310, display region candidate deciding unit 360, depth suitability determination unit 170, image compositing unit 180, display 190, display-forbidden region storage unit 210, and input unit 200. The input unit 200 includes the display control signal generating unit 220 and the operating input unit 221.

The additional image shape storage unit 310 stores the shape of the additional image display region. In a case where the display region of the additional image is a rectangle, the additional image shape storage unit 310 stores the ratio of the vertical and horizontal sides. In another case, if the additional image display region is an ellipse, the additional image shape storage unit 310 stores the ratio of the major axis and minor axis, or the like, thus storing information by which the shape of the additional image can be decided.

The display region candidate deciding unit 360 decides the position, size, and shape of the additional image display region candidate by referencing information stored in the additional image position storage unit 140, additional image size storage unit 150, additional image shape storage unit 310, and display-forbidden region storage unit 210, and further acquires depth information, generated by the depth information generating unit 130, of the image acquired by the endoscope camera 111 which is the main image.

Operations

Figure 36:
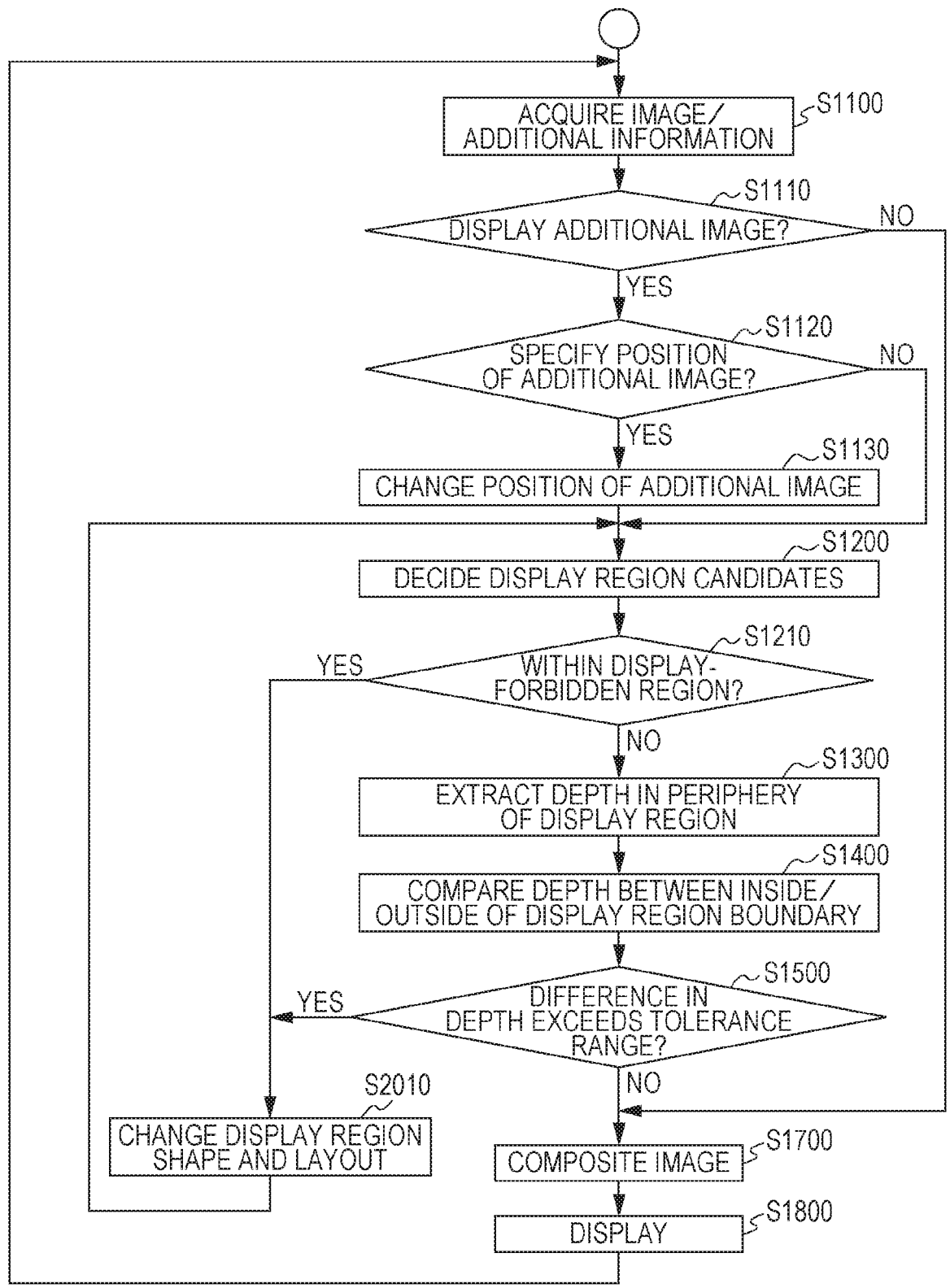
FIG. 36 is a flowchart illustrating processing operations of the 3D display device according to the ninth modification of the second embodiment.

FIG. 36 is a flowchart illustrating the processing operations of the 3D display device 20 according to the ninth modification of the second embodiment. FIG. 36 is the same as FIG. 31, other than step S1620 having been omitted from step S1600, and step S2010 having been added, in the processing operation flowchart of the 3D display device 20. Portions which are the same as those in FIG. 31 will be denoted with the same reference numerals, and description will be omitted. The processing operations of the 3D display device 20 according to the ninth modification of the second embodiment will be described below following FIG. 36.

First, the endoscope camera 111 acquires image information for 3D display having left and right disparity, as a main image, and the vital signs sensor 121 measures the current cardioelectric potential and blood pressure of the patient as additional information (step S1100).

The display control signal generating unit 220 acquires operations which the user has made regarding the additional image at the operating input unit 221, and detects instruction input to display an additional image (step S1110). In a case where additional image display instruction input is detected in step S1110, i.e., in a case where step S1110 yields "yes", the flow advances to step S1120. In a case where additional image display instruction input is not detected in step S1110, i.e., in a case where step S1110 yields "no", the flow advances to step S1700.

In step S1700, the image compositing unit 180 composites an endoscope camera image which is a main image with no additional image as a display image.

In step S1120, the display control signal generating unit 220 further detects input of operating the position of the additional image. In a case where input specifying the position of the additional image is detected in step S1120, i.e., in the case step S1120 yields "yes", the flow advances to step S1130. In a case where input specifying the position of the additional image is not detected in step S1120, i.e., in the case step S1120 yields "no", the flow advances to step S1200.

In step S1130, the display control signal generating unit 220 outputs the information of position of the additional image in the instruction input relating to display of the additional image acquired in step S1110 to the additional image position storage unit 140. The additional image position storage unit 140 stores the information of the position of the additional image which the display control signal generating unit 220 has output (step S1130).

The display region candidate deciding unit 360 decides one candidate for the display region, from the size of the additional image stored in the additional image size storage unit 150, and the position of the additional image stored in the additional image position storage unit 140 (step S1200). For example, the display region candidate deciding unit 360 arbitrarily selects one unselected combination of additional image size stored in the additional image size storage unit 150, and decides a region represented by a combination thereof with the selected additional image position stored in the additional image position storage unit 140, as a display region candidate.

Note that the newest information of the additional image information stored in the additional image position storage unit 140 is used to decide the display region in step S1200. Accordingly, in a case where step S1130 has been executed, the size information recorded in step S1130 is used to decide the display region candidate.

The display region candidate deciding unit 360 determines whether or not the display region candidate decided in step S1200 includes the display-forbidden region stored in the display-forbidden region storage unit 210 (step S1210). In a case where determination is made in step S1210 that the display region candidate includes the display-forbidden region, i.e., in a case where step S1210 yields "yes", the flow advances to step S2010.

In a case where determination is made in step S1210 that the display region candidate does not include the display-forbidden region, i.e., in a case where step S1210 yields "no", the flow advances to step S1300.

The depth suitability determination unit 170 extracts a boundary line or boundary plane of the additional image display region candidate decided in step S1200, and extracts depth information in the periphery of the boundary line or boundary plane (step S1300).

The depth suitability determination unit 170 further compares the depth of the display region of the additional image obtained from the position information of the additional image stored in the additional image position storage unit 140 by the display region candidate deciding unit 360, with the depth of the main image at the portion adjacent to the boundary line or boundary plane of the additional image extracted in step S1300 (step S1400).

The depth suitability determination unit 170 determines whether or not the difference in depth of the main image and additional image displayed across the boundary line or boundary plane exceeds the predetermined tolerance range (step S1500). In a case where determination is made in step S1500 that the difference in depth exceeds the tolerance range, i.e., in a case where step S1500 yields "yes", the flow advances to step S2010. In a case where determination is made in step S1500 that the difference in depth is within the tolerance range, i.e., in a case where step S1500 yields "no", the flow advances to step S1700.

In step S1700, the image compositing unit 180 composites the main image acquired in step S1100 and the additional image representing the additional information acquired in step S1100. Specifically, the image compositing unit 180 displays the main image on the screen of the display 190, and displays the additional image so as to be displayed in the display region on the main image which is the display region candidate decided in step S1200, thus compositing the image.

The display 190 displays the 3D image composited in step S1700 (step S1800), and subsequently the flow returns to step S1100.

In step S2010, the display region candidate deciding unit 360 deforms the shape of the additional image, and stores the deformed shape in the additional image shape storage unit 310. For example, the display region candidate deciding unit 360 deforms the shape of the additional image without changing the display position of the additional image, such that the additional image display region does not include the display-forbidden region, i.e., so that the additional image display region is outside of the display-forbidden region. For example, in a case where the additional image display region is rectangular, and the upper portion of the additional image display region is overlapping the display-forbidden region, the sides of the rectangle in the height direction are shortened, and the sides in the width direction are lengthened, thus deforming the display region into an even more horizontally long shape, so that the additional image does not include the display-forbidden region. Details of the deforming processing of the additional image display region (step S2010) will be described later. After executing step S2010, the flow returns to step S1200.

Repeating steps S1200 through S2010 causes the 3D display device 20 to decide display region candidates while avoiding the display-forbidden region, and further to decide an additional image display region where the difference in depth does not exceed the tolerance range.

Figure 37:
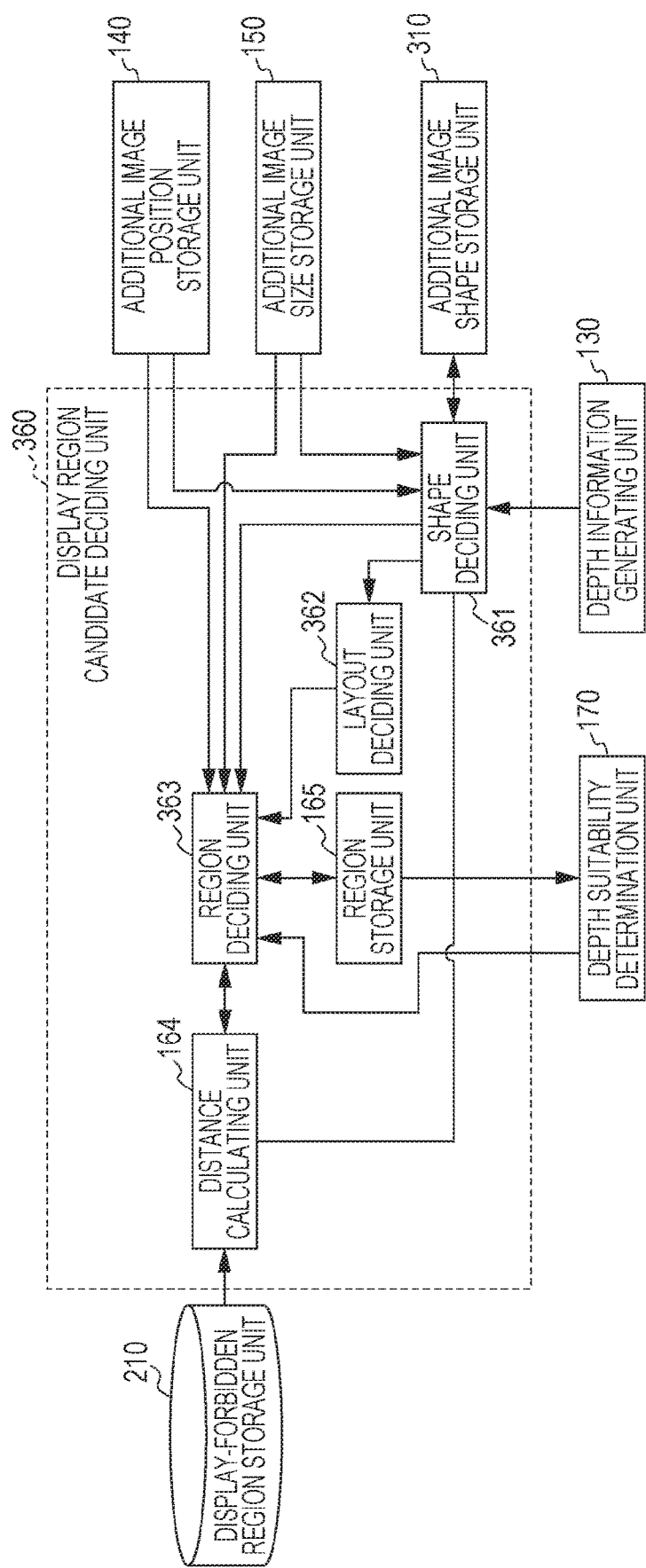
FIG. 37 is a block diagram illustrating a detailed functional configuration of a display region candidate deciding unit according to the ninth modification of the second embodiment.

FIG. 37 is a functional block diagram illustrating part of the 3D display device 20 according to the ninth modification of the second embodiment in detail. The display region candidate deciding unit 360 includes a region deciding unit 363, the distance calculating unit 164, the region storage unit 165, a shape deciding unit 361, and a layout deciding unit 362.

The region deciding unit 363 accepts input from the additional image position storage unit 140, additional image size storage unit 150, shape deciding unit 361, distance calculating unit 164, region storage unit 165, layout deciding unit 362, and depth suitability determination unit 170, and outputs information relating to a display region candidate of the additional image to the distance calculating unit 164 and region storage unit 165. The region deciding unit 363 acquires the display position of the additional image which the user has specified from the additional image position storage unit 140, and acquires the predetermined size of the additional image from the additional image size storage unit 150. The region deciding unit 363 decides the region which the acquired display position and size indicates as being the display region of the additional image. The region deciding unit 363 further follows the input from the distance calculating unit 164, or the input from the depth suitability determination unit 170 and layout deciding unit 362, to deform the display region of the additional image, and adjusts the display layout of the additional information within the deformed display region.

The distance calculating unit 164 calculates the distance between the additional image display region candidate acquired by the region deciding unit 363 and the display-forbidden region stored in the display-forbidden region storage unit 210, in the image display space. For example, the distance calculating unit 164 maps each of the display-forbidden region and the additional image display region candidate in the image display space, onto the display plane, and compare the positions of the two on the display plane, thereby calculating the distance between the two. The distance calculating unit 164 can calculate the distance between the two regions from the difference in x coordinates and y coordinates on the x-y plane in the coordinate system such as illustrated in FIG. 2B, for example. The distance calculating unit 164 outputs the calculation results to the region deciding unit 363.

The region storage unit 165 stores information relating to the additional image display region candidates decided by the region deciding unit 363.

The shape deciding unit 361 decides the shape and size of the additional image display region candidate, based on the distance between the display-forbidden region and the additional image display region candidate obtained by the distance calculating unit 164, the depth information of the 3D image imaged by the endoscope camera 111, which is the main image, acquired from the depth information generating unit 130, the shape information of the additional image stored in the additional image shape storage unit 310, the position of the additional image stored in the additional image position storage unit 140, and the size of the additional image stored in the additional image size storage unit 150. The shape deciding unit 361 outputs the shape and size of the display region candidate that has been decided to the layout deciding unit 362 and the region deciding unit 363.

Figure 38A:
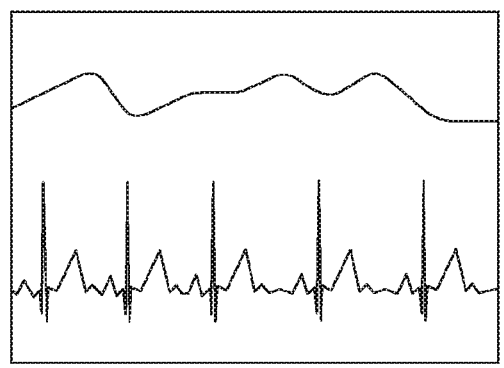
FIG. 38A is a schematic diagram illustrating an example of a layout of an additional image according to the ninth modification of the second embodiment.
Figure 38B:
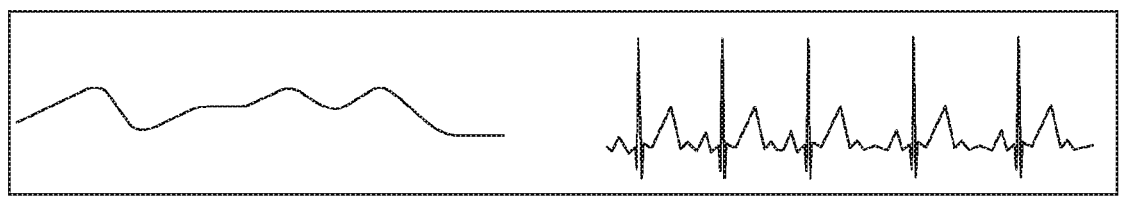
FIG. 38B is a schematic diagram illustrating an example of a layout of an additional image according to the ninth modification of the second embodiment.
Figure 38C:
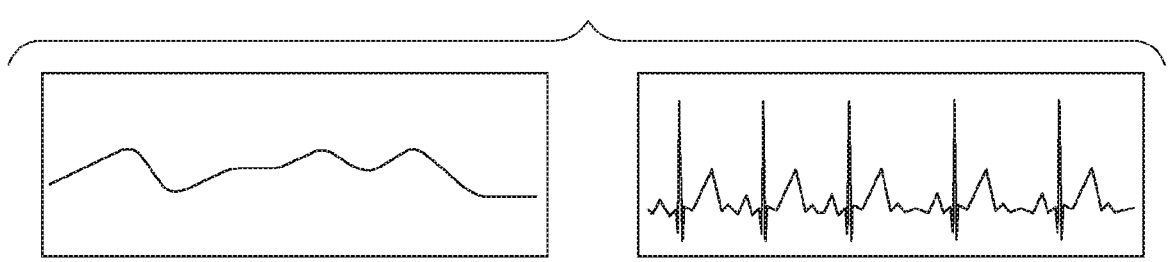
FIG. 38C is a schematic diagram illustrating an example of a layout of an additional image according to the ninth modification of the second embodiment.

The layout deciding unit 362 decides a layout for displaying vital signs information within the additional image display region, according to the shape and size of the display region candidate of the additional image acquired by the shape deciding unit 361. FIG. 38A is a schematic diagram illustrating an example of displaying vital signs information in a standard shape additional image display region. FIG. 38B is a schematic diagram illustrating an example of displaying vital signs information in an additional image display region which is horizontally longer than the standard shape. FIG. 38C is a schematic diagram illustrating an example of displaying vital signs information in two additional image display regions for blood pressure and an electrocardiogram. In a case where the vital signs information are blood pressure and an electrocardiogram, the horizontal axes represents time in both graphs, and in the graph for blood pressure the vertical axis represents pressure while in the graph for the electrocardiogram the vertical axis represents potential. The rectangular display region candidate in FIG. 38A, which is the standard shape, has the two graphs arrayed vertically with the horizontal axes matched, so time temporal synchronization is readily understood. On the other hand, the display region candidate illustrated in FIG. 38B which is long in the horizontal direction allows the two graphs to be observed without vertical compression even for regions where the height is short, by arraying the two graphs horizontally. The arrangement in FIG. 38C displays the two graphs divided into two regions, so the area of each region is small, the degree of freedom of the additional image display positions is high, and the graphs can be readily viewed without excessive compression.

Figure 39:
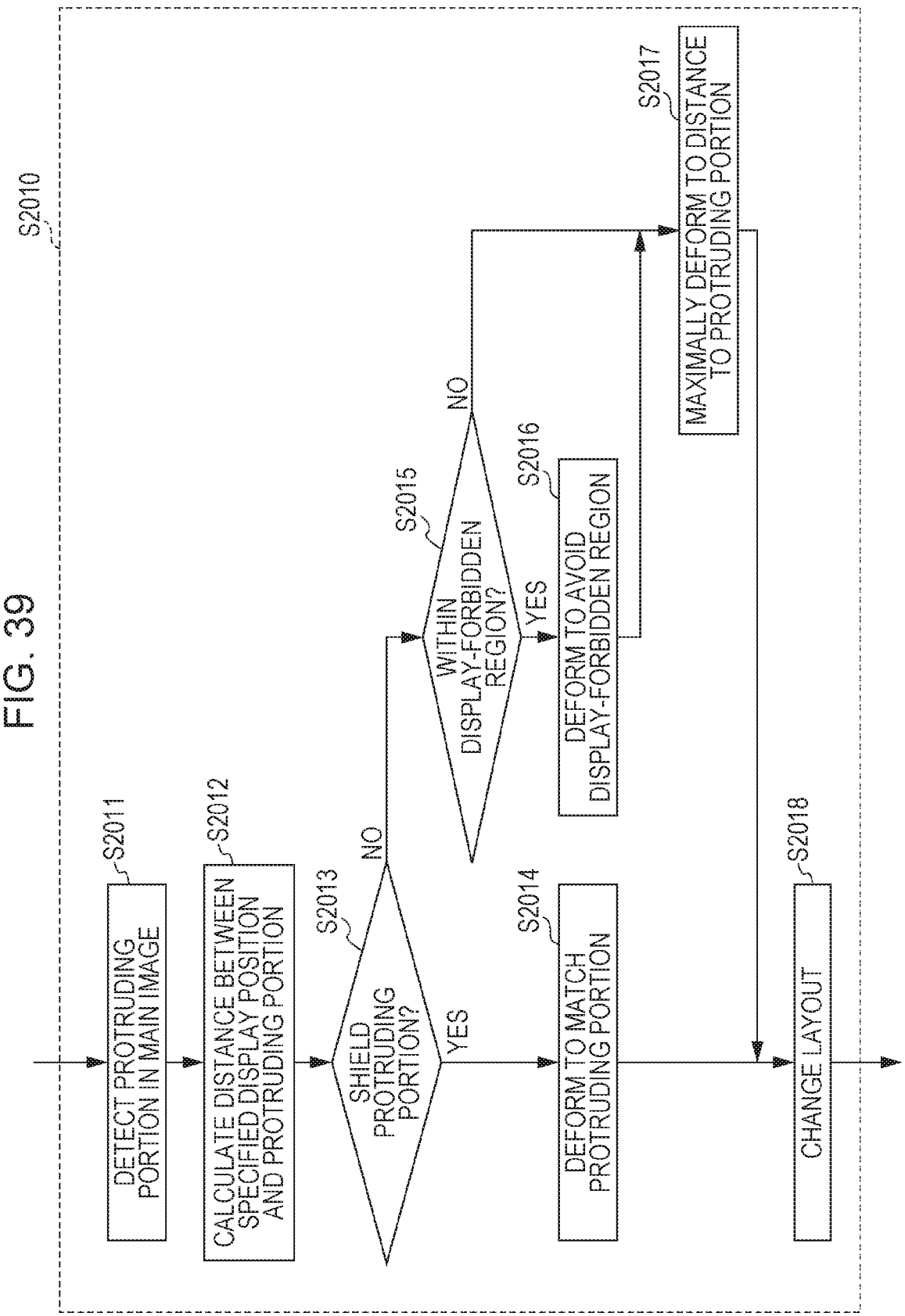
FIG. 39 is a flowchart illustrating processing operations of the display region candidate deciding unit according to the ninth modification of the second embodiment.

FIG. 39 is a flowchart illustrating part of the operations of the 3D display device 20 according to the ninth modification of the second embodiment. The operations of step S2010 will be described with reference to FIG. 39.

In a case where determination is made in step S2010 in FIG. 36 that the display region candidate includes the display-forbidden region, i.e., step S1210 yields "yes", or determination is made in step S1500 that the difference in depth is not within the tolerance range i.e., step S1500 yields "yes", the display region candidate deciding unit 360 performs the operations of step S2010.

First, the shape deciding unit 361 extracts a portion of the image where the amount of protrusion from the screen is great, based on the depth information of the main image acquired from the depth information generating unit 130 (step S2011). Coordinates are set indicating the position of the object in the image as illustrated in FIG. 2B. In a case where a positive value on the depth direction on the z axis represents the direction of protruding from the screen and a negative value represents the far side of the screen, the shape deciding unit 361 extracts an object portion of which the value on the z axis exceeds 50 cm as being a portion where the amount of protrusion is great.

The shape deciding unit 361 calculates the distance between the portion where the amount of protrusion is great that has been extracted in step S2011, and the display region candidate of the additional image (step S2012). For example, the shape deciding unit 361 maps the portion where the amount of protrusion is great and the display region of the additional image on the coordinates x-y plane in FIG. 2B, i.e., on the display plane, and obtains the distance on this plane where the two regions are the closest.

The shape deciding unit 361 determines whether or not to shield the portion where the amount of protrusion is great by the additional image, based on the shape of the portion where the amount of protrusion is great that has been obtained in step S2011, and the distance obtained in step S2012 (step S2013). Examples of cases where determination is made by the shape deciding unit 361 to shield the portion where the amount of protrusion is great by the additional image include a case where the mapped portion to the x-y plane of the portion where the amount of protrusion is great is continuous and the area of the mapped portion is smaller than a predetermined value, a case the mapped portion to the x-y plane of the portion where the amount of protrusion is great is not continuous but the distribution range overlaps any continuous area of the predetermined area, and a case where the portion where the amount of protrusion is great that has been mapped to the x-y plane and the additional image display region candidate mapped to the x-y plane overlap. In a case where determination is made in step S2013 to shield the portion where the amount of protrusion is great by the additional image, i.e., step S2013 yields "yes", the flow advances to step S2014.

In step S2014, the shape deciding unit 361 deforms the region of the additional image so as to be a shape and size including the protruding portion to be shielded. The additional image is a rectangle here. Accordingly, the shape deciding unit 361 takes the distance in the horizontal direction, between the right edge and left edge in the x axis direction in FIG. 2B, of the portion to be shielded on the display plane, i.e., the shape mapped to the x-y plane in FIG. 2B, for example. In the same way, the shape deciding unit 361 takes the distance in the vertical direction, between the top edge and bottom edge in the y axis direction in FIG. 2B, of the portion to be shielded. The shape deciding unit 361 then uses these distances as the length of the height and width sides of the additional image display region following deformation, thus yielding the shape and size thereof.

In a case where determination is made in step S2013 not to shield the portion where the amount of protrusion is great by the additional image, i.e., step S2013 yields "no", the flow advances to step S2015.

In step S2015, the shape deciding unit 361 determines whether or not this additional image display region candidate includes the display-forbidden region, based on this additional image display region candidate calculated by the distance calculating unit 164 and the distance to the display-forbidden region (step S2015). In a case where the additional image display region candidate is determined in step S2015 to include the display-forbidden region, i.e., step S2015 yields "yes", the flow advances to step S2016. In a case where the additional image display region candidate is determined in step S2015 to not include the display-forbidden region, i.e., step S2015 yields "no", the flow advances to step S2017.

In step S2016, the shape deciding unit 361 deforms the shape of the additional image display region candidate, in accordance with the distance between this additional image display region candidate and the display-forbidden region calculated by the distance calculating unit 164. The shape deciding unit 361 performs deformation by changing the length of the long sides and short sides so that the overlapping between the additional image display region and the display-forbidden region is gone, in which the amount of change in the center-of-gravity position of the additional image display region due to the deformation of the additional image display region is minimal.

In step S2017, the shape deciding unit 361 deforms the additional image display region candidate in accordance with the distance between the protruding portion calculated in step S2012 and the additional image display region candidate. For example, the shape deciding unit 361 changes the lengths of the long sides and short sides so that the sum of the distance between all protruding portions adjacent to or overlapping this additional image display region candidate and the this additional image display region candidate is maximal. Alternatively, the shape deciding unit 361 may perform deformation by changing the length of the long sides and short sides to resolve overlapping with protruding portions, in which the amount of change in the center-of-gravity position of the additional image display region due to the deformation of the additional image display region is minimal.

The layout deciding unit 362 changes the display layout of the additional information in accordance with the aspect ratio of the additional image display region candidate deformed in step S2014, step S2016, or step S2017 (step S2018). For example, in a case where the shape of the additional image display region candidate is a rectangle, and the height of the display region is smaller than 8 cm, the layout deciding unit 362 changes the layout to that where multiple graphs having time as the horizontal axis are arrayed horizontally, as illustrated in FIG. 38B. In a case where the height of the display region is 8 cm or longer, the layout deciding unit 362 changes the layout to that where the time axes of the two graphs are matched and arrayed vertically, as illustrated in FIG. 38A.

Description has been made above that in a case where determination is made in step S2015 that the additional image display region includes the display-forbidden region, i.e., step S2015 yields "yes", in step S2016 the shape deciding unit 361 deforms the shape of the display region candidate so as to avoid the display-forbidden region. However, in a case where such deformation would result in the area of the display region candidate being extremely small, equal to or smaller than a predetermined threshold value, the shape deciding unit 361 may transmit a signal to the image compositing unit 180 indicating that the area is extremely small. The image compositing unit 180 responds to the received signal by displaying a message on the display 190 prompting the user to re-specify the display position of the additional image.

As described above, the 3D display device 20 according to the ninth modification of the second embodiment changes the shape of the additional image display region and the layout of the additional information within the display region when the user has specified a display position of the additional image when superimposing the additional image on the 3D image imaged by a stereo endoscope camera. Accordingly, the 3D display device 20 decides the display region of the additional image, avoiding states with great difference in depth between the inside and outside of the boundary of the display region of the additional image, and states with depth contradiction, while also generally following the position specified by the user. Also, shielding the main image by the additional image enables avoiding states with great difference in depth between the inside and outside of the boundary of the display region of the additional image, and states with depth contradiction. This enables the additional image to be displayed at a position which the user, i.e., the surgeon needs, while avoiding depth contradictions such as an additional image which appears to have embedded itself in the arms of the forceps, thereby alleviating fatigue of the user, i.e., the surgeon.

Also note that while description has been made in the ninth modification of the second embodiment that the display region candidate deciding unit 360 changes the layout of the biological data graphs in a case where determination is made that the difference in depth exceeds the tolerance range even if the depth suitability determination unit 170 changes the position of the candidate region, an arrangement may be made where the layout of the biological data graphs is changed in a case where determination is made that the difference in depth exceeds the tolerance range even if the depth suitability determination unit 170 changes the size of the candidate region.

Description has been made in the ninth modification of the second embodiment that the display region of the additional image is deformed such that the additional image shields a portion in the main image where the amount of protrusion is great. Another arrangement which may be made is to change the depth for display of the additional image at the same time as deforming the display region, adjusting the additional image display region so as to minimize the difference in depth between the additional image and the main image at the boundary plane between the additional image and the boundary plane. The phrase "minimize the difference in depth" means to minimize the average difference in depth, or to place the depth position of the additional image at the greatest depth position in the main image side.

Figure 40A:
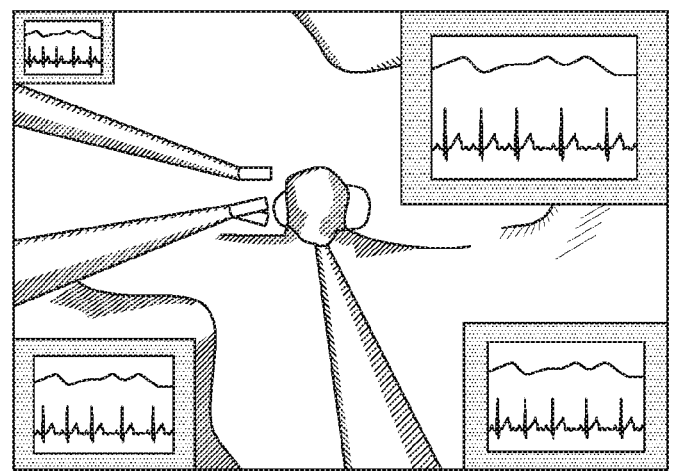
FIG. 40A is a schematic diagram illustrating an example of a case of displaying all display region candidates for additional images according to the fifth through ninth modifications of the second embodiment on a display.

Note that in the fifth through ninth modifications of the second embodiment, the user may select one display region candidate out of the multiple display region candidates decided by the display region candidate deciding unit 160 or the display region candidate deciding unit 360. For example, processing may be added where an additional image is displayed at all display region candidates, and the user uses the input unit 200 to select a particular display region. FIG. 40A is a diagram illustrating a display example where four additional image display region candidates, set by the display region candidate deciding unit 160 or the display region candidate deciding unit 360, are displayed on the screen. In this example, the display region candidates for the additional image are set at positions in contact with the four corners of the display. Each additional image region has the additional image positions fixed to the corners of the display, and the size adjusted so as to not include a region stored in the display-forbidden region storage unit 210 and for the difference in depth within and outside of the additional image display regions to be within the tolerance range, using similar operations to steps S1210 through S1610 in FIG. 31 according to the seventh modification of the second embodiment. The size-adjusted additional image display region candidates are all displayed on the display as illustrated in FIG. 40A, and the user selects a display region which has the most desirable position and size.

Figure 40B:
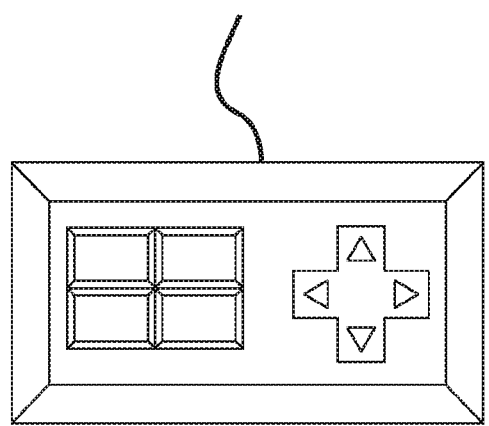
FIG. 40B is a schematic diagram illustrating an example of and operating input unit for displaying all display region candidates for additional images, according to the fifth through ninth modifications of the second embodiment, on a display, and selecting one additional image display region candidate that is displayed.

FIG. 40B is an example of an operating input unit 221 for the user to select a display region candidate. The operating input unit 221 in the example in FIG. 40B has four buttons corresponding to positions on the display, and a D-pad. The user can select press a button corresponding to a display region of which the position and size is most desirable from the four additional image display region candidates, or can use the D-pad to select one of the four additional image display region candidates using the D-pad.

While description has been made in the first through ninth modifications of the second embodiment that the stereo endoscope camera images and vital signs information are acquired and displayed in real-time, an arrangement may be made where images imaged by the stereo endoscope camera and recorded are displayed along with vital signs information acquired and recorded synchronously with the images. In this case, the endoscope camera 111 and vital signs sensor 121 are replaced by an image storage unit and vital signs data storage unit. In a case where images recorded beforehand are to be used, the depth information may be generated beforehand, and stored as data synchronized with the image information.

Third Embodiment

In the second embodiment of the present invention and the modifications thereof, the 3D display device 20 has been described as performing real-time display of images during endoscope surgery, taken with the stereo endoscope camera 111. In a third embodiment, images that have been taken with a stereo endoscope camera and stored are displayed as the main image. Information recorded at the same time as imaging with the stereo endoscope camera during surgery is stored as additional information that has been temporally synchronized with the stereo endoscope camera images.

Configuration

Figure 41:
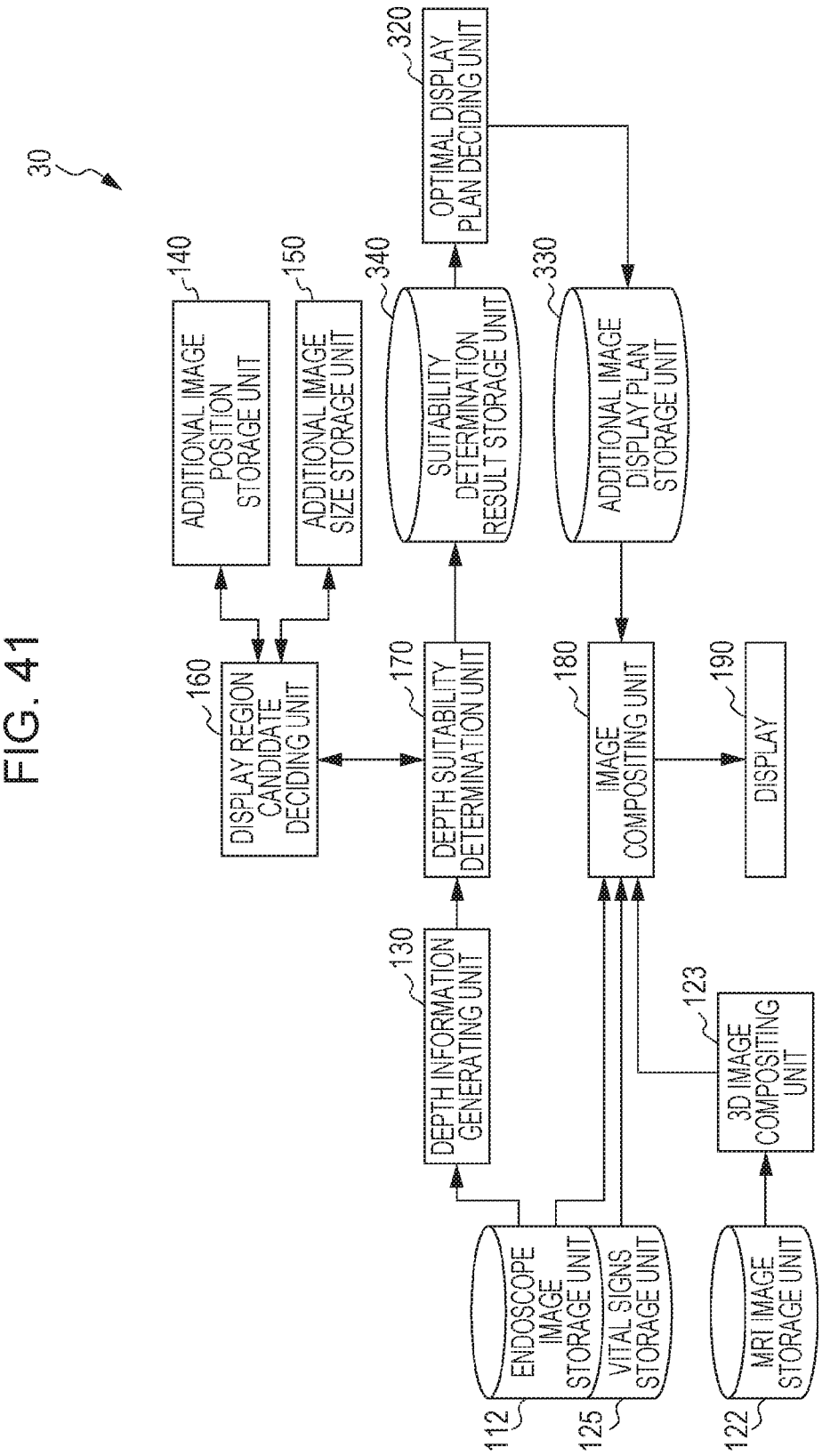
FIG. 41 is a block diagram illustrating a functional configuration of a 3D display device according to a third embodiment.

FIG. 41 is a block diagram illustrating a functional configuration of a 3D display device 30 according to the third embodiment. The configuration is the same as the 3D display device 10 illustrated in FIG. 1, other than the points that the main image acquisition unit 110 has been replaced by an endoscope image storage unit 112, the additional information acquisition unit 120 has been replaced by a vital signs storage unit 125, the MRI image storage unit 122, and the 3D image compositing unit 123, and a suitability determination result storage unit 340, optimal display plan deciding unit 320, and additional image display plan storage unit 330 have been newly added. Other components are the same as those of the 3D display device 20 in FIG. 1. Portions which are the same as those in FIG. 1 are denoted by the same reference numerals, and description will be omitted.

The 3D display device 30 includes the endoscope image storage unit 112, vital signs storage unit 125, MRI image storage unit 122, 3D image compositing unit 123, depth information generating unit 130, additional image position storage unit 140, additional image size storage unit 150, display region candidate deciding unit 160, depth suitability determination unit 170, suitability determination result storage unit 340, optimal display plan deciding unit 320, additional image display plan storage unit 330, image compositing unit 180, and display 190.

The endoscope image storage unit 112 stores images of surgery using a stereo endoscope. The images are stereo 3D images where images of the stereo endoscope camera used in the surgery are stored as moving images, more particularly as a right-eye image and left-eye image which have been temporally synchronized.

The vital signs storage unit 125 stores vital signs information such as body temperature, cardioelectric potential, blood pressure, blood oxygen level, brainwaves, and so forth, measured by sensors attached to the body of the patient during surgery, at the same time as the imaging performed by the endoscope image storage unit 112. The vital signs information is temporally synchronized with the images stored in the endoscope image storage unit 112.

The MRI image storage unit 122 stores 3D image information including images of the affected area to be treated by surgery, which have been recorded by an MRI system before surgery.

The 3D image compositing unit 123 composites image information stored in the MRI image storage unit 122 into images of a format which can be displayed on the display 190, as specified slices or a spectrogram of a specified range.

The depth information generating unit 130 obtains left and right disparity of the 3D images stored in the endoscope image storage unit 112, and generates depth information for the images.

The additional image position storage unit 140 stores the position where the vital signs information stored in the vital signs storage unit 125 or the MRI image information stored in the MRI image storage unit 122 is to be displayed on the screen of the display 190.

The additional image size storage unit 150 stores the size of displaying the additional information acquired by the additional information acquisition unit 120 as an additional image on the screen of the display 190.

The display region candidate deciding unit 160 decides candidates for a display region to display one or a plurality of additional information on the screen of the display 190 as an additional image.

The depth suitability determination unit 170 detects depth difference greater than a predetermined value, or depth contradiction, in the difference in depth between an additional image and the main image at the periphery of the boundary plane of the additional image display region. This detection is made based on information of candidates for a display region decided by the display region candidate deciding unit 160 and depth information of the endoscope image generated by the depth information generating unit 130.

The suitability determination result storage unit 340 stores the value of difference in depth between the additional image and main image which the depth suitability determination unit 170 has determined for each display region candidate at each predetermined time interval.

Figure 42:
FIG. 42 is a diagram illustrating an example of depth difference information for each display region of additional images according to the third embodiment.

FIG. 42 illustrates an example of information stored in the suitability determination result storage unit 340. FIG. 42 illustrates the determination results of the depth suitability determination unit 170 with regard to each additional image display region at each time interval.

The optimal display plan deciding unit 320 searches the information stored in the suitability determination result storage unit 340 for results which the has determined regarding the images stored in the endoscope image storage unit 112 at all time intervals. The optimal display plan deciding unit 320 selects an optimal display region for each time interval, from the display region candidates at each time interval. The optimal display plan deciding unit 320 decides the selected optimal additional image display region for each time interval of the images stored in the endoscope image storage unit 112 to be a display plan. Deciding of the optimal display region is performed based on determination standards such as additional images where the number of times of display position change is the least throughout all time intervals, additional images where the amount of display position change is the least throughout all time intervals, and so forth, for example. The display plan which the optimal display plan deciding unit 320 decides is stored in the additional image display plan storage unit 330.

The image compositing unit 180 displays the 3D image stored in the endoscope image storage unit 112 on the screen of the display 190, and composites an image such that the vital signs information stored in the vital signs storage unit 125 and the MRI image information stored in the MRI image storage unit 122 are displayed at the additional image display regions at each time indicated by the display plan stored in the additional image display plan storage unit 330. The display 190 displays the generated image.

Operations

Figure 43:
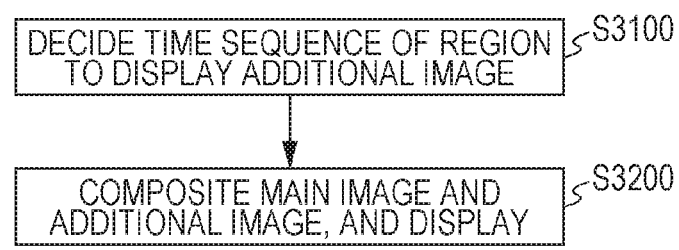
FIG. 43 is a flowchart illustrating partial operations of processing operations of the 3D display device according to the third embodiment.
Figure 44:
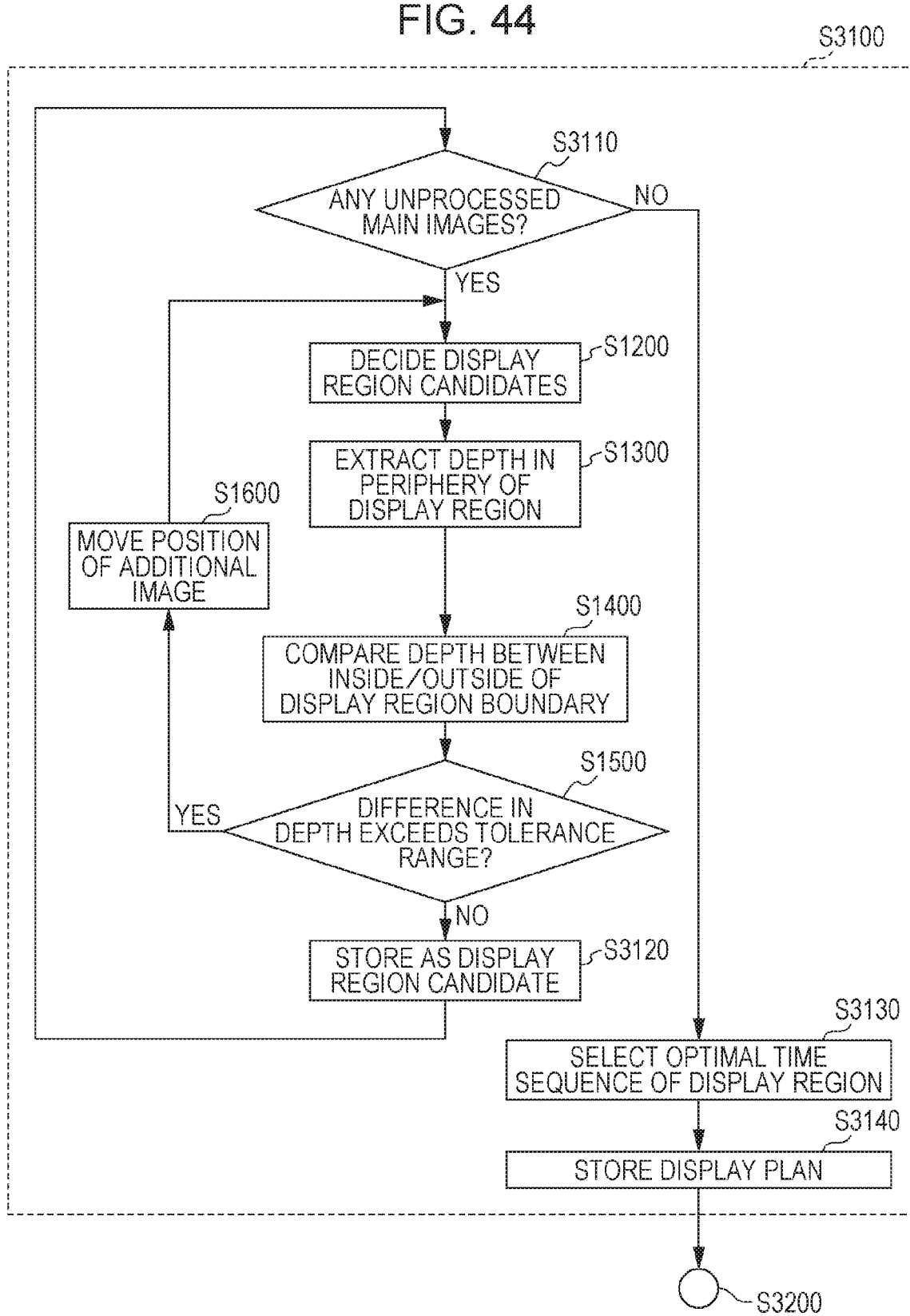
FIG. 44 is a flowchart illustrating detailed partial operations of processing operations of the 3D display device according to the third embodiment.
Figure 45:
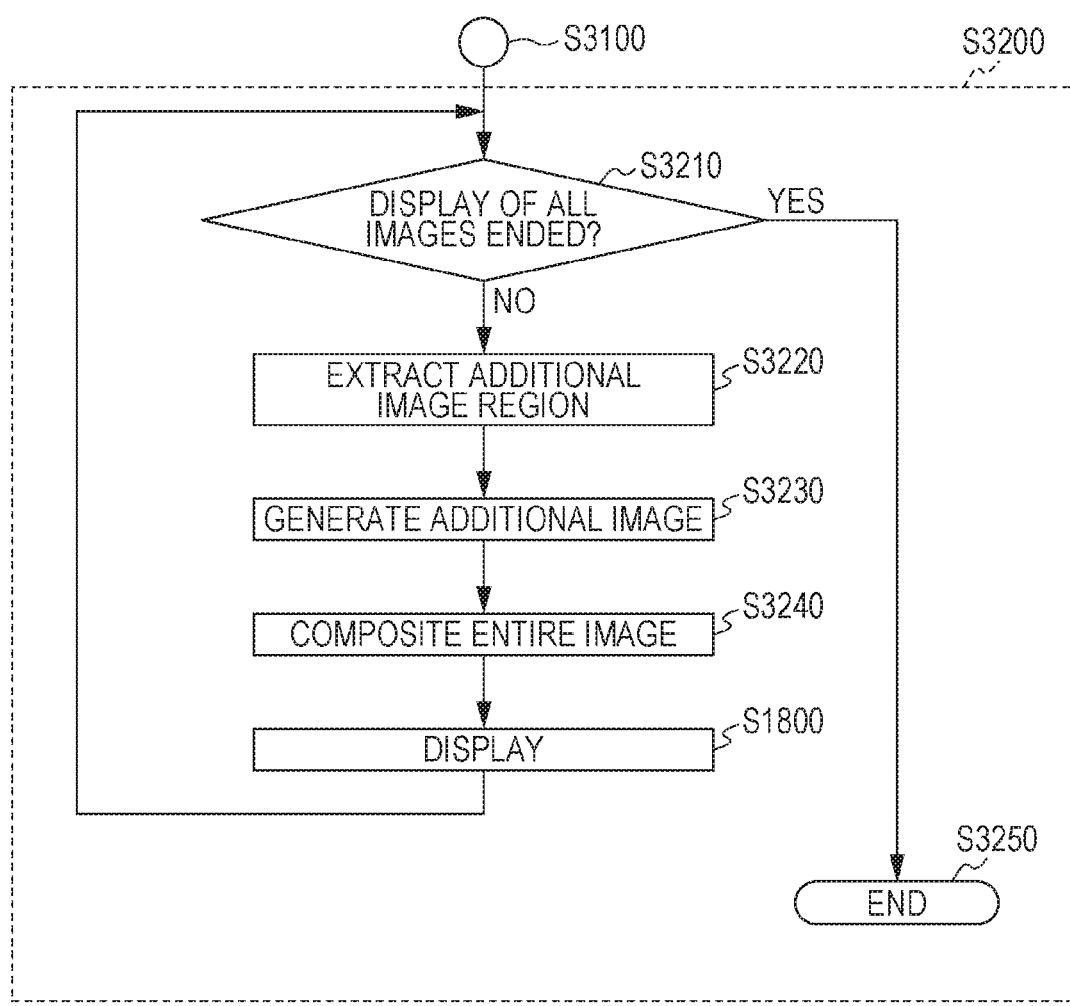
FIG. 45 is a flowchart illustrating detailed partial operations of processing operations of the 3D display device according to the third embodiment.

FIG. 43 is a flowchart illustrating operations of the 3D display device 30 according to the third embodiment. FIGS. 44 and 45 are flowcharts illustrating a part of operations of the 3D display device 30 according to the third embodiment in detail. The operations of the 3D display device 30 according to the third embodiment will be described with reference to FIGS. 41 and 43 through 45.

The 3D display device 30 first decides the time sequence of the display regions of additional images to be displayed along with the images stored in the endoscope image storage unit 112 serving as the main image (step S3100). Next, the 3D display device 30 actually composites the main image and additional image, and displays the composited 3D image (step S3200).

Detailed operations of step S3100 will be described next. Referring to FIG. 44, the depth information generating unit 130 acquires an image for a unit time to be processed, from the 3D images stored in the endoscope image storage unit 112, ad determines whether or not there are unprocessed images remaining in the endoscope image storage unit 112 (step S3110). A unit time for processing is one sample of a digital moving image, for example. In a case where determination is made in step S3100 that there is an unprocessed image remaining in the endoscope image storage unit 112 (yes in step S3110), the flow advances to step S1200. In a case where determination is made in step S3110 that there are no unprocessed images remaining in the endoscope image storage unit 112 (no in step S3110), the flow advances to step S3130.

The display region candidate deciding unit 160 decides in step S1200 the candidates for the display region, from the size of the additional image stored in the additional image size storage unit 150, and the position of the additional image stored in the additional image position storage unit 140 (step S1200).

The depth information generating unit 130 generates depth information of images in processing units acquired from the endoscope image storage unit 112 (step S1300).

The depth suitability determination unit 170 compares the depth of the display region obtained from the information stored in the additional image position storage unit 140 with the depth of the main image at the portion adjacent to the boundary line or boundary plane of the additional image extracted in step S1300 (step S1400).

The depth suitability determination unit 170 determines whether or not the difference in depth of the main image and additional image displayed across the boundary line or boundary plane (step S1500). In a case where determination is made in step S1500 that the difference in depth exceeds the tolerance range, i.e., in a case where step S1500 yields "yes", the flow advances to step S1600. In a case where determination is made in step S1500 that the difference in depth is within the tolerance range, i.e., in a case where step S1500 yields "no", the flow advances to step S3120.

In step S1600, the display region candidate deciding unit 160 moves the display position of the additional image, and stores the moved display position in the additional image position storage unit 140 (step S1600). After step S1600, the flow returns to step S1200.

In step S3120, the depth suitability determination unit 170 stores, in the suitability determination result storage unit 340, time information of synchronizing with the main image stored in the endoscope image storage unit 112, region information of additional image display region candidates, and difference in depth between the main image and additional image displayed across the region boundary line or boundary plane of the additional image obtained in step S1400. The stored contents are configured as illustrated in FIG. 42, for example. After step S3120, the flow returns to step S3110.

Repeating steps S3110 through S3120 stores additional image display region candidates for each unit time, for all time intervals of images stored in the endoscope image storage unit 112.

In step S3130, the optimal display plan deciding unit 320 decides a display region to display an additional image for each time interval, out of the additional image display region candidates for each time interval stored in the suitability determination result storage unit 340. The method of selecting the additional image display region may be selecting an additional image display region at each time so that the number of times of movement of the additional image display region as to the main image in the overall time is the least.

Another method of selecting the additional image display region may be to select an additional image display region at each time so that the total amount of movement of the additional image display region as to the main image in the overall time is the least. Optimization may also performed using a standard which combines the number of times of movement and the distance of movement. The optimal display plan deciding unit 320 stores the additional image display region for each time interval that has been optimized in this way, i.e., the display plan of the additional images, in the additional image display plan storage unit 330 (step S3140).

Performing processing of steps S3110 through S3140 decides all additional image display regions for superimposed display on the main image, for all time intervals of the main images stored in the endoscope image storage unit 112.

Next, detailed operations in step S3200 will be described with reference to FIG. 45. The image compositing unit 180 acquires images in it time for display from the stereo 3D images stored in the endoscope image storage unit 112, and determines whether or not all images in the endoscope image storage unit 112 have been displayed (step S3210). In a case where determination is made that not all images have been displayed (no in step S3210), the flow advances to step S3220. In a case where determination is made that not images have been displayed (yes in step S3210), the flow advances to step S3250.

In step S3220 the image compositing unit 180 acquires an additional image display region from the additional image display plan storage unit 330 corresponding to this time interval.

In step S3230 the image compositing unit 180 acquires vital signs information from the vital signs storage unit 125 corresponding to this time interval. The image compositing unit 180 also follows a display template to generate an image in the additional image display region acquired in step S3220. The display template is a template of a graph in which the horizontal axis represents time, for example, and the vertical axis represents values such as body temperature, blood pressure, and so forth. The image compositing unit 180 further acquires, from the 3D image compositing unit 123, stereo 3D image information generated as computer graphics based on the information stored in the MRI image storage unit 122. The image compositing unit 180 generates computer graphics images within the additional image display region acquired in step S3220 (step S3230).

The image compositing unit 180 composites the additional image generated in step S3230 with the main image acquired in step S3210, thereby generating an entire image (step S3240).

The display 190 displays the image generated in step S3240 (step S1800).

Repeating steps S3210 through S1800 enables all additional images corresponding to images stored in the endoscope image storage unit 112 to be displayed. Upon all images recorded in the endoscope image storage unit 112 being displayed, the operations of the 3D display device 30 end (step S3250).

Advantages and Effects

As described above, the 3D display device 30 according to the present embodiment decides display regions for additional images when displaying additional images over or adjacent to 3D images, such that states where there is a great difference in depth between within and outside the boundary of the additional image display region, or states where there is depth contradiction are avoided. Accordingly, user discomfort and fatigue due to excessive difference in depth and depth contradiction can be prevented. Further, the additional image display regions are optimized over all display time intervals of the main image and additional images, so the load on the user due to the additional image display regions frequently moving or moving great distances can be avoided, and user fatigue can be prevented.

The display region candidate deciding unit 160 has been described as deciding the display region candidates based on information stored in the additional image position storage unit 140 and additional image size storage unit 150 in the third embodiment. However, an arrangement may be made such as in the second embodiment, and second, third, and fourth modifications of the second embodiment, where the display-forbidden region storage unit 210 stores information of regions where shielding by additional images is forbidden, and a region which would shield the affected area which is to be treated by surgery is not set as an additional image display region.

Also, while description is made in the third embodiment that additional images are automatically displayed and the user does not operate the additional image, an arrangement may be made such as in the second embodiment, and the second modification of the second embodiment, where the user inputs operations as to the additional image from the input unit 200, so as to change the region of the additional image.

Further, while description is made in the third embodiment that the additional image display regions are selected for each time interval, such that the number of times of movement of the total distance of movement of the additional image display regions as to the recoded main image is the least, the following processing may be performed so that the number of times of movement of the total distance of movement of the additional image display regions is the least in the main image imaged in real-time as described in the first and second embodiments as well. For example, at the time of deciding an additional image display region candidate, the display region candidate deciding unit 160 illustrated in FIG. 1 may decides the additional image display region candidate giving priority to a display position closest to the display region of the additional image that was displayed immediately prior.

Fourth Embodiment

In the second embodiment, the modifications thereof, and the third embodiment, the main image has been described as being an image imaged by a stereo endoscope camera, and the additional images as being images of vital signs information temporally synchronized with the main image, and images acquired beforehand such as MRI images and so forth. On the other hand, in a 3D display device according to a fourth embodiment, images imaged by a stereo camera attached to a remotely-operated robot serve as the main image, and a map of the current position generated from map information of an operating range of this robot, and current position information of the robot, serve as the additional images. An operator of the remotely operated robot monitors the 3D display device. The 3D display device 40 may display, in addition to a map of the current position, an image of information of the surrounding environment, such as air temperature, humidity, air pressure, amount of radiation, and so forth, in the environment in which the robot is operating, as the additional image. In a case of displaying an image of information of the surrounding environment as an additional image, this may be displayed as a graph or the like as with the vital signs information images in the second embodiment.

Configuration

Figure 46:
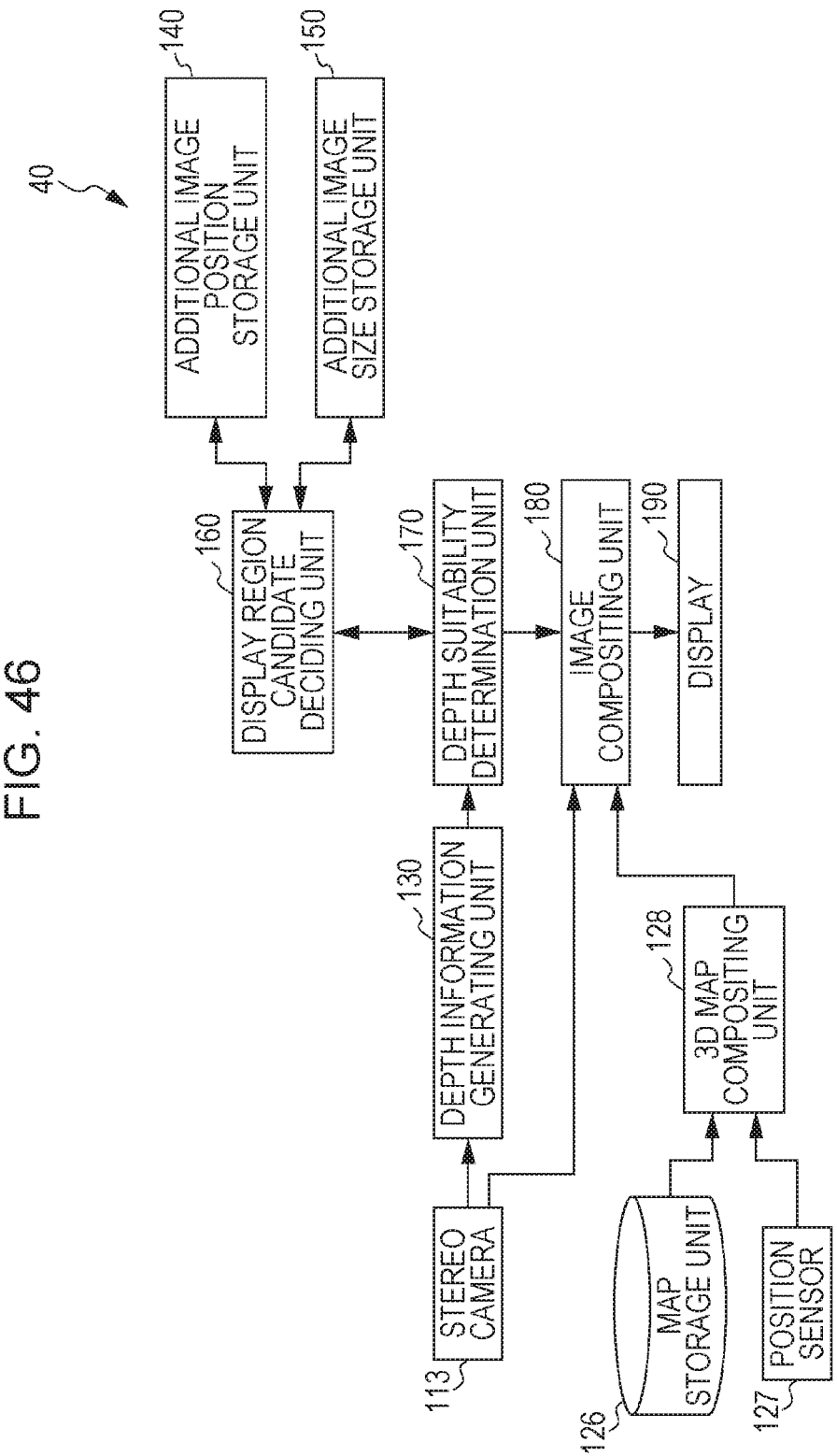
FIG. 46 is a block diagram illustrating a functional configuration of a 3D display device according to a fourth embodiment.

FIG. 46 is a block diagram illustrating a functional configuration of the 3D display device 40 according to the fourth embodiment. The configuration in FIG. 46 is the same as the 3D display device 10 according to the first embodiment illustrated in FIG. 1, other than the points that the main image acquisition unit 110 has been replaced by a stereo camera 113, and the additional information acquisition unit 120 has been replaced by a map storage unit 126, position sensor 127, and 3D map compositing unit 128. Other configurations are the same as with the 3D display device 10 in FIG. 1. Portions which are the same as those in FIG. 1 are denoted by the same reference numerals, and description will be omitted.

The 3D display device 40 includes the stereo camera 113, map storage unit 126, position sensor 127, 3D map compositing unit 128, depth information generating unit 130, additional image position storage unit 140, additional image size storage unit 150, display region candidate deciding unit 160, depth suitability determination unit 170, image compositing unit 180, and display 190.

The stereo camera 113 is a camera for stereo 3D imaging, attached to the remotely operated robot.

The map storage unit 126 stores map information of a range where the robot operates. The map is, for example, a blueprint of a particular building, for example, and includes information of rooms on each floor.

The position sensor 127 is a sensor that measures the current position of the remotely operated robot. A specific example is a global positioning satellite (GPS) system sensor and an altimeter, for example. The GPS sensor measures the lateral position, and the altimeter measures the floor in the building.

The 3D map compositing unit 128 composites an image indicating the current position of the robot, on an image within the building displayed in 3D, based on the map information stored in the map storage unit 126 and the position information of the robot measured by the position sensor 127. The 3D map compositing unit 128 generates an image which displays the structures of the building such as walls for example, in a semi-transparent form, and the robot represented by a triangular post or the like, so that the front and back directions can be comprehended.

The depth information generating unit 130 obtains left and right disparity of the 3D images imaged by the stereo camera 113, and generates depth information for the images.

The additional image position storage unit 140 stores the position for displaying the images composited at the 3D map compositing unit 128 on the screen of the display 190.

The additional image size storage unit 150 stores the size of displaying the images composited at the 3D map compositing unit 128 on the screen.

The display region candidate deciding unit 160 decides candidates for a display region to display one or a plurality of additional information on the screen as an additional image.

The depth suitability determination unit 170 detects depth difference greater than a predetermined value, or depth contradiction, in the difference in depth between an additional image and the main image at the periphery of the boundary plane of the additional image display region. This detection is made based on information of candidates for a display region decided by the display region candidate deciding unit 160 and depth information of the 3D image generated by the depth information generating unit 130.

The image compositing unit 180 composites the 3D image imaged by the stereo camera 113 and the image composited at the 3D map compositing unit 128, so as to generated an image to be displayed on the display 190. The display 190 displays the image generated by the image compositing unit 180.

Operations

Figure 47:
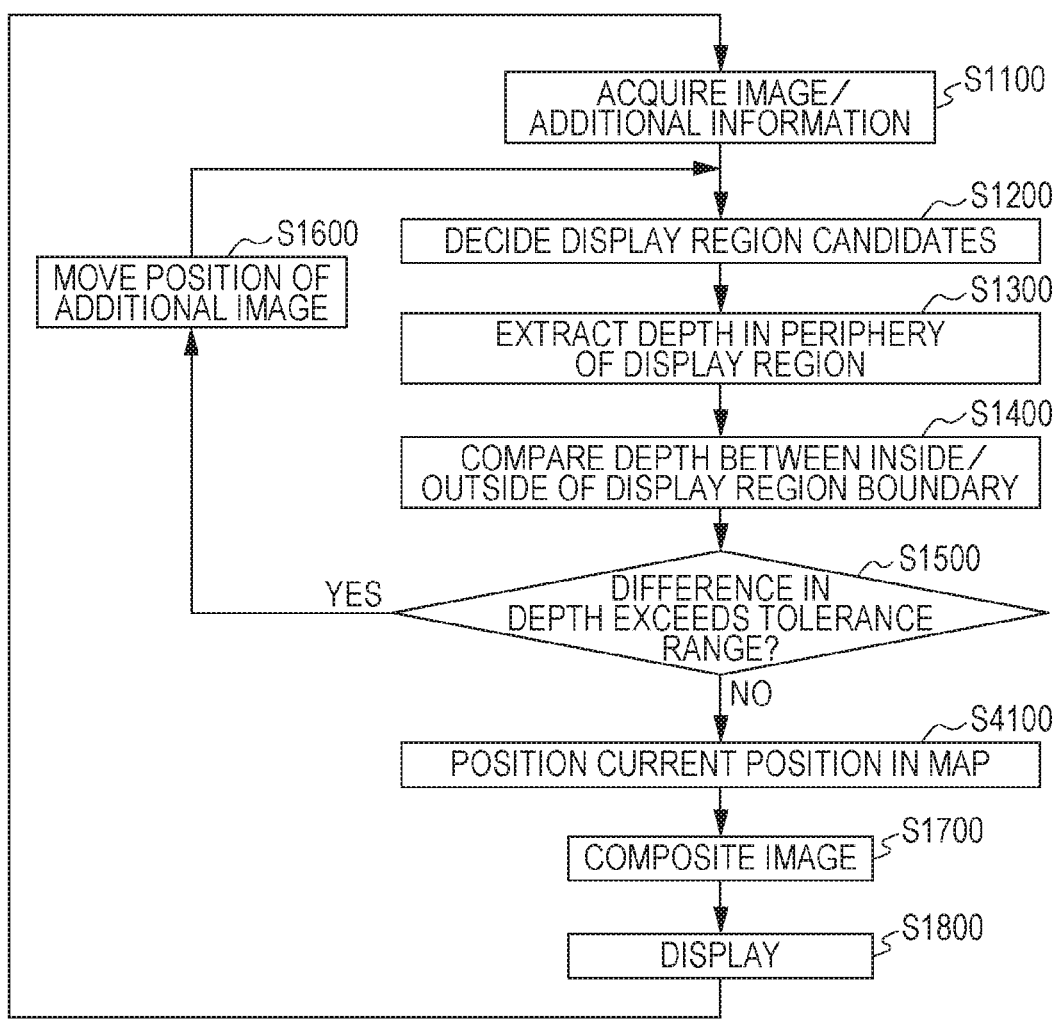
FIG. 47 is a flowchart illustrating processing operations of the 3D display device according to the fourth embodiment.

FIG. 47 is a flowchart illustrating processing operations of the 3D display device 40 according to the fourth embodiment. FIG. 47 is the same as FIG. 5 in the first embodiment, other than step S4100 having been added to the operations illustrated in FIG. 5. The operations of the 3D display device 40 according to the fourth embodiment will be described with reference to FIGS. 46 and 47.

First, the stereo camera 113 acquires image information for 3D display that has left and right disparity, and the position sensor 127 acquires information of the current position of the robot (step S1100). The current position information includes lateral position and altitude information.

Next, the display region candidate deciding unit 160 decides candidates for the display region, based on the predetermined size of the additional image stored in the additional image size storage unit 150 and the position of the additional image stored in the additional image position storage unit 140 (step S1200). In the fourth embodiment, one additional image size is stored in the additional image size storage unit 150, and one or a plurality of position information is stored in the additional image position storage unit 140.

The depth suitability determination unit 170 extracts a boundary line or boundary plane of the display region candidate of the additional image decided in step S1200. A boundary plane is a depth-direction face orthogonal to the plane of the display 190. The depth suitability determination unit 170 identifies a portion in the 3D image acquired in step S1100 in contact with the boundary line or boundary plane of the additional image, and extracts depth information (step S1300). The depth information generating unit 130 generates and holds the depth information of the main image by the time that the main image acquisition unit 110 acquires the main image in step S1100 and the depth suitability determination unit 170 extracts the depth information in step S1300.

Further, the depth suitability determination unit 170 compares the depth of the display region of the additional image obtained by the information of the position of the additional image stored in the additional image position storage unit 140 by the display region candidate deciding unit 160, with the depth of the main image at a portion in contact with the boundary line or boundary plane of the additional image extracted in step S1300 (step S1400).

The depth suitability determination unit 170 determines whether or not the difference in depth between the main image and additional image displayed across the boundary lines or boundary plane exceeds a predetermined tolerance range (step S1500). The difference in depth is a value obtained by subtracting the depth value of the main image nearby the boundary line from the depth value of the additional image, and the tolerance range thereof is −1 cm to 15 cm, for example. In a case where determination is made in step S1500 that the difference in depth exceeds the tolerance range, i.e., step S1500 yields a result of "yes", the flow advances to step S1600. On the other hand, in a case where determination is made in step S1500 that the difference in depth is within the tolerance range, i.e., step S1500 yields a result of "no", the flow advances to step S4100.

The display region candidate deciding unit 160 changes the display position of the additional image (step S1600). Changing of the display position is performed by selecting, from display positions stored in the additional image position storage unit 140, a display position not selected as a display position candidate in step S1200. After step S1600, the flow returns to step S1200.

In step S4100 the 3D map compositing unit 128 generates 3D computer graphics of the building, based on structure information of the building stored in the map storage unit 126, and renders the current position of the robot in the generated computer graphics of the building. The 3D map compositing unit 128 calculates the coordinate position corresponding to the current position of the robot within the building, based on the lateral position and altitude of the robot acquired from the position sensor 127, and places a symbol representing the robot at this coordinate position in the computer graphics of the building, such as a triangular post for example.

Thereafter, image compositing unit 180 composites the image, by displaying the map and the current position of the robot generated in step S4100 upon the stereo image acquired in step S1100, as the display region from the display region candidate decided in step S1200.

The display 190 displays the 3D image composited in step S1700 (S1800). After displaying the 3D image on the display 190 in step S1800, the flow returns to step S1100. Repeating steps S1100 through S1800 causes the 3D display device 40 to acquire images and additional information in increments of processing, and continue displaying of 3D images.

Advantages and Effects

As described above, the 3D display device 40 according to the present embodiment decides display regions for additional images when displaying additional images over or adjacent to 3D images, such that states where there is a great difference in depth between within and outside the boundary of the additional image display region, or states where there is depth contradiction are avoided. Accordingly, user discomfort and fatigue due to excessive difference in depth and depth contradiction can be prevented even when displaying 3D images of computer graphics on top of a 3D main image.

Note that the components in the above-described embodiments may each be carried out in the form of dedicated hardware, or may be carried out by executing a software program suitable for that component. The components may be carried out by a program executing unit of a central processing unit (CPU) or some other processor reading out and executing a software program recorded in a recording medium such as a hard disk, semiconductor memory, or the like.

While a 3D display device according to one or multiple aspects has been described by way of embodiments, the present disclosure is not restricted by these embodiments. Various modifications of the embodiments and combinations of components of different embodiments may be made by one skilled in the art without departing from the essence of the present disclosure, all of which may be encompassed within the scope of one or multiple aspects. The above-described embodiments primarily contain the disclosure according to the following aspects.

According to an aspect of the present disclosure, a three-dimensional display device includes: a display region candidate deciding unit that decides one candidate region from a plurality of display region candidates of an additional image which shields part of a main image of a three-dimensional image on a screen; a depth suitability determination unit that determines, in a case of assuming that the additional image is to be displayed in the candidate region which the display region candidate deciding unit has decided, whether or not a difference in depth between depth of the main image displayed at a boundary region which is a region on the main image and within a predetermined distance from a boundary line of the candidate region, and the depth of the additional image, is within a predetermined tolerance range; an image compositing unit that, in a case where determination is made by the depth suitability determination unit that the difference in depth is within the tolerance range, superimposes the additional image upon the candidate region on the main image, thereby compositing the main image and the additional image, and displays an image obtained as a result of the compositing on the screen; and a possibly-unsuitable region deciding unit that decides, in the main image, a first region that has a possibility of the depth protruding to a near side beyond a predetermined depth range, and a second region that has a possibility of the depth recessing to a far side beyond a predetermined depth range. The display region candidate deciding unit further decides a candidate region to shield the first region and the second region decided by the possibly-unsuitable region deciding unit.

According to this aspect, in a case where the difference in depth between the main image and additional image across the boundary line of the additional image is within the tolerance range, the additional image is displayed. Displaying the additional image in a region protruding excessively enables depth contradiction occurring as a result to be resolved. Accordingly, user discomfort and fatigue can be prevented.

In a case of the depth suitability determination unit determining that the difference in depth is not within the tolerance range, the candidate region may be re-decided.

In this case, a candidate region where the difference in depth is within the tolerance range is decided. Accordingly, user discomfort and fatigue due to excessively large difference in depth between the main image and additional image, and depth contradiction, can be prevented.

The depth suitability determination unit may divide the boundary region into partial regions of a predetermined number, calculate a difference in depth between the depth of the main image displayed at the partial region and the depth of the additional image for each partial region, and determine whether or not a maximum value of the calculated difference in depth is within the tolerance range, thereby determining whether or not the difference in depth between the depth of the main image displayed in the boundary region and the depth of the additional image is within the predetermined tolerance range.

The image compositing unit may, in a case where determination is made by the depth suitability determination unit that the difference in depth is within the tolerance range, composite an image where the additional image having a first frame is superimposed on the candidate region on the main image, and display the composited image on the screen, and in a case where determination is made by the depth suitability determination unit that the difference in depth is not within the tolerance range, composite an image where the additional image having a second frame, which is broader than the first frame, is superimposed on the candidate region on the main image, and displays the composited image on the screen.

In this case, providing a broad frame can prevent user discomfort and fatigue, even in a case where the difference in depth is great and the difference in depth is not within the tolerance range.

The three-dimensional display device may further include a display-forbidden region storage unit that stores a display-forbidden region, which is a region on the screen where display of the additional image is forbidden. The display region candidate deciding unit may decide one candidate region from the plurality of display region candidates of the additional image, which does not overlap the display-forbidden region stored in the display-forbidden region storage unit. This prevents important portions in the main image from being shielded from view by the additional image.

The depth suitability determination unit may adds a correction value, which is larger the closer a distance from the candidate region to the display-forbidden region is, to the difference in depth, and thereupon determine whether or not the difference in depth is within the tolerance range.

In this case, candidate regions which are farther from the display-forbidden region are more readily selected even if the difference in depth thereof is the same.

The shorter a distance between a camera which has imaged the main image and an object displayed in the display-forbidden region is, the larger the size of the display-forbidden region may be.

In this case, the closer the distance is, the larger the object is displayed in the screen. Accordingly, the size of the display-forbidden region is changed in accordance with the size of the object.

The three-dimensional display device may further include a possibly-unsuitable region storage unit that writes the first region and the second region to the possibly-unsuitable region storage unit as a possibly-unsuitable region.

The display region candidate deciding unit may decide the candidate region giving priority to a candidate at a position closest to the display region of the additional image displayed on the screen immediately prior. In this case, the position of the display region of the additional image can be prevented from greatly changing.

The three-dimensional display device may further include an optimal display plan deciding unit that decides a candidate region at predetermined time intervals, from candidate regions regarding which the difference in depth is within the tolerance range according to the determination results of the depth suitability determination unit regarding whether or not the difference in depth between the depth of the main image and the depth of the additional image is within the tolerance range, for each of the plurality of candidates of the display region of the additional image, at every predetermined time interval, so that from the start of displaying the main image, which is a prerecorded three-dimensional image, to ending of displaying, the distance of movement or number of times of movement of the display region of the additional image is smallest. The image compositing unit may composite an image where the additional image is superimposed on the main image, such that the additional image is displayed at the candidate region for each predetermined time interval decided by the optimal display plan deciding unit, and display the composited image on the screen.

In this case, the position of the display region of the additional image can be prevented from greatly changing when playing a recorded main image.

The main image may be a three-dimensional image imaged by an endoscope camera. In this case, the 3D display device can be used for endoscope surgery.

The three-dimensional display device may further include a display-forbidden region storage unit that stores a display-forbidden region, which is a region on the screen where display of the additional image is forbidden. The display region candidate deciding unit may decide one candidate region from the plurality of display region candidates of the additional image, which does not overlap the display-forbidden region stored in the display-forbidden region storage unit, and the display-forbidden region may be a region of the main image including an image of an affected area to be treated by surgery.

In this case, a situation can be prevented where the image of the affected area is hidden by the additional image, impeding the surgery.

The additional image may be an image indicating at least one of blood pressure, blood oxygen level distribution, respiration, expiration, body temperature, cardioelectric potential, brainwaves, and pulse waves, of the patient during surgery.

In this case, an additional image indicating additional information necessary for surgery can be displayed on the screen, thus supporting the surgeon in performing the surgery.

The three-dimensional display device may further include an input unit that accepts instruction of at least one of a position and a size of the display region of the additional image displayed on the screen. The display region candidate deciding unit may decide a candidate region for the display region of the additional image, based on the instruction which the input unit has accepted.

In this case, an additional image is displayed in a case where the difference in depth between the main image and additional image across a boundary line of the additional image is within the tolerance range. Accordingly, user discomfort and fatigue due to excessively large difference in depth between the main image and additional image, and depth contradiction, can be prevented at the time of displaying an additional image in a display region having a position or size specified by the user.

The input unit may further accept instruction to change the size of the display region, the display region candidate deciding unit changing the size of the candidate region of the display region following the instruction to change the size which the input unit has accepted. In this case, the size of the display region of the additional image cab be changed.

The main image may be a video inside the body of the patient. In this case, the 3D display device can be used for surgery.

An image of a surgical instrument may be displayed in the main image. The input unit may accept input of the position, using information of the position of the surgical instrument in the main image.

In this case, the user can specify the size of the additional image using the instruments being used for surgery, without using any special interface device. That is to say, the user who is the surgeon can instruct the size of the additional image without releasing the surgical instruments. Thus, the 3D display device can be operated without sacrificing efficiency in surgery.

The input unit may include a passage detecting unit that detects whether or not a tip of the surgical instrument in the main image has passed through the display region of the additional image, and a display control signal generating unit that, in a case where the passage detecting unit has detected the passage, changes the size of the candidate region of the display region in accordance with the direction of passage of the surgical instrument.

In this case, the size of the candidate region can be changed so that the tip of the surgical instrument is not hidden by the additional image. This can prevent the tip of the surgical instrument being hidden by the additional image and impeding surgery.

The input unit may further accept instruction to change the position of the display region, the display region candidate deciding unit changing the position of the candidate region of the display region following the instruction to change the position which the input unit has accepted. In this case, the position of the display region of the additional image can be changed.

The three-dimensional display device may further include a display-forbidden region storage unit that stores a display-forbidden region, which is a region on the screen where display of the additional image is forbidden. The display region candidate deciding unit may decide the candidate region, which does not overlap the display-forbidden region stored in the display-forbidden region storage unit, based on the instruction which the input unit has accepted. This prevents important portions in the main image from being shielded from view by the additional image.

The main image may be a video inside the body of the patient, and the additional image may be an image of graphs of a plurality of types of biological data of the patient, which changes over time.

In this case, an additional image of graphs of multiple types of biological data necessary for surgery can be displayed on the screen, thus supporting the surgery being performed by the surgeon.

The display region candidate deciding unit may decide the candidate region having a shape corresponding to a layout of the graphs of the plurality of types of biological data. In this case, the display region of the additional image can be changed according to the layout of the graphs.

The layout may include a layout where the graphs of the plurality of types of biological data are arrayed vertically, and a layout where the graphs of the plurality of types of biological data are arrayed horizontally.

In a case where the depth suitability determination unit determines that the difference in depth of the candidate region is not within the tolerance range even if the position or size is changed, the display region candidate deciding unit may change the layout of the graphs of the plurality of types of biological data.

The display region candidate deciding unit may extract a portion in the main image where the depth exceeds a predetermined value as being a portion where protrusion from the screen is great, and decide a candidate region of the display region of the additional image to shield the portion where protrusion from the screen is great.

In this case, the additional image can be displayed to shield a portion protruding to the near side excessively, for example, and accordingly depth contradiction between the main image and additional image, and excessively large difference in depth, can be prevented.

Software which realizes the 3D display device according to the embodiments, and so forth, is a program such as follows. The program causes a computer to execute first deciding of one candidate region from a plurality of display region candidates of an additional image which shields part of a main image of a three-dimensional image on a screen; determining, in a case of assuming that the additional image is to be displayed in the candidate region which the display region candidate deciding unit has decided, whether or not a difference in depth between depth of the main image displayed at a boundary region which is a region on the main image and within a predetermined distance from a boundary line of the candidate region, and the depth of the additional image, is within a predetermined tolerance range; superimposing, in a case where determination is made in the determining that the difference in depth is within the tolerance range, the additional image upon the candidate region on the main image, thereby compositing the main image and the additional image, and displaying an image obtained as a result of the compositing on the screen; and second deciding, in the main image, of a first region that has a possibility of the depth protruding to a near side beyond a predetermined depth range, and a second region that has a possibility of the depth recessing to a far side beyond a predetermined depth range. The first deciding further decides a candidate region to shield the first region and the second region decided in the second deciding.

The present disclosure is applicable to a display device which displays 3D images or 3D video, and particularly to a display device of images and the like imaged by a stereo endoscope camera, a display device of recorded contents obtained by recording images, a medical 3D image display device, a monitor display device for are remotely operated robot, and so forth.

What is claimed is:

1. A three-dimensional display device configured to display a main image and an additional image on a screen, the three-dimensional display device comprising:
    a memory that stores instructions; and
    a processor, when executing the instructions stored in the memory, that performs operations including:
        deciding one candidate region from a plurality of region candidates for the additional image to be superimposed on the main image on the screen;
        determining, a based on a boundary region that is within a predetermined distance from a boundary line between the candidate region and outside of the candidate region in the main image, whether a difference between a depth of the main image displayed at the boundary region and a depth of the additional image is within a predetermined tolerance range;
        superimposing, when it is determined that the difference in depth between the depth of the main image displayed at the boundary region and the depth of the additional image is within the predetermined tolerance range, the additional image upon the main image at the candidate region, thereby composing a composite image of the main image and the additional image; and
        displaying the composite image on the screen.

2. The three-dimensional display device according to claim 1,
    wherein, when it is determined that the difference in depth is not within the predetermined tolerance range, the processor re-decides the candidate region.

3. The three-dimensional display device according to claim 1,
    wherein the processor divides the boundary region into a predetermined number of partial regions, calculates a difference in depth between the depth of the main image displayed at the partial region and the depth of the additional image for each partial region, and determines whether or not a maximum value of the calculated difference in depth is within the predetermined tolerance range, thereby determining whether or not the difference in depth between the depth of the main image displayed in the boundary region and the depth of the additional image is within the predetermined tolerance range.

4. The three-dimensional display device according to claim 1,
    wherein the processor,
        when it is determined that the difference in depth is within the predetermined tolerance range, composes, as the composite image, an image where the additional image having a first frame is superimposed on the candidate region on the main image, and displays the composite image on the screen, and
        when it is determined that the difference in depth is not within the predetermined tolerance range, composes, as the composite image, an image where the additional image having a second frame, which is broader than the first frame, is superimposed on the candidate region on the main image, and displays the composite image on the screen.

5. The three-dimensional display device according to claim 1, further comprising:
    a storage that stores a display-forbidden region, which is a region on the screen where display of the additional image is forbidden,
    wherein the processor decides one candidate region from the plurality of region candidates for the additional image, which does not overlap the display-forbidden region.

6. The three-dimensional display device according to claim 5,
    wherein the processor adds a correction value, which is larger the closer a distance from the candidate region to the display-forbidden region is, to the difference in depth, and thereupon determines whether or not the difference in depth is within the predetermined tolerance range.

7. The three-dimensional display device according to claim 5,
    wherein, the shorter a distance between a camera which has imaged the main image and an object displayed in the display-forbidden region, the larger the size of the display-forbidden region.

8. The three-dimensional display device according to claim 1,
    wherein the processor decides the candidate region giving priority to a candidate at a position closest to the display region of the additional image immediately previously displayed on the screen.

9. The three-dimensional display device according to claim 1, wherein the processor, when executing the instructions stored in the memory, further performs operations including:
    deciding a candidate region at predetermined time intervals, from candidate regions in which the difference in depth is within the predetermined tolerance range according to the determination results regarding whether or not the difference in depth between the depth of the main image and the depth of the additional image is within the predetermined tolerance range, for each of the plurality of candidates of the display region of the additional image, at every predetermined time interval, so that from a start of displaying the main image, which is a prerecorded three-dimensional image, to an end of displaying, the distance of movement or number of times of movement of the display region of the additional image is smallest,
    wherein the processor composes, as the composite image, an image where the additional image is superimposed on the main image, such that the additional image is displayed at the candidate region decided for each predetermined time interval, and displays the composite image on the screen.

10. The three-dimensional display device according to claim 9,
    wherein the main image is a three-dimensional image imaged by an endoscope camera.

11. The three-dimensional display device according to claim 10, further comprising:
a storage that stores a display-forbidden region, which is a region on the screen where display of the additional image is forbidden,
wherein the processor decides one candidate region from the plurality of region candidates of the additional image, which does not overlap the display-forbidden region stored in the storage,
and wherein the display-forbidden region is a region of the main image including an image of an affected area to be treated by surgery.

12. The three-dimensional display device according to claim 1,
wherein the additional image is an image indicating at least one of blood pressure, blood oxygen level distribution, respiration, expiration, body temperature, cardioelectric potential, brainwaves, and pulse waves, of the patient during surgery.

13. The three-dimensional display device according to claim 1, further comprising:
an input that accepts instruction of at least one of a position and a size of the display region of the additional image displayed on the screen,
wherein the processor decides a candidate region for the display region of the additional image, based on the instruction which the input has accepted.

14. The three-dimensional display device according to claim 13,
wherein the input further accepts instruction to change the size of the display region,
and wherein the processor changes the size of the candidate region of the display region following the instruction to change the size which the input has accepted.

15. The three-dimensional display device according to claim 13,
wherein the main image is a video of an inside of a body of a patient.

16. The three-dimensional display device according to claim 15,
wherein an image of a surgical instrument is displayed in the main image,
and wherein the input accepts input of the position, using information of the position of the surgical instrument in the main image.

17. The three-dimensional display device according to claim 16,
wherein the input includes
a passage detector that detects whether or not a tip of the surgical instrument in the main image has passed through the display region of the additional image, and
a display control signal generator that, when the passage detector has detected the passage, changes a size of the candidate region of the display region in accordance with a direction of passage of the surgical instrument.

18. The three-dimensional display device according to claim 13,
wherein the input further accepts instruction to change the position of the display region,
and wherein the processor changes the position of the candidate region of the display region following the instruction to change the position which the input has accepted.

19. The three-dimensional display device according to claim 13, further comprising:
a storage that stores a display-forbidden region, which is a region on the screen where display of the additional image is forbidden,
wherein the processor decides the candidate region, which does not overlap the display-forbidden region, based on the instruction which the input has accepted.

20. The three-dimensional display device according to claim 15,
wherein the main image is a video of an inside of a body of a patient,
and wherein the additional image is an image of graphs of a plurality of types of biological data of the patient, which changes over time.

21. The three-dimensional display device according to claim 20,
wherein the processor decides the candidate region having a shape corresponding to a layout of the graphs of the plurality of types of biological data.

22. The three-dimensional display device according to claim 21,
wherein the layout includes
a layout where the graphs of the plurality of types of biological data are arrayed vertically, and
a layout where the graphs of the plurality of types of biological data are arrayed horizontally.

23. The three-dimensional display device according to claim 21,
wherein, when the processor determines that the difference in depth of the candidate region is not within the predetermined tolerance range even if the position or size is changed, the processor changes the layout of the graphs of the plurality of types of biological data.

24. The three-dimensional display device according to claim 13,
wherein the processor extracts a portion in the main image where the depth exceeds a predetermined value as being a portion where protrusion from the screen is great, and decides a candidate region of the display region of the additional image to shield the portion where protrusion from the screen is great.

25. A three-dimensional display method for displaying a main image and an additional image on a screen of a three-dimensional display device, the method comprising:
deciding one candidate region from a plurality of region candidates for the additional image to be superimposed on the main image on the screen;
determining, based on a boundary region that is within a predetermined distance from a boundary line between the candidate region and outside of the candidate region in the main image, whether a difference between a depth of the main image displayed at the boundary region and a depth of the additional image is within a predetermined tolerance range; and
superimposing, when it is determined that the difference in depth between the depth of the main image displayed at the boundary region and the depth of the additional image is within the predetermined tolerance range, the additional image on the main image, thereby composing, as a composite image, the main image and the additional image, and displaying the composite image on the screen.

26. A non-transitory computer-readable recording medium storing a program causing a computer to execute the three-dimensional display method according to claim 25.

27. The three-dimensional display device according to claim 1,
- wherein the processor determines whether the difference obtained by subtracting the depth of the main image displayed at the boundary region from the depth of the additional image is equal to or greater than a predetermined tolerance value,
- and wherein the processor superimposes the additional image upon the main image at the candidate region, when it is determined that the obtained difference is equal to or greater than the predetermined tolerance value.

28. The three-dimensional display device according to claim 1,
- wherein the processor determines whether the main image displayed at the boundary region protrudes to a nearer side of the screen than the additional image,
- and wherein the processor superimposes the additional image upon the main image at the candidate region, when it is determined that the main image displayed at the boundary region does not protrude to the nearer side of the screen than the additional image.

* * * * *